United States Patent
Luettgen et al.

(10) Patent No.: US 9,597,161 B2
(45) Date of Patent: Mar. 21, 2017

(54) ORAL IRRIGATOR WITH INTEGRATED LID AND BASE

(71) Applicant: Water Pik, Inc., Fort Collins, CO (US)

(72) Inventors: Harold A. Luettgen, Windsor, CO (US); Kurt M. Taylor, Fort Collins, CO (US)

(73) Assignee: Water Pik, Inc., Fort Collins, CO (US)

( * ) Notice: Subject to any disclaimer, the term of this patent is extended or adjusted under 35 U.S.C. 154(b) by 554 days.

(21) Appl. No.: 14/208,806

(22) Filed: Mar. 13, 2014

(65) Prior Publication Data

US 2015/0004559 A1    Jan. 1, 2015

Related U.S. Application Data

(63) Continuation-in-part of application No. 13/831,401, filed on Mar. 14, 2013.
(Continued)

(51) Int. Cl.
*A61C 17/02* (2006.01)
*A61C 1/00* (2006.01)
(Continued)

(52) U.S. Cl.
CPC .......... *A61C 1/0092* (2013.01); *A61C 1/0015* (2013.01); *A61C 17/0205* (2013.01); *A61C 17/028* (2013.01); *A61H 13/005* (2013.01)

(58) Field of Classification Search
CPC .... A61H 13/00; A61H 13/005; A61H 9/0071; A61C 17/02; A61C 17/0202;
(Continued)

(56) References Cited

U.S. PATENT DOCUMENTS

| 555,588 A | 3/1896 | Spencer |
|---|---|---|
| 1,278,225 A | 9/1918 | Schamberg |

(Continued)

FOREIGN PATENT DOCUMENTS

| CA | 851479 | 9/1970 |
|---|---|---|
| CH | 502817 A | 2/1971 |

(Continued)

OTHER PUBLICATIONS

US RE27,274, 01/1972, Mattingly (withdrawn)
(Continued)

*Primary Examiner* — Justine Yu
*Assistant Examiner* — Michael Tsai
(74) *Attorney, Agent, or Firm* — Dorsey & Whitney LLP

(57) ABSTRACT

An irrigating device including a massage mode module in communication with a motor driving a pump. During a normal mode the pump has a first pulse rate and during massage mode the massage mode module provides a massage control signal to the motor to cause the pump to have a second pulse rate. In other embodiments, the disclosure includes an oral irrigator including a base and a reservoir removably connected to the base. The oral irrigator further includes a prow operably connected to the base and extending vertically upwards from the base. The prow may extend in a similar direction as sidewalls of the reservoir. The oral irrigator further includes a lid rotatably connected to the prow. The lid rotates between a first position where a fluid cavity of the reservoir is exposed to a second position where the lid covers at least a portion of the fluid cavity.

17 Claims, 34 Drawing Sheets

Related U.S. Application Data

(60) Provisional application No. 61/897,762, filed on Oct. 30, 2013.

(51) Int. Cl.
*A61C 17/028* (2006.01)
*A61H 13/00* (2006.01)

(58) Field of Classification Search
CPC ............ A61C 17/0205; A61C 17/0211; A61C 17/028; A61C 19/02
USPC ........................................ 206/63.5, 368, 369
See application file for complete search history.

(56) References Cited

U.S. PATENT DOCUMENTS

| | | |
|---|---|---|
| 1,464,419 A | 8/1923 | Gill |
| 1,498,267 A | 6/1924 | Hachman |
| 1,650,686 A | 11/1927 | Binks |
| 1,669,889 A | 5/1928 | Andrews et al. |
| 1,681,320 A | 8/1928 | Bergl et al. |
| 1,933,454 A | 10/1933 | Sidney |
| 2,107,686 A | 2/1938 | Bramsen et al. |
| 2,230,238 A | 2/1941 | Duberstein et al. |
| 2,417,759 A | 3/1947 | Johnson |
| 2,669,233 A | 2/1954 | Friend |
| 2,794,437 A | 6/1954 | Tash |
| 2,783,919 A | 3/1957 | Ansell |
| 2,870,932 A | 1/1959 | Davis |
| 2,984,452 A | 5/1961 | Hooper |
| 3,089,490 A | 5/1963 | Goldberg |
| 3,096,913 A | 7/1963 | Jousson |
| 3,144,867 A | 8/1964 | Trupp et al. |
| 3,209,956 A | 10/1965 | McKenzie |
| 3,216,619 A | 11/1965 | Richards et al. |
| 3,225,759 A | 12/1965 | Drapen et al. |
| 3,227,158 A | 1/1966 | Mattingly |
| 3,266,623 A | 8/1966 | Poferl |
| 3,297,558 A | 1/1967 | Hillquist |
| D208,778 S | 10/1967 | Koch |
| D209,204 S | 11/1967 | St. Clair et al. |
| D209,395 S | 11/1967 | Gilbert |
| D210,018 S | 1/1968 | Mattingly et al. |
| D210,019 S | 1/1968 | Johnson et al. |
| 3,370,214 A | 2/1968 | Aymar |
| 3,391,696 A | 7/1968 | Woodward |
| 3,393,673 A | 7/1968 | Mattingly et al. |
| 3,400,999 A | 9/1968 | Goldstein |
| 3,418,552 A | 12/1968 | Holmes |
| 3,420,228 A | 1/1969 | Kalbfeld |
| 3,425,410 A | 2/1969 | Cammack |
| 3,453,969 A | 7/1969 | Mattingly |
| 3,465,751 A | 9/1969 | Powers |
| 3,487,828 A | 1/1970 | Troy |
| 3,489,268 A | 1/1970 | Meierhoefer |
| 3,495,587 A | 2/1970 | Freedman |
| 3,496,933 A | 2/1970 | Lloyd |
| 3,499,440 A | 3/1970 | Gibbs |
| 3,500,824 A | 3/1970 | Gilbert |
| 3,501,203 A | 3/1970 | Falk |
| 3,502,072 A | 3/1970 | Stillman |
| 3,517,669 A | 6/1970 | Buono et al. |
| D218,270 S | 8/1970 | Soper |
| 3,522,801 A | 8/1970 | Robinson |
| 3,532,221 A | 10/1970 | Kaluhiokalani et al. |
| 3,536,065 A | 10/1970 | Moret |
| 3,537,444 A | 11/1970 | Garn |
| 3,538,950 A | 11/1970 | Porteners |
| 3,547,110 A | 12/1970 | Balamuth |
| 3,561,433 A | 2/1971 | Kovach |
| D220,334 S | 3/1971 | Mackay et al. |
| 3,570,525 A | 3/1971 | Borsum |
| 3,572,375 A | 3/1971 | Rosenberg |
| 3,578,884 A | 5/1971 | Jacobson |
| 3,583,609 A | 6/1971 | Oppenheimer |
| 3,590,813 A | 7/1971 | Roszyk |
| 3,608,548 A | 9/1971 | Lewis |
| D222,862 S | 1/1972 | Cook |
| 3,636,947 A | 1/1972 | Balamuth |
| 3,651,576 A | 3/1972 | Massa |
| 3,669,101 A | 6/1972 | Kleiner |
| 3,703,170 A | 11/1972 | Ryckman, Jr. |
| 3,747,595 A | 7/1973 | Grossan |
| 3,768,472 A | 10/1973 | Hodosh et al. |
| 3,783,364 A | 1/1974 | Gallanis et al. |
| 3,809,506 A | 5/1974 | Malcosky |
| 3,809,977 A | 5/1974 | Balamuth et al. |
| 3,811,432 A | 5/1974 | Moret |
| 3,820,532 A | 6/1974 | Eberhardt et al. |
| 3,827,147 A | 8/1974 | Condon |
| 3,837,166 A | 9/1974 | Hiraoka |
| 3,840,795 A | 10/1974 | Roszyk et al. |
| 3,847,145 A | 11/1974 | Grossan |
| 3,854,209 A | 12/1974 | Franklin et al. |
| 3,863,628 A | 2/1975 | Vit |
| 3,874,506 A | 4/1975 | Hill et al. |
| 3,881,868 A | 5/1975 | Duke |
| 3,898,739 A | 8/1975 | Gayso |
| 3,912,125 A | 10/1975 | Acklin |
| 3,943,628 A | 3/1976 | Kronman et al. |
| 3,959,883 A | 6/1976 | Walls et al. |
| 3,973,558 A | 8/1976 | Stouffer et al. |
| 3,977,084 A | 8/1976 | Sloan |
| 4,001,526 A | 1/1977 | Olson |
| 4,004,302 A | 1/1977 | Hori |
| 4,007,739 A | 2/1977 | Bron et al. |
| 4,052,002 A | 10/1977 | Stouffer et al. |
| D246,667 S | 12/1977 | Mackay et al. |
| 4,060,870 A | 12/1977 | Cannarella |
| 4,075,761 A | 2/1978 | Behne et al. |
| 4,078,558 A | 3/1978 | Woog et al. |
| 4,089,079 A | 5/1978 | Nicholson |
| 4,108,167 A | 8/1978 | Hickman et al. |
| 4,108,178 A | 8/1978 | Betush |
| 4,109,650 A | 8/1978 | Peclard |
| 4,122,845 A | 10/1978 | Stouffer et al. |
| 4,135,501 A | 1/1979 | Leunissan |
| 4,141,352 A | 2/1979 | Ebner et al. |
| 4,144,646 A | 3/1979 | Takemoto et al. |
| 4,149,315 A | 4/1979 | Page, Jr. et al. |
| 4,154,375 A | 5/1979 | Bippus |
| 4,160,383 A | 7/1979 | Rauschenberger |
| 4,182,038 A | 1/1980 | Fleer |
| 4,201,200 A | 5/1980 | Hubner |
| 4,215,476 A | 8/1980 | Armstrong |
| 4,219,618 A | 8/1980 | Leonard |
| 4,227,878 A | 10/1980 | Lohn |
| 4,229,634 A | 10/1980 | Hickman et al. |
| 4,236,889 A | 12/1980 | Wright |
| 4,248,589 A | 2/1981 | Lewis |
| 4,249,899 A | 2/1981 | Davis |
| 4,257,458 A | 3/1981 | Kondo et al. |
| 4,262,799 A | 4/1981 | Perrett |
| 4,266,934 A | 5/1981 | Pernot |
| 4,276,023 A | 6/1981 | Phillips et al. |
| 4,276,880 A | 7/1981 | Malmin |
| 4,302,186 A | 11/1981 | Cammack et al. |
| 4,303,064 A | 12/1981 | Buffa |
| 4,303,070 A | 12/1981 | Ichikawa et al. |
| 4,306,862 A * | 12/1981 | Knox ...................... A61C 3/04 |
| | | 206/210 |
| 4,315,741 A | 2/1982 | Reichl |
| 4,319,568 A | 3/1982 | Tregoning |
| 4,331,422 A | 5/1982 | Heyman |
| 4,337,040 A | 6/1982 | Cammack et al. |
| 4,340,365 A | 7/1982 | Pisanu |
| 4,340,368 A | 7/1982 | Lococo |
| D266,117 S | 9/1982 | Oberheim |
| 4,353,694 A | 10/1982 | Pelerin |
| 4,363,626 A | 12/1982 | Schmidt et al. |
| 4,365,376 A | 12/1982 | Oda et al. |
| 4,370,131 A | 1/1983 | Banko |
| 4,374,354 A | 2/1983 | Petrovic et al. |
| 4,382,167 A | 5/1983 | Maruyama et al. |

(56) References Cited

U.S. PATENT DOCUMENTS

| | | |
|---|---|---|
| 4,382,786 A | 5/1983 | Lohn |
| D270,000 S | 8/1983 | Ketler |
| 4,412,823 A | 11/1983 | Sakai et al. |
| 4,442,830 A | 4/1984 | Markau |
| 4,442,831 A | 4/1984 | Trenary |
| 4,452,238 A | 6/1984 | Kerr |
| 4,454,866 A | 6/1984 | Fayen |
| 4,512,769 A | 4/1985 | Kozam et al. |
| 4,517,962 A | 5/1985 | Heckele |
| 4,531,912 A | 7/1985 | Schuss et al. |
| 4,531,913 A | 7/1985 | Taguchi |
| 4,534,340 A | 8/1985 | Kerr et al. |
| 4,552,130 A | 11/1985 | Kinoshita |
| 4,561,214 A | 12/1985 | Inoue |
| D283,374 S | 4/1986 | Cheuk-Yiu |
| 4,585,415 A | 4/1986 | Hommann |
| 4,591,777 A | 5/1986 | McCarty et al. |
| 4,592,728 A | 6/1986 | Davis |
| 4,602,906 A | 7/1986 | Grunenfelder |
| 4,607,627 A | 8/1986 | Leber et al. |
| 4,613,074 A | 9/1986 | Schulze |
| 4,619,009 A | 10/1986 | Rosenstatter |
| 4,619,612 A | 10/1986 | Weber et al. |
| 4,629,425 A | 12/1986 | Detsch |
| 4,636,198 A | 1/1987 | Stade |
| 4,642,037 A | 2/1987 | Fritchman |
| 4,644,937 A | 2/1987 | Hommann |
| 4,645,488 A | 2/1987 | Matukas |
| 4,647,831 A | 3/1987 | O'Malley et al. |
| 4,648,838 A | 3/1987 | Schlachter |
| 4,650,475 A | 3/1987 | Smith et al. |
| 4,655,198 A | 4/1987 | Hommann |
| 4,669,453 A | 6/1987 | Atkinson et al. |
| 4,672,953 A | 6/1987 | DiVito |
| 4,673,396 A | 6/1987 | Urbaniak |
| D291,354 S | 8/1987 | Camens |
| 4,716,352 A | 12/1987 | Hurn et al. |
| 4,749,340 A | 6/1988 | Ikeda et al. |
| 4,770,632 A * | 9/1988 | Ryder .................. F04B 49/125 433/101 |
| 4,783,321 A | 11/1988 | Spence |
| 4,787,845 A | 11/1988 | Valentine |
| 4,787,847 A | 11/1988 | Martin et al. |
| 4,798,292 A | 1/1989 | Hauze |
| 4,803,974 A | 2/1989 | Powell |
| 4,804,364 A | 2/1989 | Dieras et al. |
| 4,818,229 A | 4/1989 | Vasile |
| 4,820,152 A | 4/1989 | Warrin et al. |
| 4,821,923 A | 4/1989 | Skorka |
| 4,824,368 A | 4/1989 | Hickman |
| 4,826,431 A | 5/1989 | Fujimura et al. |
| 4,827,551 A | 5/1989 | Maser et al. |
| 4,832,683 A | 5/1989 | Idemoto et al. |
| 4,854,869 A | 8/1989 | Lawhorn |
| 4,861,340 A | 8/1989 | Smith et al. |
| 4,862,876 A | 9/1989 | Lih-Sheng |
| 4,869,720 A | 9/1989 | Chernack |
| 4,880,382 A | 11/1989 | Moret et al. |
| 4,886,452 A | 12/1989 | Lohn |
| 4,900,252 A | 2/1990 | Liefke et al. |
| 4,902,225 A | 2/1990 | Lohn |
| 4,903,687 A | 2/1990 | Lih-Sheng |
| 4,906,187 A | 3/1990 | Amadera |
| 4,907,744 A | 3/1990 | Jousson |
| 4,925,450 A | 5/1990 | Imonti et al. |
| 4,928,675 A | 5/1990 | Thornton |
| 4,930,660 A | 6/1990 | Porteous |
| 4,941,459 A | 7/1990 | Mathur |
| 4,950,159 A | 8/1990 | Hansen |
| 4,958,629 A | 9/1990 | Peace et al. |
| 4,958,751 A | 9/1990 | Curtis et al. |
| 4,959,199 A | 9/1990 | Brewer |
| 4,961,698 A | 10/1990 | Vlock |
| 4,966,551 A | 10/1990 | Betush |
| 4,969,874 A | 11/1990 | Michel et al. |
| 4,973,247 A | 11/1990 | Varnes et al. |
| 4,973,250 A | 11/1990 | Milman |
| 4,975,054 A | 12/1990 | Esrock |
| 4,979,503 A | 12/1990 | Chernack |
| 4,979,504 A | 12/1990 | Mills |
| 4,989,590 A | 2/1991 | Baum et al. |
| 4,998,880 A | 3/1991 | Nerli |
| 5,013,241 A | 5/1991 | Von Gutfeld et al. |
| 5,014,884 A | 5/1991 | Wunsch |
| 5,019,054 A | 5/1991 | Clement et al. |
| 5,027,798 A | 7/1991 | Primiano |
| 5,029,576 A | 7/1991 | Evans, Sr. |
| 5,033,617 A | 7/1991 | Hartwein et al. |
| 5,033,961 A | 7/1991 | Kankler et al. |
| D318,918 S | 8/1991 | Hartwein |
| 5,046,486 A | 9/1991 | Grulke et al. |
| 5,049,071 A | 9/1991 | Davis et al. |
| 5,060,825 A | 10/1991 | Palmer et al. |
| 5,061,180 A | 10/1991 | Wiele |
| 5,062,795 A | 11/1991 | Woog |
| 5,064,168 A | 11/1991 | Raines et al. |
| D322,314 S | 12/1991 | Ohbayashi |
| 5,071,346 A * | 12/1991 | Domaas .................. A61C 3/04 206/369 |
| 5,082,115 A | 1/1992 | Hutcheson |
| 5,082,443 A | 1/1992 | Lohn |
| 5,085,317 A | 2/1992 | Jensen et al. |
| 5,086,756 A | 2/1992 | Powell |
| 5,095,893 A | 3/1992 | Rawden, Jr. |
| 5,098,291 A | 3/1992 | Curtis et al. |
| 5,098,676 A | 3/1992 | Brooks, Jr. |
| 5,100,319 A | 3/1992 | Baum |
| 5,117,871 A | 6/1992 | Gardner et al. |
| 5,125,835 A | 6/1992 | Young |
| 5,127,831 A | 7/1992 | Bab |
| 5,142,723 A | 9/1992 | Lustig et al. |
| 5,150,841 A | 9/1992 | Silvenis et al. |
| 5,172,810 A | 12/1992 | Brewer |
| 5,173,273 A | 12/1992 | Brewer |
| 5,183,035 A | 2/1993 | Weir |
| 5,197,458 A | 3/1993 | Ito et al. |
| 5,197,460 A | 3/1993 | Ito et al. |
| 5,199,871 A | 4/1993 | Young |
| 5,203,697 A | 4/1993 | Malmin |
| 5,203,769 A | 4/1993 | Clement et al. |
| 5,204,004 A | 4/1993 | Johnston et al. |
| 5,208,933 A | 5/1993 | Lustig et al. |
| 5,215,193 A | 6/1993 | Dennis |
| 5,218,956 A | 6/1993 | Handler et al. |
| 5,220,914 A | 6/1993 | Thompson |
| 5,228,646 A | 7/1993 | Raines |
| 5,230,624 A | 7/1993 | Wolf et al. |
| 5,232,687 A | 8/1993 | Geimer |
| 5,235,968 A | 8/1993 | Woog |
| 5,241,714 A | 9/1993 | Barry |
| 5,246,367 A | 9/1993 | Ito et al. |
| 5,252,064 A | 10/1993 | Baum et al. |
| D341,200 S | 11/1993 | Yoshimoto |
| 5,257,933 A | 11/1993 | Jousson |
| 5,261,448 A | 11/1993 | Furuya et al. |
| D341,943 S | 12/1993 | Si-Hoe |
| 5,267,586 A | 12/1993 | Jankavaara |
| 5,269,684 A | 12/1993 | Fischer |
| 5,281,137 A | 1/1994 | Jousson |
| 5,281,139 A | 1/1994 | Frank et al. |
| 5,282,745 A | 2/1994 | Wiltrout et al. |
| 5,286,192 A | 2/1994 | Dixon |
| 5,286,201 A | 2/1994 | Yu |
| 5,297,962 A | 3/1994 | O'Connor et al. |
| D346,212 S | 4/1994 | Hosl |
| 5,301,381 A | 4/1994 | Klupt |
| 5,302,123 A | 4/1994 | Bechard |
| 5,317,691 A | 5/1994 | Traeger |
| 5,321,865 A | 6/1994 | Kaeser |
| 5,331,704 A | 7/1994 | Rosen et al. |
| 5,344,317 A | 9/1994 | Pacher et al. |
| 5,346,677 A | 9/1994 | Risk |
| D351,892 S | 10/1994 | Wolf et al. |
| 5,360,338 A | 11/1994 | Waggoner |

(56) References Cited

U.S. PATENT DOCUMENTS

| | | |
|---|---|---|
| 5,368,548 A | 11/1994 | Jousson |
| 5,370,534 A | 12/1994 | Wolf et al. |
| D354,168 S | 1/1995 | Hartwein |
| 5,378,149 A | 1/1995 | Stropko |
| 5,380,201 A | 1/1995 | Kawata |
| D356,864 S | 3/1995 | Woog |
| 5,399,089 A | 3/1995 | Eichman et al. |
| D358,883 S | 5/1995 | Vos |
| 5,456,672 A | 10/1995 | Diederich et al. |
| 5,465,445 A | 11/1995 | Yeh |
| 5,467,495 A | 11/1995 | Boland et al. |
| 5,468,148 A | 11/1995 | Ricks |
| 5,470,305 A | 11/1995 | Arnett et al. |
| 5,474,450 A | 12/1995 | Chronister |
| 5,474,451 A | 12/1995 | Dalrymple et al. |
| 5,476,379 A | 12/1995 | Disel |
| 5,484,281 A | 1/1996 | Renow et al. |
| 5,487,877 A | 1/1996 | Choi |
| 5,490,779 A | 2/1996 | Malmin |
| 5,505,916 A | 4/1996 | Berry, Jr. |
| D369,656 S | 5/1996 | Vos |
| 5,525,058 A | 6/1996 | Gallant et al. |
| 5,526,841 A | 6/1996 | Detsch et al. |
| 5,540,587 A | 7/1996 | Malmin |
| 5,547,374 A | 8/1996 | Coleman |
| D373,631 S | 9/1996 | Maeda et al. |
| 5,554,014 A | 9/1996 | Becker |
| 5,554,025 A | 9/1996 | Kinsel |
| 5,556,001 A | 9/1996 | Weissman et al. |
| 5,564,629 A | 10/1996 | Weissman et al. |
| D377,091 S | 12/1996 | Scott, Sr. |
| 5,616,028 A | 4/1997 | Hafele et al. |
| 5,626,472 A | 5/1997 | Pennetta |
| 5,634,791 A | 6/1997 | Matsuura et al. |
| 5,636,987 A | 6/1997 | Serfaty |
| 5,640,735 A | 6/1997 | Manning |
| 5,653,591 A | 8/1997 | Loge |
| 5,659,995 A | 8/1997 | Hoffman |
| 5,667,483 A | 9/1997 | Santos |
| D386,576 S | 11/1997 | Wang et al. |
| 5,683,192 A | 11/1997 | Kilfoil |
| 5,685,829 A | 11/1997 | Allen |
| 5,685,851 A | 11/1997 | Murphy et al. |
| 5,697,784 A | 12/1997 | Hafele et al. |
| D388,612 S | 1/1998 | Stutzer et al. |
| D388,613 S | 1/1998 | Stutzer et al. |
| 5,709,545 A | 1/1998 | Johnston et al. |
| 5,716,007 A | 2/1998 | Nottingham et al. |
| 5,718,668 A | 2/1998 | Arnett et al. |
| 5,746,595 A | 5/1998 | Ford |
| 5,749,726 A | 5/1998 | Kinsel |
| 5,759,502 A | 6/1998 | Spencer et al. |
| 5,779,654 A | 7/1998 | Foley et al. |
| 5,795,153 A | 8/1998 | Rechmann |
| 5,796,325 A | 8/1998 | Lundell et al. |
| 5,833,065 A | 11/1998 | Burgess |
| 5,836,030 A | 11/1998 | Hazeu et al. |
| D402,744 S | 12/1998 | Zuege |
| 5,851,079 A | 12/1998 | Horstman et al. |
| D403,511 S | 1/1999 | Serbinski |
| D406,334 S | 3/1999 | Rosenthal et al. |
| 5,876,201 A | 3/1999 | Wilson et al. |
| D408,511 S | 4/1999 | Allen et al. |
| 5,901,397 A | 5/1999 | Häfele et al. |
| 5,934,902 A | 8/1999 | Abahusayn |
| D413,975 S | 9/1999 | Maeda |
| D417,082 S | 11/1999 | Classen et al. |
| 5,993,402 A | 11/1999 | Sauer et al. |
| 6,030,215 A | 2/2000 | Ellion et al. |
| 6,038,960 A | 3/2000 | Fukushima et al. |
| 6,039,180 A | 3/2000 | Grant |
| 6,041,462 A | 3/2000 | Marques |
| 6,047,429 A | 4/2000 | Wu |
| D425,615 S | 5/2000 | Bachman et al. |
| D425,981 S | 5/2000 | Bachman et al. |
| 6,056,710 A | 5/2000 | Bachman et al. |
| D426,633 S | 6/2000 | Bachman et al. |
| 6,089,865 A | 7/2000 | Edgar |
| 6,116,866 A | 9/2000 | Tomita et al. |
| 6,124,699 A | 9/2000 | Suzuki et al. |
| D434,500 S | 11/2000 | Pollock et al. |
| 6,159,006 A | 12/2000 | Cook et al. |
| 6,164,967 A | 12/2000 | Sale et al. |
| D435,905 S | 1/2001 | Bachman et al. |
| D437,049 S | 1/2001 | Hartwein |
| 6,193,512 B1 | 2/2001 | Wallace |
| 6,193,932 B1 | 2/2001 | Wu et al. |
| 6,199,239 B1 | 3/2001 | Dickerson |
| 6,200,134 B1 | 3/2001 | Kovac |
| D439,781 S | 4/2001 | Spore |
| 6,217,835 B1 | 4/2001 | Riley et al. |
| D441,861 S | 5/2001 | Hafliger |
| 6,230,717 B1 | 5/2001 | Marx et al. |
| 6,233,773 B1 | 5/2001 | Karge et al. |
| 6,234,205 B1 | 5/2001 | D'Amelio et al. |
| 6,237,178 B1 | 5/2001 | Krammer et al. |
| 6,247,929 B1 | 6/2001 | Bachman et al. |
| D448,236 S | 9/2001 | Murray |
| 6,293,792 B1 | 9/2001 | Hanson |
| D449,884 S | 10/2001 | Tobin et al. |
| D453,453 S | 2/2002 | Lun |
| 6,363,565 B1 | 4/2002 | Paffrath |
| D464,799 S | 10/2002 | Crossman et al. |
| 6,468,482 B1 | 10/2002 | Frieze et al. |
| 6,475,173 B1 | 11/2002 | Bachman et al. |
| 6,485,451 B1 | 11/2002 | Roberts et al. |
| 6,497,375 B1 | 12/2002 | Srinath et al. |
| 6,497,572 B2 | 12/2002 | Hood et al. |
| 6,502,584 B1 | 1/2003 | Fordham |
| D470,660 S | 2/2003 | Schaber |
| 6,558,344 B2 | 5/2003 | McKinnon et al. |
| 6,561,808 B2 | 5/2003 | Neuberger et al. |
| D475,346 S | 6/2003 | McCurrach et al. |
| 6,589,477 B1 | 7/2003 | Frieze et al. |
| 6,602,071 B1 | 8/2003 | Ellion et al. |
| 6,632,091 B1 | 10/2003 | Cise et al. |
| D482,451 S | 11/2003 | Page et al. |
| 6,640,999 B2 | 11/2003 | Peterson |
| 6,647,577 B2 | 11/2003 | Tam |
| 6,659,674 B2 | 12/2003 | Carlucci et al. |
| 6,669,059 B2 | 12/2003 | Mehta |
| 6,681,418 B1 | 1/2004 | Bierend |
| D486,573 S | 2/2004 | Callaghan et al. |
| 6,689,078 B1 | 2/2004 | Rehkemper et al. |
| 6,699,208 B2 | 3/2004 | Bachman et al. |
| 6,719,561 B2 | 4/2004 | Gugel et al. |
| D489,183 S | 5/2004 | Akahori et al. |
| 6,739,782 B1 | 5/2004 | Rehkemper et al. |
| 6,740,053 B2 | 5/2004 | Kaplowitz |
| D490,899 S | 6/2004 | Gagnon |
| D491,728 S | 6/2004 | Jimenez |
| D492,996 S | 7/2004 | Rehkemper et al. |
| 6,761,324 B2 | 7/2004 | Chang |
| 6,766,549 B2 | 7/2004 | Klupt |
| D495,142 S | 8/2004 | Berde |
| D495,143 S | 8/2004 | Berde |
| 6,779,216 B2 | 8/2004 | Davies et al. |
| 6,783,004 B1 | 8/2004 | Rinner |
| 6,783,505 B1 | 8/2004 | Lai |
| 6,796,796 B2 | 9/2004 | Segal |
| D498,643 S | 11/2004 | Pryor |
| 6,814,259 B1 | 11/2004 | Foster et al. |
| D499,885 S | 12/2004 | Xi |
| 6,835,181 B2 | 12/2004 | Hippensteel |
| D500,599 S | 1/2005 | Callaghan |
| 6,837,708 B2 | 1/2005 | Chen et al. |
| 6,884,069 B2 | 4/2005 | Goldman |
| 6,902,337 B1 | 6/2005 | Kuo |
| 6,907,879 B2 | 6/2005 | Drinan et al. |
| D509,585 S | 9/2005 | Kling et al. |
| D513,638 S | 1/2006 | Pan |
| D522,652 S | 6/2006 | Massey |
| 7,080,980 B2 | 7/2006 | Klupt |
| D529,661 S | 10/2006 | Schmidt |

(56) References Cited

U.S. PATENT DOCUMENTS

| | | | |
|---|---|---|---|
| D530,010 S | 10/2006 | Luettgen et al. |
| 7,117,555 B2 | 10/2006 | Fattori et al. |
| 7,131,838 B2 | 11/2006 | Suzuki et al. |
| D533,720 S | 12/2006 | Vu |
| 7,147,468 B2 | 12/2006 | Snyder et al. |
| D538,474 S | 3/2007 | Sheppard et al. |
| D548,334 S | 8/2007 | Izumi |
| D550,097 S | 9/2007 | Lepoitevin |
| 7,276,035 B2 | 10/2007 | Lu |
| 7,314,456 B2 | 1/2008 | Shaw |
| D565,175 S | 3/2008 | Boyd et al. |
| 7,344,510 B1 | 3/2008 | Yande |
| D565,713 S | 4/2008 | Gao |
| 7,367,803 B2 | 5/2008 | Egeresi |
| D574,952 S | 8/2008 | Boyd et al. |
| D577,198 S | 9/2008 | Jimenez |
| D577,814 S | 9/2008 | Seki et al. |
| D581,279 S | 11/2008 | Oates |
| 7,455,521 B2 | 11/2008 | Fishburne, Jr. |
| 7,469,440 B2 | 12/2008 | Boland et al. |
| 7,500,584 B2 | 3/2009 | Schutz |
| D590,492 S | 4/2009 | Powell |
| D595,136 S | 6/2009 | Canamasas Puigbo |
| D601,697 S | 10/2009 | Sobiech et al. |
| D603,708 S | 11/2009 | Handy |
| 7,670,141 B2 | 3/2010 | Thomas et al. |
| 7,677,888 B1 | 3/2010 | Halm |
| D613,550 S | 4/2010 | Picozza et al. |
| D621,949 S | 8/2010 | Seki et al. |
| 7,814,585 B1 | 10/2010 | Reich |
| D629,884 S | 12/2010 | Stephens |
| 7,857,623 B2 | 12/2010 | Grez |
| 7,862,536 B2 | 1/2011 | Chen et al. |
| 7,878,403 B2 | 2/2011 | Hennick et al. |
| 7,959,597 B2 | 6/2011 | Baker et al. |
| D640,872 S | 7/2011 | Nanda |
| D648,539 S | 11/2011 | Wai |
| D651,805 S | 1/2012 | Hay |
| 8,113,832 B2 | 2/2012 | Snyder et al. |
| D658,381 S | 5/2012 | Gebski |
| 8,220,726 B2 | 7/2012 | Qiu et al. |
| D666,912 S | 9/2012 | Kawai |
| 8,256,979 B2 | 9/2012 | Hilscher et al. |
| D668,339 S | 10/2012 | Luoto |
| D669,169 S | 10/2012 | Washington et al. |
| 8,297,534 B2 | 10/2012 | Li et al. |
| D670,373 S | 11/2012 | Taylor et al. |
| D670,958 S | 11/2012 | Picozza et al. |
| D671,637 S | 11/2012 | Gebski et al. |
| 8,366,024 B2 | 2/2013 | Leber |
| 8,403,577 B2 | 3/2013 | Khoshnevis |
| 8,403,665 B2 | 3/2013 | Thomas et al. |
| 8,408,483 B2 | 4/2013 | Boyd et al. |
| D694,398 S | 11/2013 | Taylor |
| D707,350 S | 6/2014 | Woodard |
| 8,801,667 B2 | 8/2014 | Taylor |
| D731,640 S | 6/2015 | Kim et al. |
| 9,050,157 B2 | 6/2015 | Boyd et al. |
| D747,464 S | 1/2016 | Taylor |
| 2002/0090252 A1 | 7/2002 | Hall et al. |
| 2002/0108193 A1 | 8/2002 | Gruber |
| 2002/0119415 A1 | 8/2002 | Bailey |
| 2002/0152565 A1 | 10/2002 | Klupt |
| 2003/0060743 A1* | 3/2003 | Chang .................. A61C 17/02 601/162 |
| 2003/0098249 A1 | 5/2003 | Rollock |
| 2003/0204155 A1 | 10/2003 | Egeresi |
| 2003/0213075 A1 | 11/2003 | Hui et al. |
| 2004/0045107 A1 | 3/2004 | Egeresi |
| 2004/0076921 A1 | 4/2004 | Gofman et al. |
| 2004/0122377 A1 | 6/2004 | Fischer et al. |
| 2004/0126730 A1 | 7/2004 | Panagotacos |
| 2004/0209222 A1 | 10/2004 | Snyder |
| 2005/0004498 A1 | 1/2005 | Klupt |
| 2005/0049620 A1 | 3/2005 | Chang |
| 2005/0064371 A1 | 3/2005 | Soukos et al. |
| 2005/0101894 A1 | 5/2005 | Hippensteel |
| 2005/0102773 A1 | 5/2005 | Obermann et al. |
| 2005/0144745 A1 | 7/2005 | Russell |
| 2005/0177079 A1 | 8/2005 | Pan |
| 2005/0271531 A1 | 12/2005 | Brown et al. |
| 2006/0008373 A1 | 1/2006 | Schutz |
| 2006/0010624 A1 | 1/2006 | Cleland |
| 2006/0021165 A1 | 2/2006 | Boland et al. |
| 2006/0026784 A1 | 2/2006 | Moskovich et al. |
| 2006/0057539 A1 | 3/2006 | Sodo |
| 2006/0078844 A1 | 4/2006 | Goldman et al. |
| 2006/0079818 A1 | 4/2006 | Yande |
| 2007/0082316 A1 | 4/2007 | Zhadanov et al. |
| 2007/0113360 A1 | 5/2007 | Tsai |
| 2007/0202459 A1 | 8/2007 | Boyd et al. |
| 2007/0203439 A1 | 8/2007 | Boyd et al. |
| 2007/0254260 A1 | 11/2007 | Alden |
| 2008/0008979 A1 | 1/2008 | Thomas et al. |
| 2008/0189951 A1 | 8/2008 | Molema et al. |
| 2008/0307591 A1 | 12/2008 | Farrell et al. |
| 2009/0070949 A1 | 3/2009 | Sagel et al. |
| 2009/0082706 A1 | 3/2009 | Shaw |
| 2009/0124945 A1 | 5/2009 | Reich et al. |
| 2009/0163839 A1 | 6/2009 | Alexander |
| 2009/0281454 A1 | 11/2009 | Baker et al. |
| 2010/0010524 A1 | 1/2010 | Barrington |
| 2010/0015566 A1 | 1/2010 | Shaw |
| 2010/0190132 A1 | 7/2010 | Taylor et al. |
| 2010/0239998 A1 | 9/2010 | Snyder et al. |
| 2010/0261134 A1 | 10/2010 | Boyd et al. |
| 2010/0261137 A1 | 10/2010 | Boyd et al. |
| 2010/0326536 A1 | 12/2010 | Nan |
| 2010/0330527 A1 | 12/2010 | Boyd et al. |
| 2011/0027749 A1 | 2/2011 | Syed |
| 2011/0076090 A1 | 3/2011 | Wu et al. |
| 2011/0097683 A1 | 4/2011 | Boyd et al. |
| 2011/0139826 A1 | 6/2011 | Hair et al. |
| 2011/0144588 A1 | 6/2011 | Taylor et al. |
| 2011/0184341 A1 | 7/2011 | Baker et al. |
| 2012/0021374 A1 | 1/2012 | Cacka et al. |
| 2012/0045730 A1 | 2/2012 | Snyder et al. |
| 2012/0064480 A1 | 3/2012 | Hegemann |
| 2012/0077145 A1 | 3/2012 | Tsurukawa |
| 2012/0141952 A1 | 6/2012 | Snyder et al. |
| 2012/0189976 A1 | 7/2012 | McDonough et al. |
| 2012/0266396 A1 | 10/2012 | Leung |
| 2012/0277677 A1 | 11/2012 | Taylor et al. |
| 2012/0277678 A1 | 11/2012 | Taylor et al. |
| 2012/0295220 A1 | 11/2012 | Thomas et al. |
| 2014/0193774 A1 | 7/2014 | Snyder et al. |
| 2014/0259474 A1 | 9/2014 | Sokol et al. |
| 2014/0352088 A1 | 12/2014 | Wu |
| 2016/0151133 A1 | 6/2016 | Luettgen et al. |

FOREIGN PATENT DOCUMENTS

| | | |
|---|---|---|
| CH | 655237 | 4/1987 |
| DE | 1466963 | 5/1969 |
| DE | 1566490 | 11/1970 |
| DE | 2409752 | 9/1975 |
| DE | 2545936 | 4/1977 |
| DE | 2910982 | 2/1980 |
| EP | 0023672 | 7/1980 |
| EP | 0515983 A1 | 12/1992 |
| FR | 2556954 | 6/1985 |
| FR | 2654627 | 5/1991 |
| GB | 1182031 | 2/1970 |
| GB | 2018605 | 10/1979 |
| GB | 2237505 | 5/1991 |
| JP | 2-134150 | 4/1990 |
| JP | 2009-39455 | 2/2009 |
| WO | WO95/16404 | 6/1995 |
| WO | 01/10327 A1 | 2/2001 |
| WO | WO01/19281 | 3/2001 |
| WO | WO2004/021958 | 3/2004 |
| WO | WO2004/039205 | 5/2004 |
| WO | 2004060259 A2 | 7/2004 |
| WO | 2008157585 A1 | 12/2008 |

(56) References Cited

FOREIGN PATENT DOCUMENTS

| WO | WO2013/095462 | 6/2013 |
|---|---|---|
| WO | 2013124691 A1 | 8/2013 |
| WO | WO2014145890 | 9/2014 |

OTHER PUBLICATIONS

The Right Tool, Electron Fusion Devices, Inc., 2 pages, at least as early as Feb. 1991.
Japanese Packaging, 2 pages, at least as early as Dec. 2002.
Japanese Instruction Brochure, 20 pages, at least as early as Dec. 2002.
Brochure: Woog International, "You have a 98% chance of getting gum disease. Unless you read this.", Lancaster, Pennsylvania, 5 pages, Feb. 1987.
Brochure: Woog International, "We put the control of home dental care back into the hands of the professional", Lancaster, Pennsylvania, 2 pages, Feb. 1987.
Brochure: Woog International, "Products at a Glance: Home Dental Care System" Woog Orajet, 3 pages, at least as early as Dec. 18, 1998.
Website: http://www.just4teeth.com/product/Panasonic/Panasonic_Portable_Irrigator.htm, 2 pages, at least as early as Jun. 20, 2003.
Website: http://www.videodirectstore.com/store/merchant.mv?Screen=PROD&Product_Code=EW1' . . . , 2 pages, at least as early as Jun. 20, 2003.
Website: http://products.consumerguide.com/cp/family/review/index.cfm/id/18742, 2 pages, at least as early as Jun. 20, 2003.
Website: http://www.racekarteng.com/images/walbroparts.gif and http://www.muller.net/mullermachine/docs/walbro1.html, 4 pages, at least as early as Jun. 20, 2003.
European Search Report, EPO Application No. 07250799.9, Jul. 5, 2007.
European Search Report, EPO Application No. 07252693.2, 14 pages, Apr. 28, 2008.
European Examination Report, EPO Application No. 07250799.9, Feb. 5, 2009.
International Search Report, Application No. PCT/US2010/028180, 2 pages, May 18, 2010.
International Search Report, PCT/US2010/060800, 2 pages, Feb. 11, 2011.
International Search Report, PCT/US2011/052795, 10 pages, Jan. 17, 2012.
Waterpik SinuSense Website: http://www.insightsbyapril.com/2012/03/waterpik-natural-remedy-for-sinus.html, 8 pages, retrieved on May 31, 2012.

\* cited by examiner

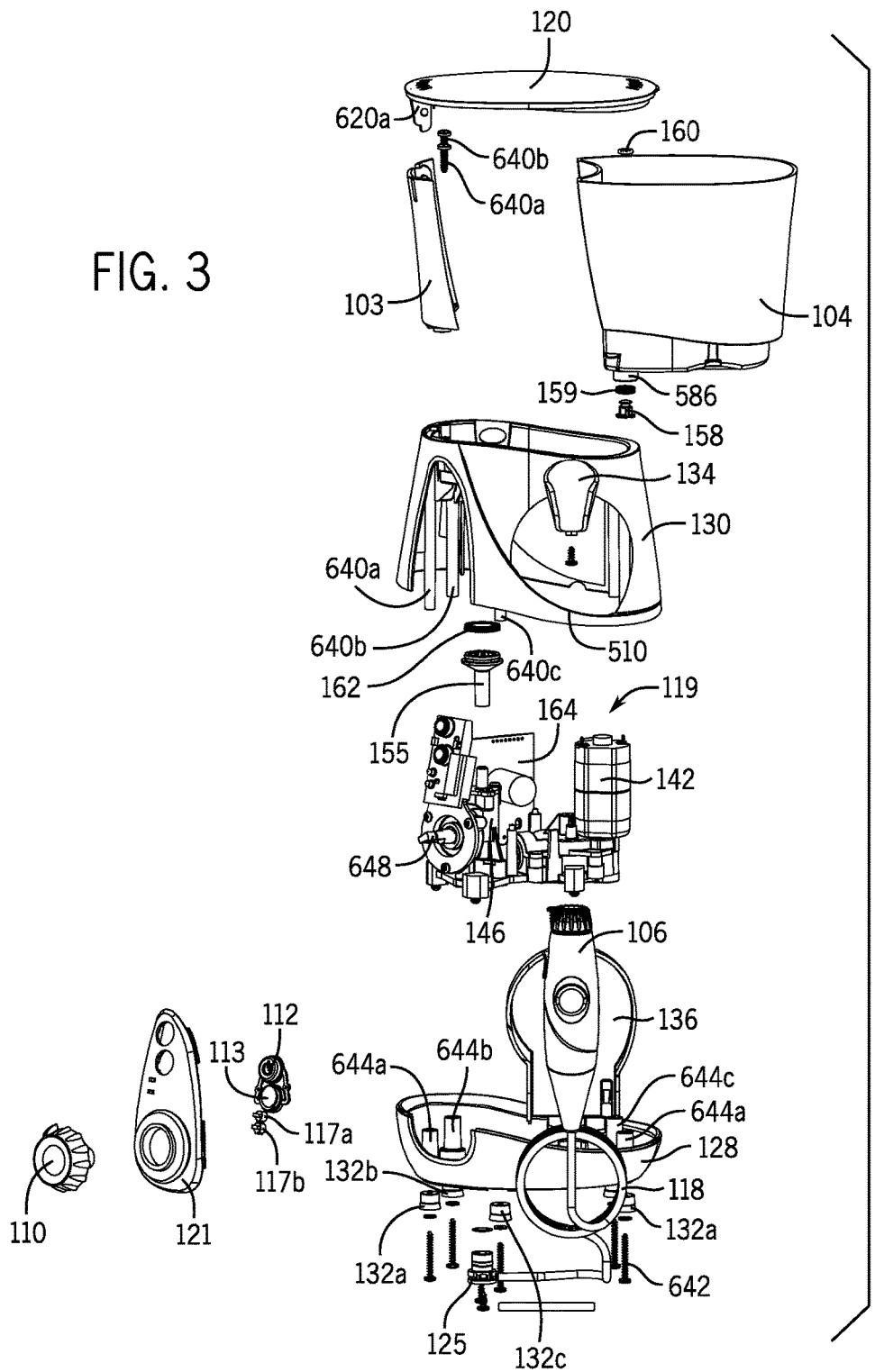

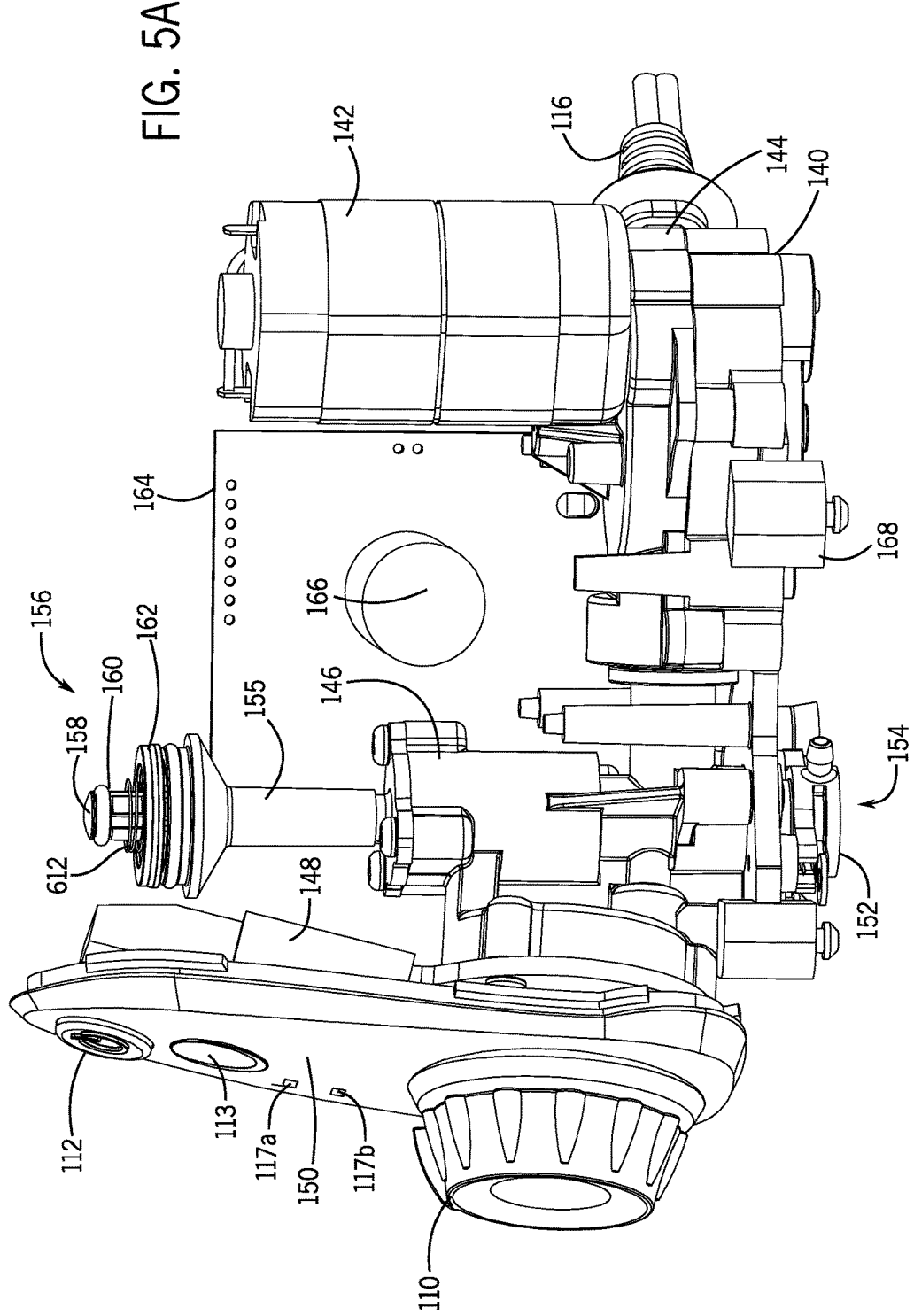

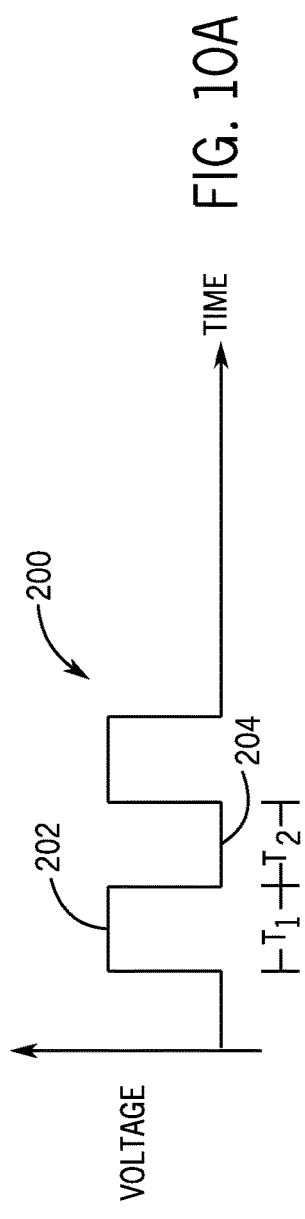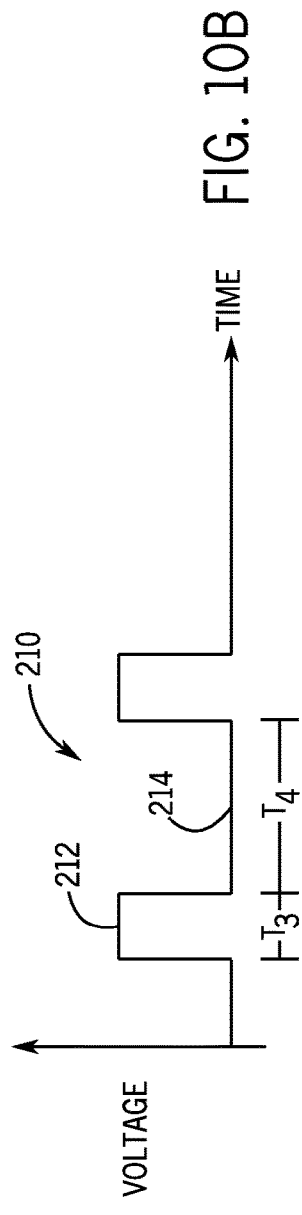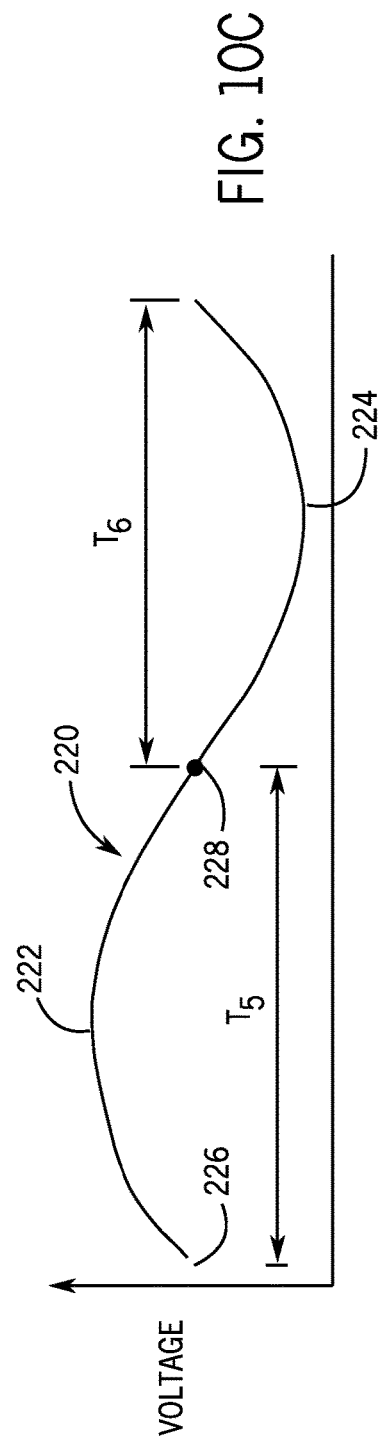

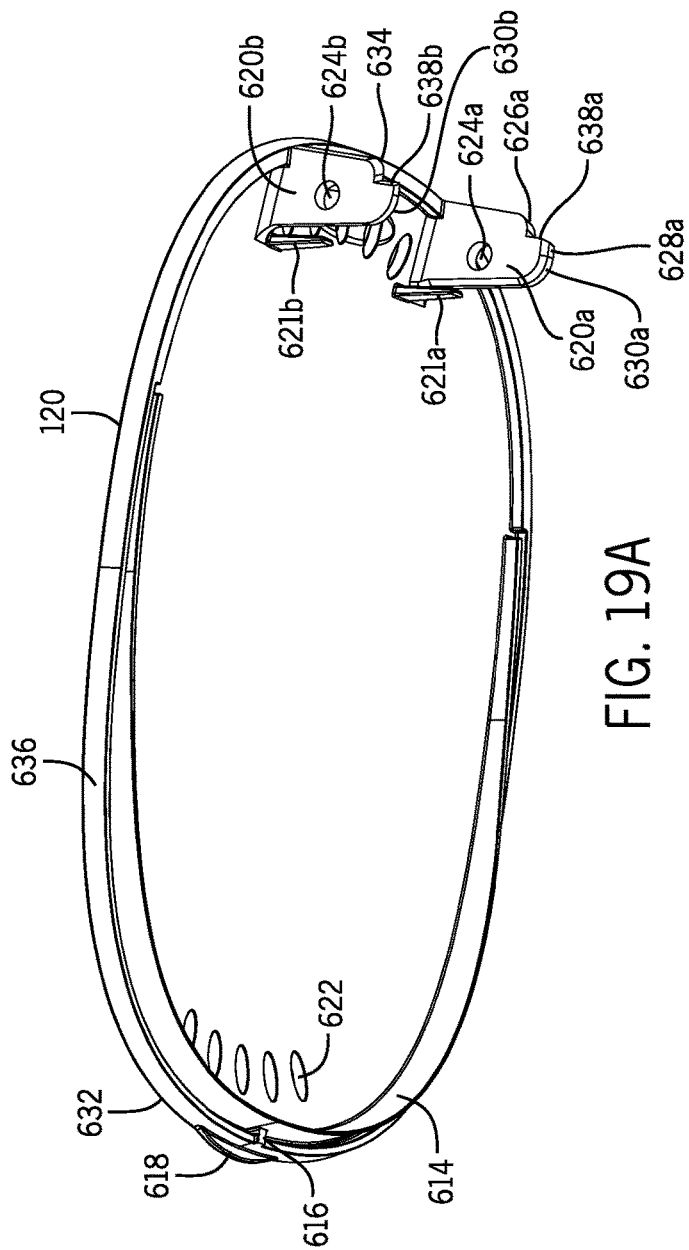
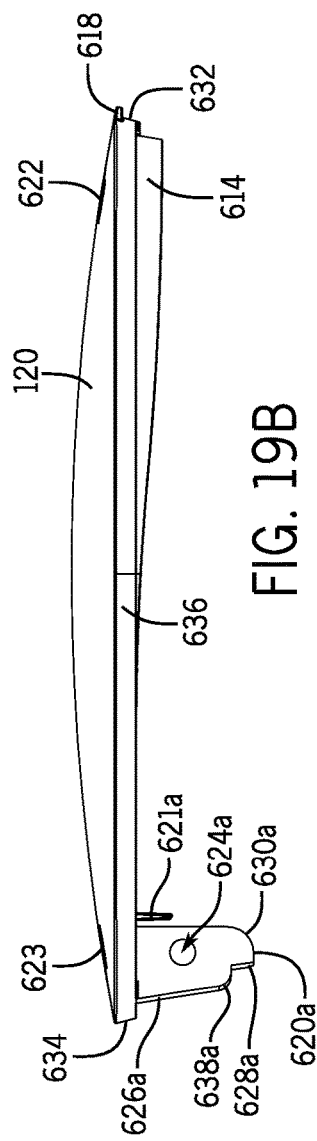
FIG. 19A
FIG. 19B

ORAL IRRIGATOR WITH INTEGRATED LID AND BASE

CROSS REFERENCE TO RELATED APPLICATIONS

This application is a continuation-in-part of U.S. non-provisional application Ser. No. 13/831,401 entitled "Oral Irrigator with Massage Mode," filed Mar. 14, 2013, and also claims the benefit of U.S. provisional application No. 61/897,762 entitled "Oral Irrigator with Integrated Lid and Base," filed Oct. 30, 2013, the disclosures of each are hereby incorporated herein by reference in their entireties.

TECHNICAL FIELD

The present invention relates to health and personal hygiene equipment and more particularly, to oral irrigators.

BACKGROUND

Oral irrigators typically are used to clean a user's teeth and gums by discharging a pressurized fluid stream into a user's oral cavity. The fluid impacts the teeth and gums to remove debris. Often, the oral irrigator includes a fluid supply, such as a reservoir, that is fluidly connected by a pump to an oral irrigator tip. In oral irrigators that include a reservoir, the fluid must be refilled after a predetermined number of uses. Some oral irrigators include integrally formed reservoirs and to refill the reservoir the entire oral irrigator device may have to be moved into fluid communication with a water source (such as a user placing the oral irrigator beneath the faucet in a sink to refill the device). Other irrigators include removable reservoirs, but these typically come with removable lids that detach from a base along with the reservoir. These removable lids can become misplaced or damaged when taken off to refill the reservoir.

SUMMARY

One example may take the form of an oral irrigator including a base and a reservoir defining a fluid cavity removably connected to the base. The oral irrigator further includes a prow operably connected to the base and extending vertically upwards from the base. The prow may extend in a similar direction as one or more sidewalls of the reservoir. The oral irrigator further includes a lid rotatably connected to the prow. The lid rotates between first and second positions. In the first position the fluid cavity of the reservoir is exposed and in the second position the lid covers at least a portion of the fluid cavity.

Another example may take the form of an irrigating device. The irrigating device includes a handle operably and fluidly connected to an irrigating tip, a reservoir in fluid communication with the handle, a base operably connected to the reservoir and the handle, and a lid operably connected to the base. Removal of the reservoir from the base is independent of removal of the lid from the base. In other words, the lid remains operably connected to the base even if the reservoir is removed.

Yet another example may take the form of a countertop oral irrigator. The countertop oral irrigator includes a pump assembly, a housing enclosing the pump assembly, a reservoir removably positioned on a top surface of the housing, a prow extending upward from the housing and being substantially parallel to a first side of the reservoir and a lid rotatably connected to the prow. In an open position the lid uncovers the reservoir and in a closed poison the lid covers the reservoir.

While multiple examples are disclosed, still other examples of the present invention will become apparent to those skilled in the art from the following detailed description, which shows and describes illustrative examples of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 3 is an exploded view of the oral irrigator of FIG. 1A.

FIG. 5A is a front perspective view of the oral irrigator with select components hidden for clarity.

FIG. 10A is diagram of a first control signal produced by the massage mode module.

FIG. 10B is a diagram of a second control signal produced by the massage mode module.

FIG. 10C is a diagram of a third control signal produced by the massage mode module.

FIG. 19A is a bottom perspective view of a lid of the oral irrigator of FIG. 1A.

FIG. 19B is a front elevation view of the lid of FIG. 19A.

DETAILED DESCRIPTION OF THE INVENTION

Figure 1A:
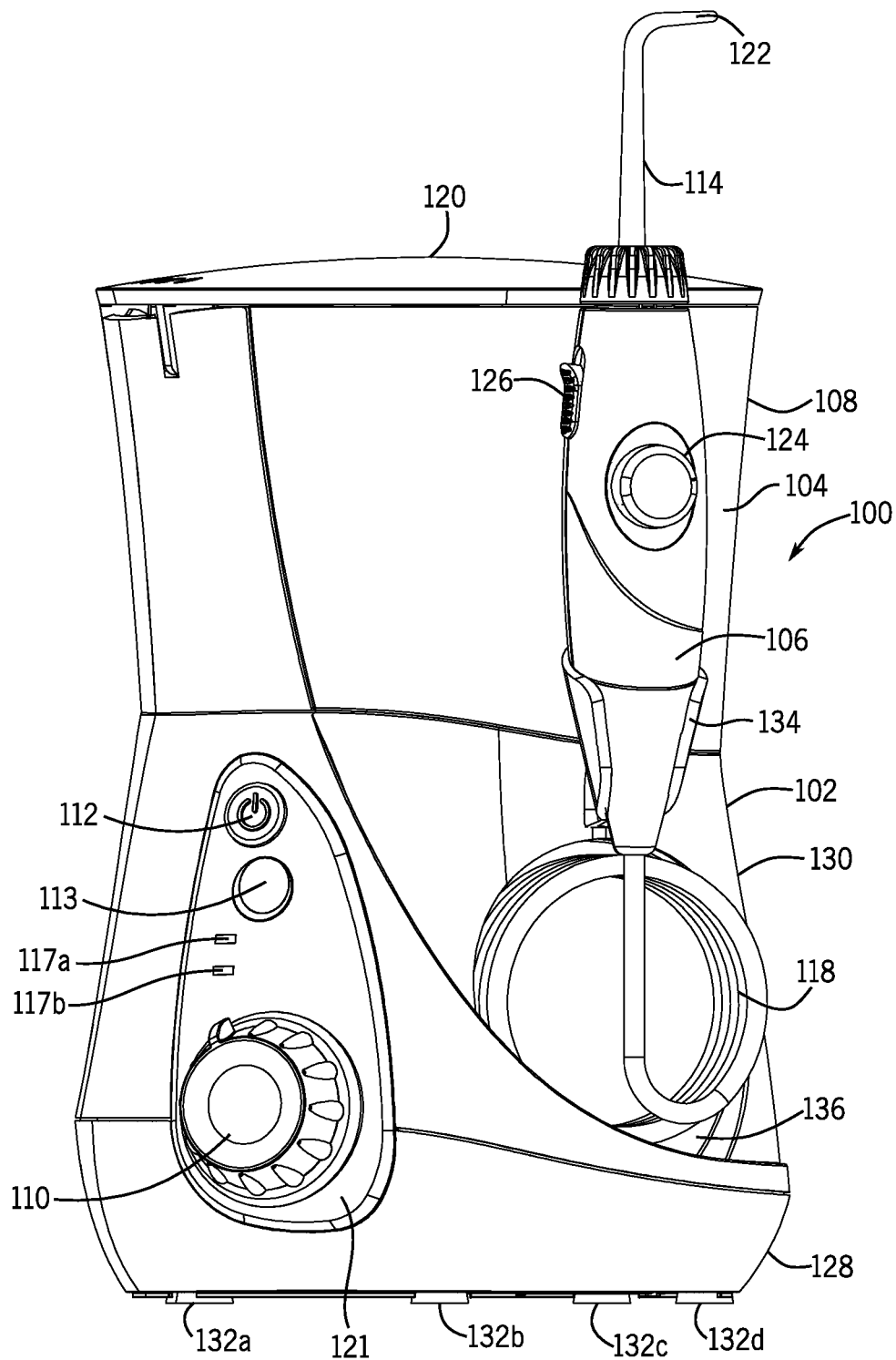
FIG. 1A is a front perspective view of an oral irrigator.

Some examples of the present disclosure include an irrigating device, such as an oral irrigator, having a massage mode module. The massage mode module is used to vary one or more characteristics of a fluid stream to create a fluid flow that massages a user's gums, as well as enhances a user's comfort as the user cleans his or her teeth or gums. The oral irrigator includes a motor and a pump connected to and controlled by the motor. The pump is fluidly connected to a fluid supply and pumps fluid from the supply to an outlet (such as a tip). The massage mode module may also be in communication with the motor and may provide one or more control signals to the motor to vary one or more characteristics of the motor, such as speed, power, or torque. Because the motor is connected to the pump, as the massage mode module varies the speed or other characteristics of the motor, the output characteristics of the pump may be correspondingly varied. The output characteristics of the pump may be varied based on a fluid flow that may "massage" a user's gums, such as a pulsed output whereby the fluid pulses (i.e., the flow intermittently turns on an off). In another example, the massage mode module may vary the outlet fluid pressure of the oral irrigator during massage mode, e.g., it may reduce the outlet pressure as compared to clean mode. In this example, the fluid pulse rate may remain substantially the same in both clean mode and massage mode or may also be varied along with the pressure.

In some examples, the oral irrigator may include a cleaning or normal mode and a massage mode. During the cleaning mode, the oral irrigator may include a relatively steady fluid flow or may include a fluid flow having a slight pulse (e.g., due to mechanical characteristics of the pump). During the massage mode, the massage mode module may vary the fluid pulse length and/or pressure. For example, the massage mode module may vary a control signal to selectively vary the power level provided the motor. In a specific implementation, the power may be selectively activated and deactivated, which may cause the motor to produce intermittent motion resulting in varying the output of the pump. The pump may be selectively activated to create a pulsating fluid flow through the oral irrigator outlet (e.g., the tip).

In one example, the pulses created by the massage mode module may be longer fluid pulse or breaks in the fluid stream as compared to the normal operation. The increase in pulse length causes the fluid stream to massage a user's gums, thereby enhancing blood flow and providing an enjoyable experience to the user. The pulses may be timed with capillary recovery of the gum tissues (i.e., timed to allow blood to flow back into the tissue between each fluid pulse), and provides therapeutic benefits to the gums.

The massage mode may vary one or more characteristics of the control signal based on user input. For example, the user may select the massage mode and may then vary the frequency, magnitude, or shape of the control signal, such as changing the shape of a voltage waveform or its frequency. In other examples, the massage mode may apply a predetermined signal to the motor. For example, a control signal may be determined for the massage mode and when the massage mode is activated by the user, the stored signal may be applied. In these examples, the massage mode module may include a plurality of control signals that may correlate to different massage modes. In yet other examples, the massage mode module may include stored signals that may be selected by a user for a predetermined pulsing effect and may vary one or more signals to allow the user to dynamically vary the pulsing effect.

In addition to providing a massage mode, the massage mode module or another processing element of the oral irrigator may vary one or more output characteristics of the oral irrigator to provide feedback to a user. As a first example, the massage mode may be activated automatically one or more times during normal mode to indicate to a user to move to a different tooth or portion of the mouth. As a second example, the massage mode may be activated after a predetermined time period in order to alert the user that a cleaning time (which may be set by the user or be preselected) has expired. As a third example, the massage mode may be activated automatically for certain time periods, e.g., for every 30 seconds of regular mode, the massage mode may be activated for a period of time to provide a massaging feel interspersed with cleaning.

In other examples, the massage mode module may be used with other irrigating devices. For example, the massage mode may be implemented in a nasal irrigator and may vary the fluid flow rate and pressure to massage the user's nasal tissues. In these examples, the pulse rate and control signal may be varied as compared to the oral irrigator, but may still provide a massaging effect.

In yet other examples, the massage mode module may be used with other oral instruments to provide a massaging effect and/or to enhance cleaning. For example, the massage mode module may be incorporated into an electrically driven toothbrush. In this example, the massage mode module may vary the motor speed or power to vary vibrations or bristle movement.

In addition to the massage mode, the oral irrigator also includes a removable reservoir with a lid operably connected to the base. In particular, the lid is attached via a prow to the base such that the reservoir can be removed from the base while the lid remains connected to the base. In other words, removal of the reservoir from the base is independent of removable of the lid from the base. In these embodiments, a user can open the lid to remove the reservoir while the lid remains secured to the base, which helps to prevent the lid from becoming misplaced or damaged when the reservoir is removed, such when it is removed to be refilled.

The lid may include one or more venting apertures. The venting apertures allow the reservoir to receive airflow so that air can circulate into the reservoir and storage compartments. For example, the venting apertures may be configured to enhance evaporation for a storage compartment, to allow accessories stored therein to dry, as well as to help any fluid leaks form the reservoir into the storage compartment to dry. The lid may further include one or more mechanisms, such as stops, that interact with the prow to limit rotation of the lid in one or more directions. These stops may be used to prevent the lid from rotating into the prow when the reservoir is removed from the base, which may help prevent damage to the lid and/or prow. Further, the rotational limits on the lid may be used to assist a user as he or she replaces the reservoir on the base after it has been removed as the lid may not have to be lifted by the user in order to fit the reservoir between the lid and the top surface of the base.

The oral irrigator may further include a storage compartment for receiving accessories, such as, but not limited to, tips or brushes for the handle. In one embodiment, the storage compartment is defined by a sidewall of the reservoir and a sidewall of the prow. In this embodiment, the prow may further include one or more accessory mounts that removably connect the accessories to the prow. As one example, the accessory mounts may be apertures that are similarly shaped and sized as a tip receiving aperture for the handle. In this manner, tips that connect to the handle can also connect to the prow. The storage compartment may be shielded by the prow and the reservoir to protect the accessories stored therein from debris and particles within the environment.

The oral irrigator may also include a drainage system to help fluids that leak from the reservoir or drip from the accessories to be drained out of the oral irrigator or be evaporated. As one example, the oral irrigator may include a drain channel defined in a top surface of the base that interfaces with the bottom of the reservoir. The drain channel is in fluid communication with a drain that allows fluid from the storage compartment and/or other areas of the base to drain out. The drainage systems helps to prevent fluid due to leaks, splashes, spills, or the like from pooling in certain areas of the base or storage compartment.

Overview of the Oral Irrigator

With reference now to the figures, the oral irrigator of the present disclosure will be discussed in more detail. FIGS. 1A-1D illustrate various views of an oral irrigator. With reference to FIGS. 1A-1E, the oral irrigator 100 may include a base 102, a prow 103 extending from the base, a removable reservoir 104, and a handle 106. The base 102 may provide support for the reservoir 104 and the handle 106, as well as house many of the drive and power assembly components of the oral irrigator 100. For example, the base 102 may house a pump, control circuitry, and/or motor, which will be discussed in more detail below.

The base 102 may include a lower base body 128 and an upper base body 130. The lower base body 128 forms a platform or tray that sits within the upper base body 130. The lower base body 128 provides support for one or more of the internal components of the oral irrigator 100 and the upper base body 130 encloses those components to conceal them, as well as provide protection for those components. The base 102 may include a plurality of feet 132a, 132b, 132c, and 132d to support the base 102 on a surface, such as a countertop or the like.

The base 102 may also include a clamp 134 or other structure to releasably support the handle 106. In some examples, the clamp 134 may be a C-clamp; however, other attachment mechanisms are envisioned. The base 102 may also include a hose cavity 136 or hose box that may receive and support the hose 118 in a collapsed position. Although not shown, in some examples, the hose cavity 136 may include one or more arms on which the hose 118 may be wrapped. The hose cavity 136 may be recessed into the upper base body 130, may be flush with the upper base body, or may extend outwards from the upper base body. In the embodiment shown in FIGS. 1A-1E, the hose cavity 136 may be defined by a removable back wall that is connected to the base 102 (see FIG. 3).

The oral irrigator 100 illustrated in FIGS. 1A-1E is a countertop irrigator. However, in some examples, the oral irrigator 100 may be a handheld irrigator. FIG. 2 is a front perspective view of a second example of an oral irrigator. With reference to FIG. 2, in examples where the oral irrigator 100 is a handheld unit, the reservoir 104 and handle 106 may be connected together. The reservoir 104 includes a removable cavity that can be filled by a user and then reattached to the handle 106. Additionally, in these examples, the internal components of the irrigator 100, such as the motor, pump, and control circuitry, may be included within the handle 106 rather than a base unit. The description of the oral irrigation described below is generally directed to the oral irrigator illustrated in FIGS. 1A-1E; however, it should be noted that the description is equally applicable to the oral irrigator 100 shown in FIG. 2, with the exception that the internal components of the base are included in the handle 106.

With reference again to FIGS. 1A-1E, the oral irrigator 102 includes a lid 120 for the reservoir 104. The lid 120 is operably connected to the base 104 via the prow 103, and is rotatable relative thereto. The lid 120 covers the reservoir 104 when the reservoir 104 is connected to the base 102. The reservoir 102 is removable from the base 104 allowing the reservoir to be refilled. The reservoir 104 may be substantially any size or shape and may be modified as desired, for example, as shown in FIG. 2 the reservoir is included as a cavity attached to the handle. The reservoir will be discussed in more detail below with respect to FIGS. 17 and 18.

Figure 2:
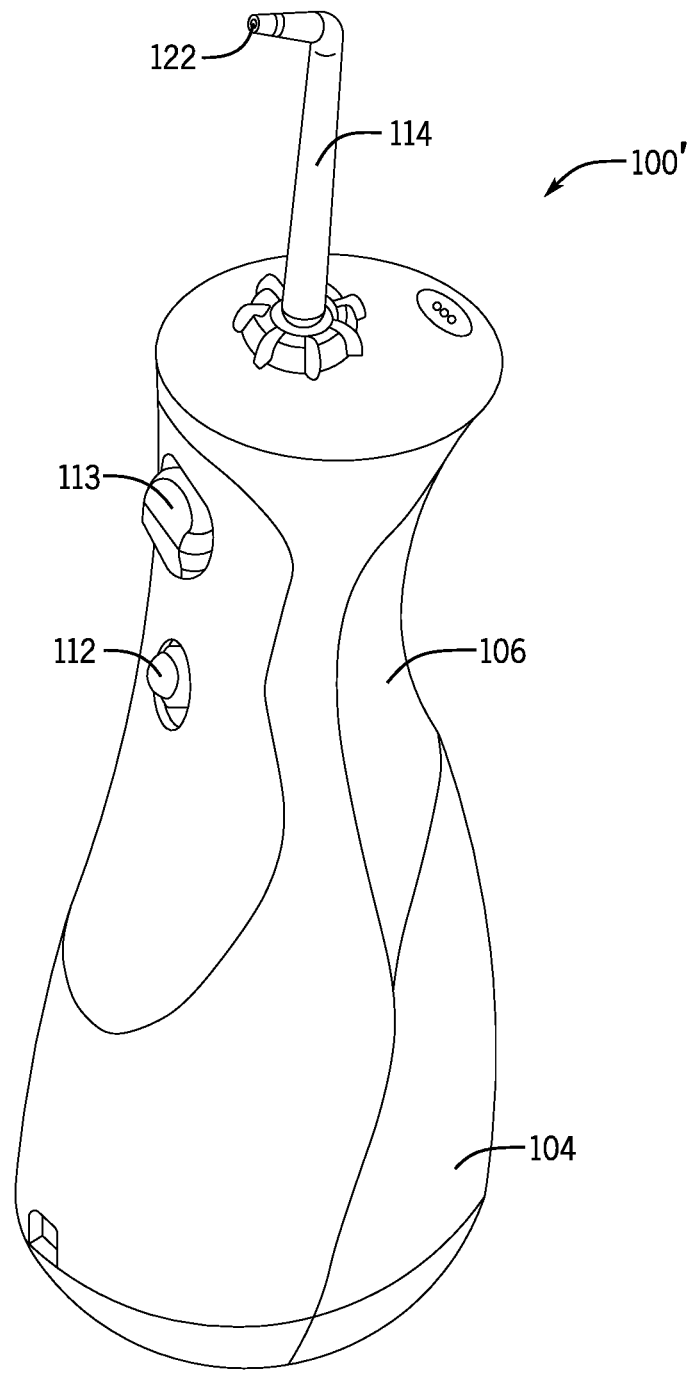
FIG. 2 is a front perspective view of a second example of an oral irrigator including a massage mode.
Figure 4A:
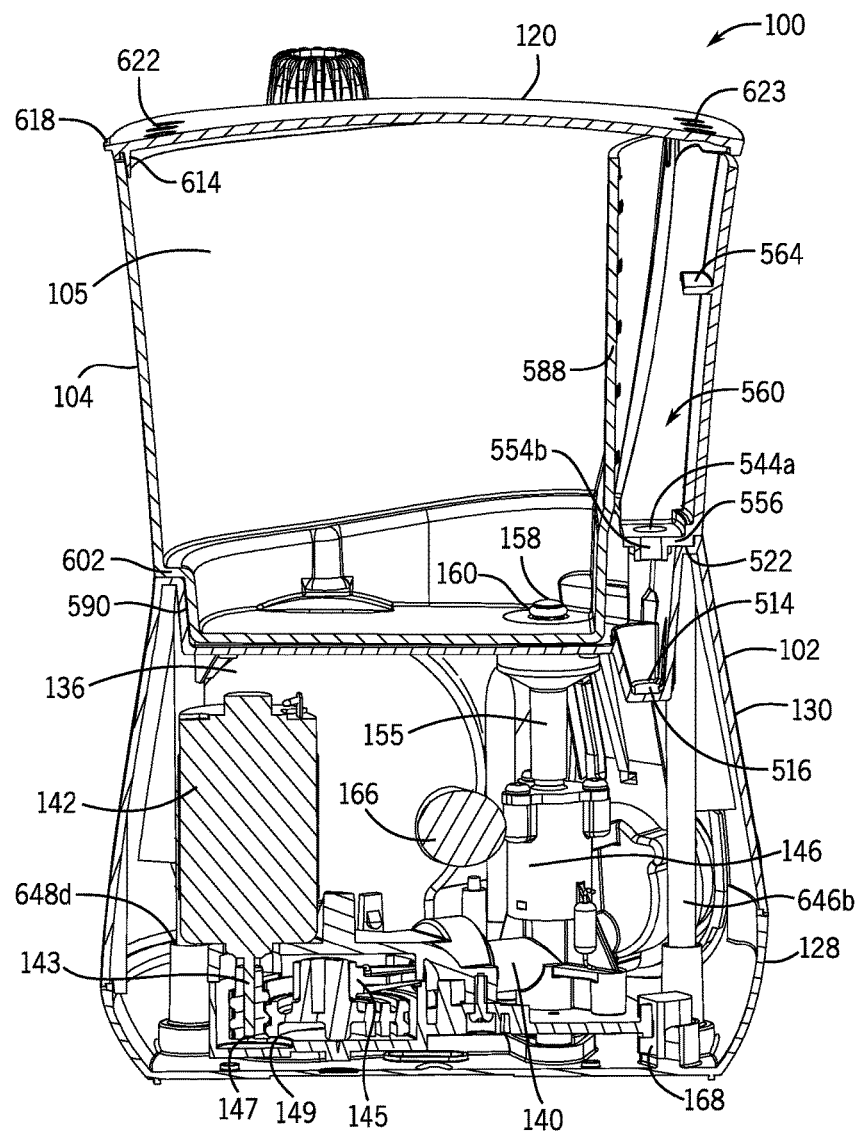
FIG. 4A is cross-section view of the oral irrigator taken along line 4A-4A in FIG. 1B.
Figure 4B:
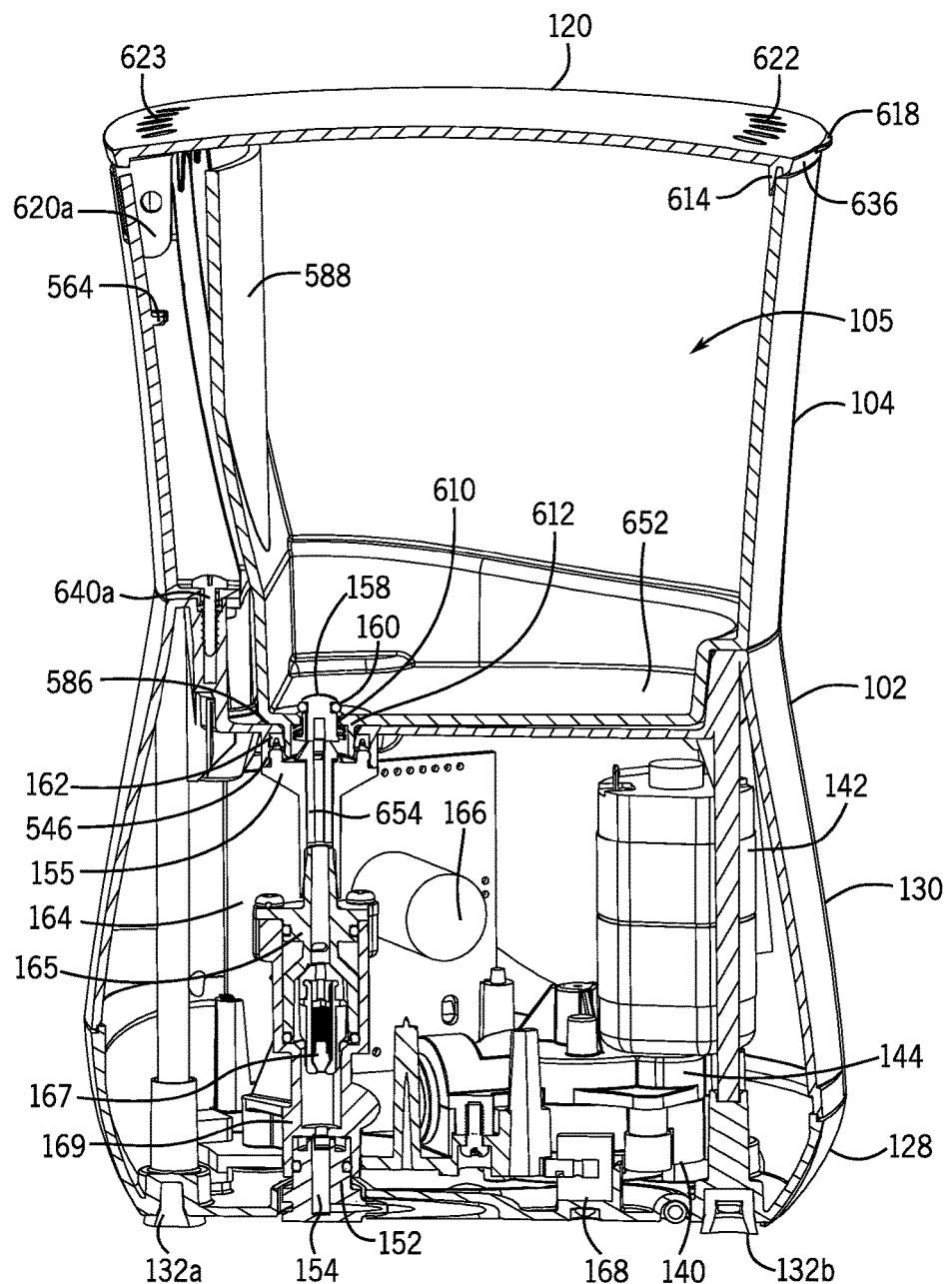
FIG. 4B is a cross-section view of the oral irrigator taken along line 4B-4B in FIG. 1A.

FIG. 3 is an exploded view of the oral irrigator of FIG. 1A. FIGS. 4A, 4B, and 4C are cross-section views of the oral irrigator taken alone lines 4A-4A, 4B-4B, and 4C-4C, respectively, in FIG. 10. With reference to FIGS. 4A-4C, the reservoir 104 defines a cavity 105 to hold liquid that may be expelled trough a tip 114 connected to the handle 106.

With reference again to FIGS. 1A-1E, the handle 106 is removable from the base 102 and is in fluid communication with the reservoir 104. For example, a hose 118 is fluidly connected to the reservoir 104 via a hose connector 125, which allows the hose 118 to fluidly connect the reservoir 104 to the handle 106 and tip 114. In examples where the reservoir 104 may be incorporated into the handle 106, the hose 118 may be internal to the handle 106 or may be omitted (e.g., a fluid pathway may be defined through a housing of the handle rather than a tube). In some examples, the handle 106 may include a plurality of internal components, such as a check valves, bypass valves, pause buttons, or the like. In these examples, the handle 106 may be used to vary one or more characteristics of the fluid flow output by the tip, separate from or in addition with the features for controlling the fluid output within the base. As mentioned above, although a number of components, such as the pump, reservoir, etc., are discussed herein as being incorporated into the base, in certain examples these components may be included with the handle. For example, as shown in FIG. 2, a handheld oral irrigator may include a portable reservoir attached to the handle with a pump internal the handle. Accordingly, the discussion of any particular example for the handle and base is meant as illustrative only.

The tip 114 is selectively removable from the handle 106. For example, an eject button 126 can selectively release the tip 144 from the handle 106. The tip 114 defines a fluid pathway that is fluidly connected to the hose 118. The tip 114 includes an outlet 122 from which fluid from the reservoir 104 is expelled into a user's mouth from the oral irrigator 100. The tip 114 generally is configured to be inserted into a user's mouth and to expel fluid against a user's teeth, gums, tongue, etc. In some examples, the outlet 122 portion of the tip 144 may be shaped as a nozzle or may include a nozzle or other attachment connected thereto. Although a tip 114 is shown, in other embodiments, the oral irrigator may include other accessories, such as a brush head, a nozzle with one or more bristles or cleaning elements, or the like. Accordingly, the discussion of the tip as an outlet for the oral irrigator 100 is meant as illustrative only.

Initially, the electrical components and pumping assembly of the oral irrigator will be discussed and then the structural components and mechanical features of the oral irrigator will be discussed. In particular, the structural features and interconnections between the base 102, reservoir 104, and prow 103 will be discussed in further detail below with respect to FIGS. 13A-22B.

Pump Assembly and Electrical Components

Figure 1B:
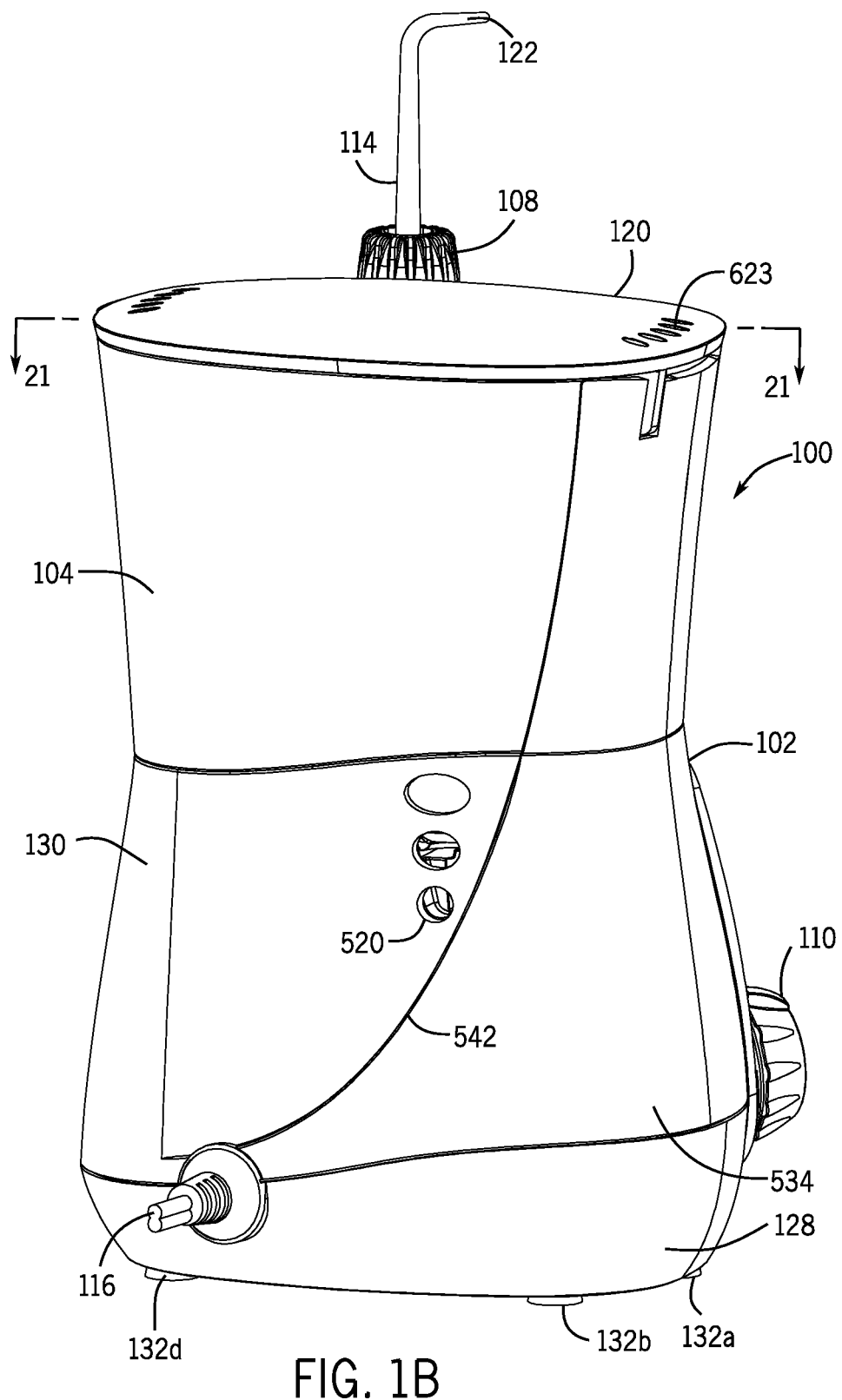
FIG. 1B is a rear perspective view of the oral irrigator of FIG. 1A.

The oral irrigator 100 includes a pump assembly 119 to control fluid flow between the reservoir 104 and tip 114. The pump assembly 119 includes one or more pumping elements, valve elements, and control elements. For example, the pump assembly may include a plurality of control actuators 110, 112, 113, 124 to control one or more characteristics or parameters of the oral irrigator 100. For example, the control actuators 110, 112, 113, 124 can be used to activate and/or deactivate the oral irrigator 100, vary a flow rate, fluid pressure, and/or activate a particular mode, e.g., massage mode or cleaning mode. The number of control actuators 110, 112, 113, 124, as well as their structure, size, and shape may be varied as desired. For example, as shown in FIGS. 1A and 1B, the two control actuators 110, 112, 113 on the base 102 are illustrated as rotatable knob or buttons; however, in other examples, the control actuators 110, 112, 113, 124 may be switches, sliders, or the like.

A first control actuator 110 may be configured to vary a fluid pressure of fluid as it exits the tip 114. For example, the control actuator 110 may be operably connected to a valve assembly within a pump 146 that selectively changes the diameter and/or length of the fluid pathway between reservoir 104 and the tip 114. As the pathway changes, such as due to a user turning the control actuator 110, the outlet fluid pressure as fluid is expelled from the tip 114 may be selectively modified. As another example, the first control actuator 110 may activate a massage mode module to activate a massage mode for the oral irrigator 100.

A second control actuator 112 may be configured to selectively power the oral irrigator 100. The second control actuator 112 may be a power button or knob to turn the oral irrigator 100 on and off. Additionally, in some examples, the second control actuator 112 may be used to activate one or more settings. As an example, the second control actuator 112 can activate and deactivate the oral irrigator 100, as well as select one or more settings, such as a massage mode, low pressure, high pressure, or the like.

A third control actuator 113 may be configured to selectively activate a massage mode. In some examples the third control actuator 113 is positioned adjacent to the second control actuator 112 and is a compressible button, rather than a knob. However, in other examples, the control actuator 113 may be a knob, switch, or other input element. Additionally, although the control actuator 113 is shown as being on a control face plate 121 of the base 102, in other embodiments it may be located on the handle 106 or other portions of the base 102.

As shown in FIG. 1A, in some embodiments, three of the control actuators 110, 112, 113 are positioned on the control face plate 121 of the base 102. This allows a user easy access to control various parameters of the oral irrigator.

In some examples, a fourth control actuator 124 may be disposed on the handle 106. The fourth control actuator 124 is used to selectively activate one or more settings or pause the oral irrigator 100. By placing the control actuator 124 on the handle 106, the user may more easily change settings or pause the oral irrigator 100 while he or she is using the oral irrigator 100.

The various control actuators 110, 112, 113, 124 may be configured as desired and may change one or more settings or parameters of the oral irrigator 100. For example, any of the buttons 110, 112, 113, 124 may be configured to activate a massage mode for the oral irrigator 100. Therefore, although the control actuators have been discussed with activating or controlling select parameters, the parameters controlled by each can be varied as desired.

The oral irrigator 100 may also include a plurality of indicators 117a, 117b that provide feedback to a user. For example, the indicators 117a, 117b may be one or more light emitting diodes (LEDs) that illuminate, change color, and/or pulse to indicate the current mode, pressure level, or the like. In a specific example, a first indicator 117a is illuminated during normal mode and a second indicator 117b is illuminated during massage mode. See, for example, FIG. 8D. Additionally, in some examples, the oral irrigator 100 may include one or more feedback components.

With reference to FIG. 1B, the pump assembly 119 includes a power cable 116. The power cable 116 is configured to be placed in electrical communication with a power source, such as a wall outlet, to transfer power from the power source to the pump assembly 119 and other components of the oral irrigator 100 requiring power. It should be noted that the type of power cable 116 might be varied based on the power source for the oral irrigator 100. Alternatively in other embodiments, such as the oral irrigator shown in FIG. 2, the oral irrigator 100' includes an integrated power supply, such as one or more batteries. In these cases the power cord 116 may be omitted or may be used to recharge the integrated power supply (rather than directly provide power to the oral irrigator 100 as in the embodiment of FIGS. 1A-1E).

Figure 5B:
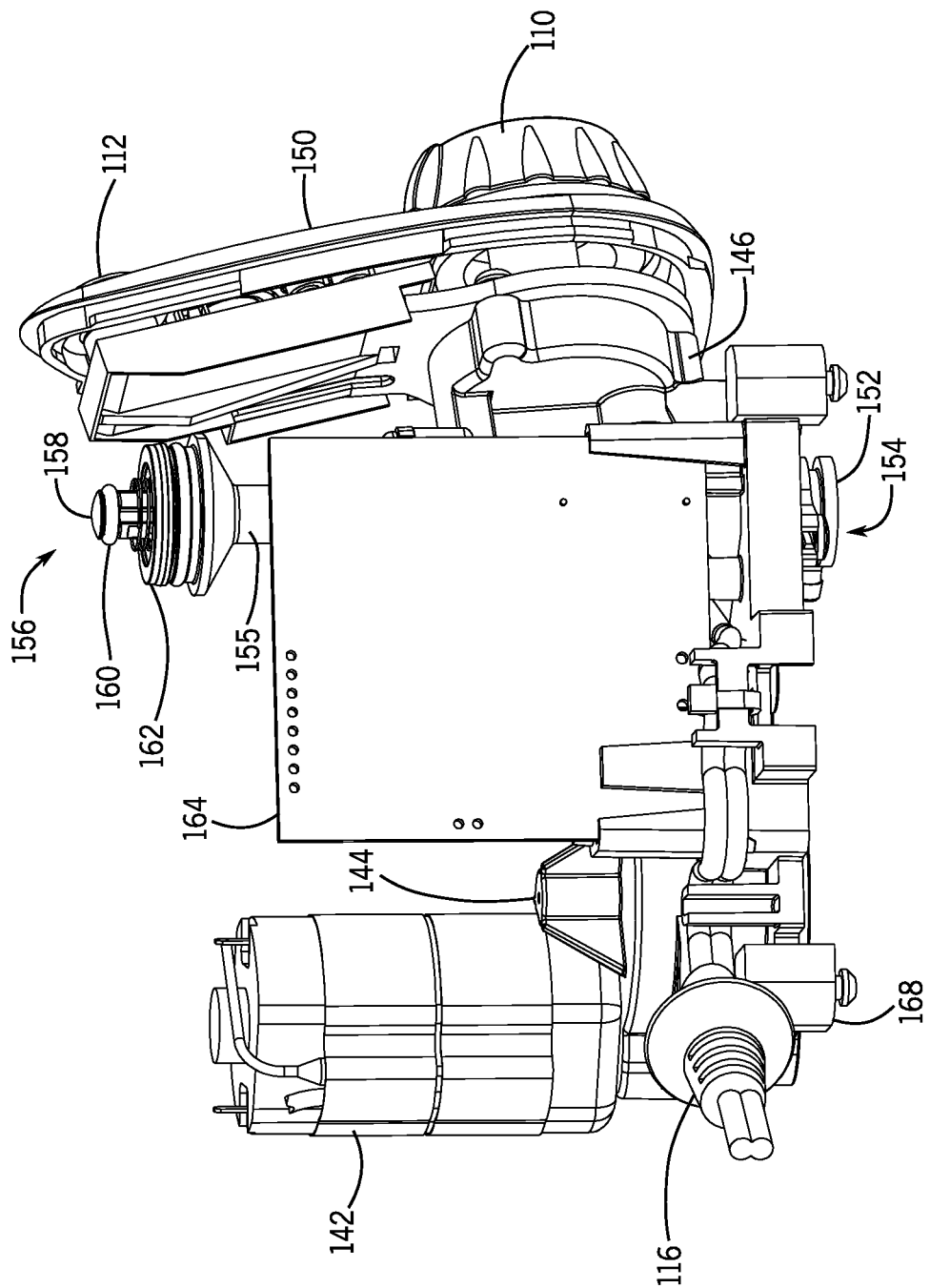
FIG. 5B is a rear perspective view of the oral irrigator with select components hidden for clarity.
Figure 5C:
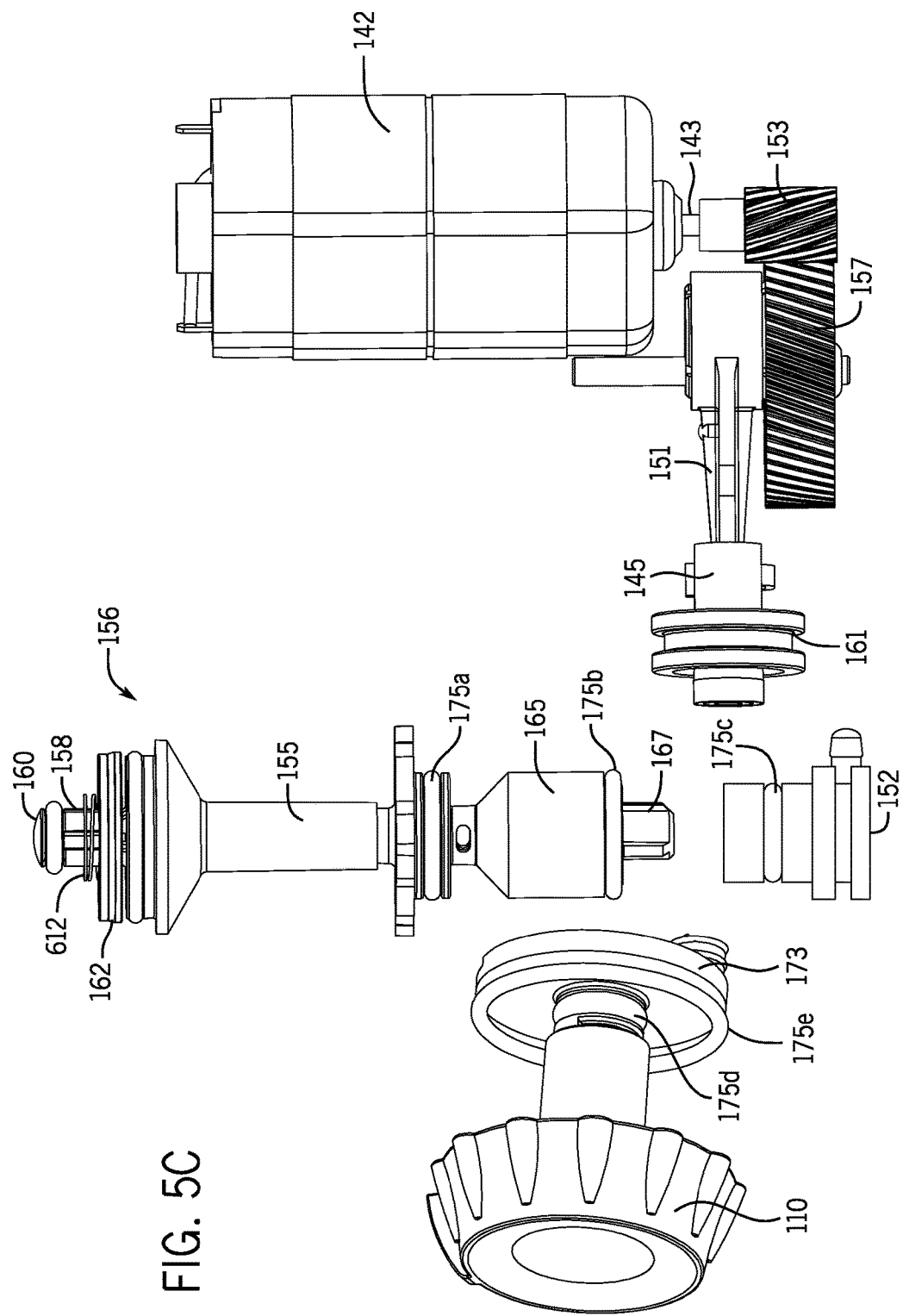
FIG. 5C is a front perspective view of the pump assembly illustrated in FIG. 5A but with the pump body hidden for clarity.

Additional components of the pump assembly 119 will now be discussed. FIGS. 5A and 5B are various views of the oral irrigator pump assembly 119. FIG. 5C is a view similar to FIGS. 5A and 5B but with the gear box and pump body hidden for clarity. With reference to FIGS. 5A-5C, the pump assembly 119 includes a motor 142, a gear box 144, a pump 146, and a chassis 140 supporting the motor 142, gear box 144 and pump 146. A valve assembly 156 including a valve 158 and valve body 155 fluidly connects the reservoir 104 to the pump 146 and a valve fitting 152 fluidly connects the pump 146 to the hose 118 (and thus the tip 114 and handle 106). Additionally, a check valve 167 (see FIG. 4B) and a valve bypass 173 may be positioned between the valve assembly 156 and the valve fitting 152. The check valve 167 and valve bypass 173 acts to regulate fluid pressure of flow between the pump 146 and the tip 114. The pump assembly 119 also includes control circuitry 164 having a signal generator 166 in electrical communication with the motor 142. It should be noted that the pump assembly 119 may include a plurality of sealing members 175a, 175b, 175c, 175d, 175e, such as O-rings or seal cups, positioned at the interconnections between the various elements.

With reference to FIGS. 4A and 5A, the motor 142 is substantially any type of electromechanical device that can drive movement or create mechanical work sufficient to drive the pump 146. For example, the motor 142 may be a direct current motor where the speed of the motor 142 is controlled by a signal, such as a voltage signal. Control of the motor 142 will be discussed in more detail below.

The motor 142 includes a drive shaft 143 (see FIGS. 4A and 5C) that is connected to a pinion gear 153, driven gear 157, a connecting rod 151 and piston 145. The gear box 144 covers the gear shaft 147, the drive gear 149, and other mechanical gears and/or linkage elements that may be used to connect the drive shaft 143 of the motor 144 to the pump 146. The linkage and gear elements, such as the pinion gear 153 and driven gear 157 may be varied as desired and generally depend on the orientation of the motor 142 and the pump 146 relative to one another, the size or speed of the motor, and the like. In one example, the pinion gear 153 and driven gear 157 may both be helical gears. The helical shape of the gears help to reduce noise from the pump as the load transmitted between the pinion gear and the driven gear is distributed over the length of the helical teeth, which reduces the noise. A pump seal 161 may be received around the piston 145 to seal the piston against the inner walls of the pump 146 and gear box 144.

The pump 146 may be substantially any component that forces fluid from one location to another. For example, as shown in FIGS. 4A-5C, the pump 146 may be a piston driven pump that selectively forces fluid from the reservoir 104 into the hose 118. However, many other pump types are envisioned. Some illustrative pump types include a diaphragm pump or a centrifugal pump. With reference to FIG. 4B, the pump 146 includes a pump body 169 and an inlet pump 165 received within the pump body 169. The first control actuator 110 is operably connected to the pump 146 and may be attached to a bypass valve or other control valve (not shown), which as discussed briefly above, can be used to selectively vary the pressure of fluid output from the pump 146 and may do so by varying the diameter of a fluid channel between the pump 146 and the tip 114.

Figure 6:
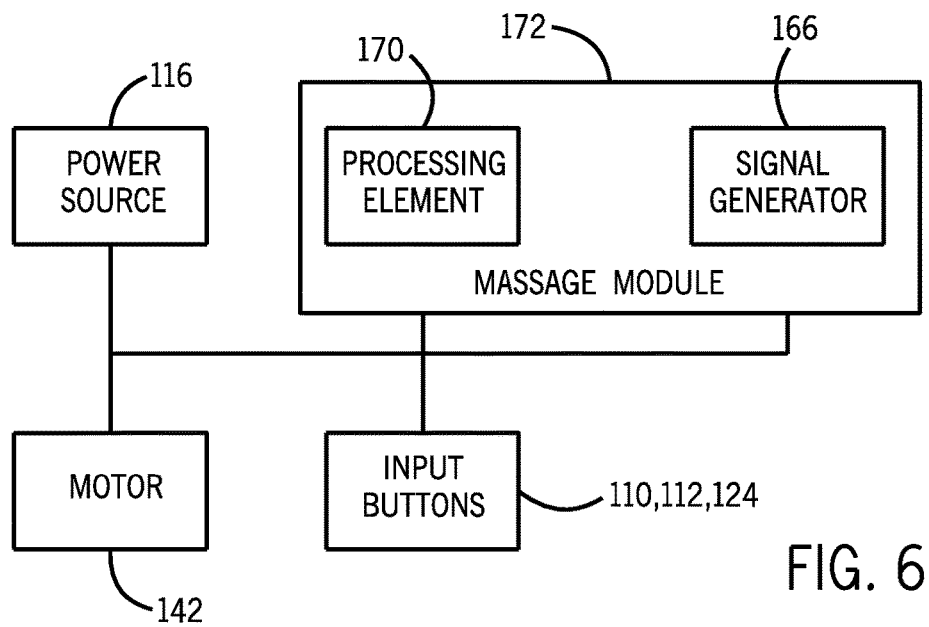
FIG. 6 is a simplified block diagram of the electrical components of the oral irrigator.

The control circuit 164 controls one or more elements of the pump assembly 119. As one example, the control circuit 164 controls the motor 142 and other elements of the oral irrigator 100. FIG. 6 is a simplified block diagram of the pump assembly 119 illustrating the electrical communication between select components. With reference to FIGS. 4A and 6, a power source 115 (which may be an outlet in communication via the power cable 116 or one or more batteries) is in communication with a massage mode module 172, the motor 142, and optionally, one or more of the input buttons 110, 112, 113, 124. For example, the second control actuator 112 may be in communication with a switch 148 module is in communication with control circuitry 164 and/or power source 115 to selectively activate the motor 142.

In some examples, with reference to FIGS. 5A and 6, the control circuitry 164 provides a substrate that supports one or more components, as well as provides communication between those components. For example, the control circuit 164 may be a printed circuit board including one or more traces or connective lines that transmit signals between the massage mode module 172, the motor 142, and/or the power source 115.

The massage mode module 172 selectively controls the motor 142 to vary one or more parameters of oral irrigator 100. The massage mode module 172 includes a signal generator 166 as well as one or more processing elements 170. The processing element 170 may include one or more processors or control chips that process and execute instructions. The signal generator 166 is substantially any type of component that creates voltage signals to control one or more characteristics of the motor 142. For example, the signal generator 166 may create one or more repeating or non-repeating electronic signals (e.g., voltage waveforms) that are applied to the motor 142. In a particular implementation, the signal generator 166 may be a function generator produces electrical waveforms over a range of frequencies. Exemplary waveforms include sinusoidal waves, square waves, sawtooth waves, triangular waves, and so on. Additionally, the signal generator 166 may be configured to create modified waves that include characteristics of two or more waveforms (i.e., combination waves). Illustrative waveforms that may be used will be discussed in more detail below with respect to FIGS. 9A-9C.

Figure 7:
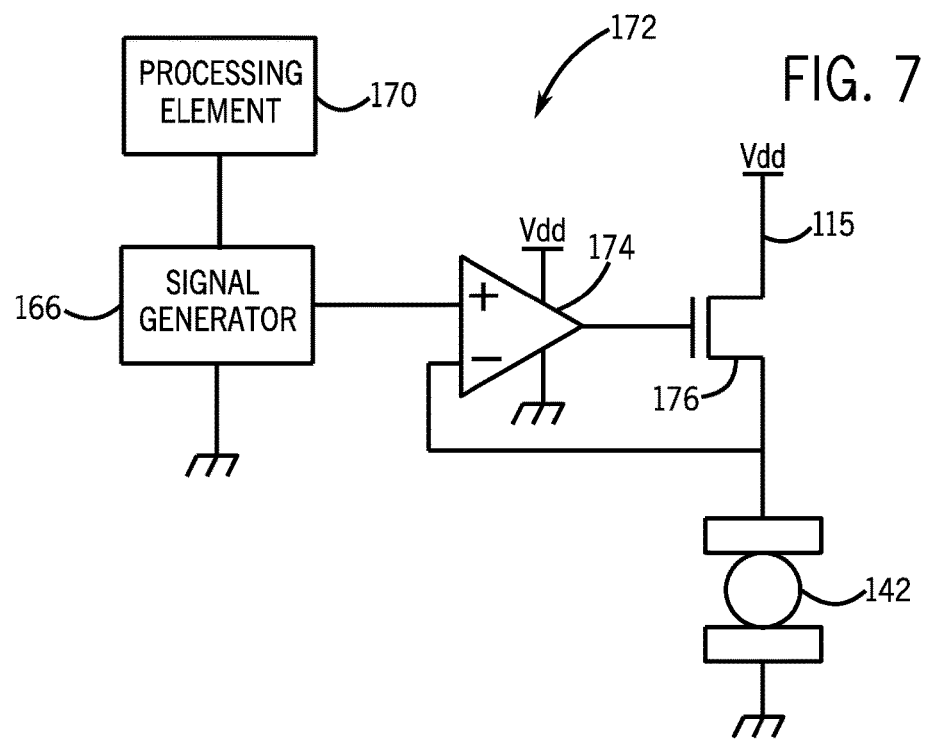
FIG. 7 is a simplified circuit diagram for a massage mode module.

FIG. 7 is a simplified circuit diagram of the massage mode module 172. With reference to FIGS. 6 and 7, the signal generator 166 may be in communication with an amplifier 174 and a gate 176 or switch. The signal generator 166 may be in communication with the processor element 170, which determines the signals generated by the signal generator 166. In some examples, the signal generator 166 is incorporated into the processing element 170, such that the processing element 170 performs the functions of the signal generator 166 to create and apply signals to the motor 146.

The amplifier 174 amplifies the signals generated by the signal generator 166 prior to applying the signal to the motor 146. For example, the amplifier 174 may be an operational amplifier or a differential amplifier. The amplifier 174 may be in communication with the motor 142 as well as the signal generator 166. In some examples, the amplifier 174 may be configured to receive feedback from its output to provide a more consistent output signal. However, it should be noted that the configuration of the amplifier 174, as well as the type of amplifier and inputs used may be varied based on the type of motor 142 and signal generator used 166. Additionally, depending on the output voltage of the signal generator 166 and/or other system characteristics, the amplifier 174 may be omitted. In these instances, the signal may be directly or indirectly applied to the motor without being amplified.

The amplifier 174 may be in communication with a gate 176 or switch. The gate 176 selectively provides the output of the amplifier 174 to the motor 142. For example, when the gate 176 is deactivated, the motor 142 may not receive a signal from the signal generator 166, but instead may receive a constant power signal. As another example, when the gate 176 is deactivated, the motor 142 is isolated from any signal or power source, preventing the motor 146 from being activated. In this example, the gate 176 provides power to the motor 146 and the signal produced by the signal generator 166 varies the signal transmitted through the gate 176. Continuing with this example, during normal mode the motor 146 receives a constant voltage signal and during massage mode the motor 146 receives a variable signal. As yet another example, the activation voltage for the gate 176 can be varied to control the current transmission to the motor 146. In particular, in examples where the gate 176 is a transistor, the gate 176 may be slightly activated during one mode allowing a reduced amount of current to travel between its source and drain and then may be fully activated to allow full current flow. The variation in current may be used to pulse the signal to the motor or may be used to slow the motor down.

The gate 176 may be a switch or other selectively activated component. In one example, the gate 176 may be a transistor, such as a metal-oxide-semiconductor field-effect transistor (MOSFET), such as an N-channel MOSFET. However, other types of transistors or gates are also envisioned, as well as other components that may be used to selectively provide communication between two or more components.

The massage mode module 172 and other control circuitry of the oral irrigator may be implemented in a number of different manners, which may vary as desired. FIGS. 8A-8D illustrate various circuit schematics that may be used to implement one or more functions of the oral irrigator 100, pump assembly 119, control circuitry 164, and/or massage mode module 172. However, it should be noted that the electrical components, such as resistors, capacitors, and/or gates illustrated may be otherwise configured, omitted, or varied based on a number of a different factors. As such, the schematics illustrated in FIGS. 8A-8D are meant as illustrative and not limiting.

Figure 8A:
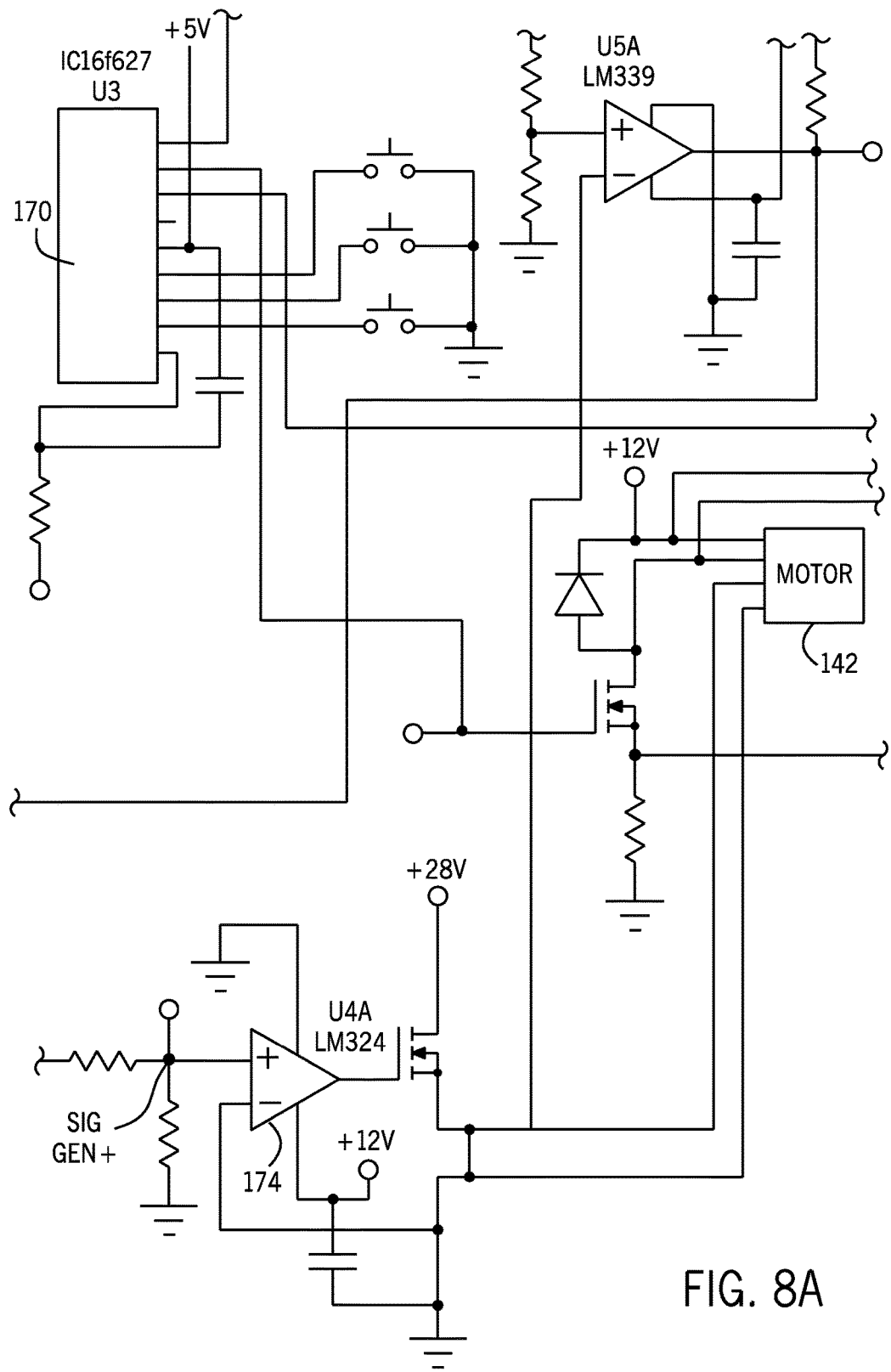
FIG. 8A is a first example of an illustrative circuit schematic for an implementation of the electrical components of the oral irrigator.

FIG. 8A is an illustrative circuit schematic of the control circuitry for one example of the oral irrigator. With reference to FIG. 8A, the circuitry 164 may include a number of electrical components, such as traces, resistors, switches or transistors, and amplifier. The schematic illustrated in FIG. 8A is one example only and the exact components and structures for implementing the massage mode module may be varied as desired and based on the constraints and parameters of the particular oral irrigator or other device incorporating the massage mode module.

Figure 8B:
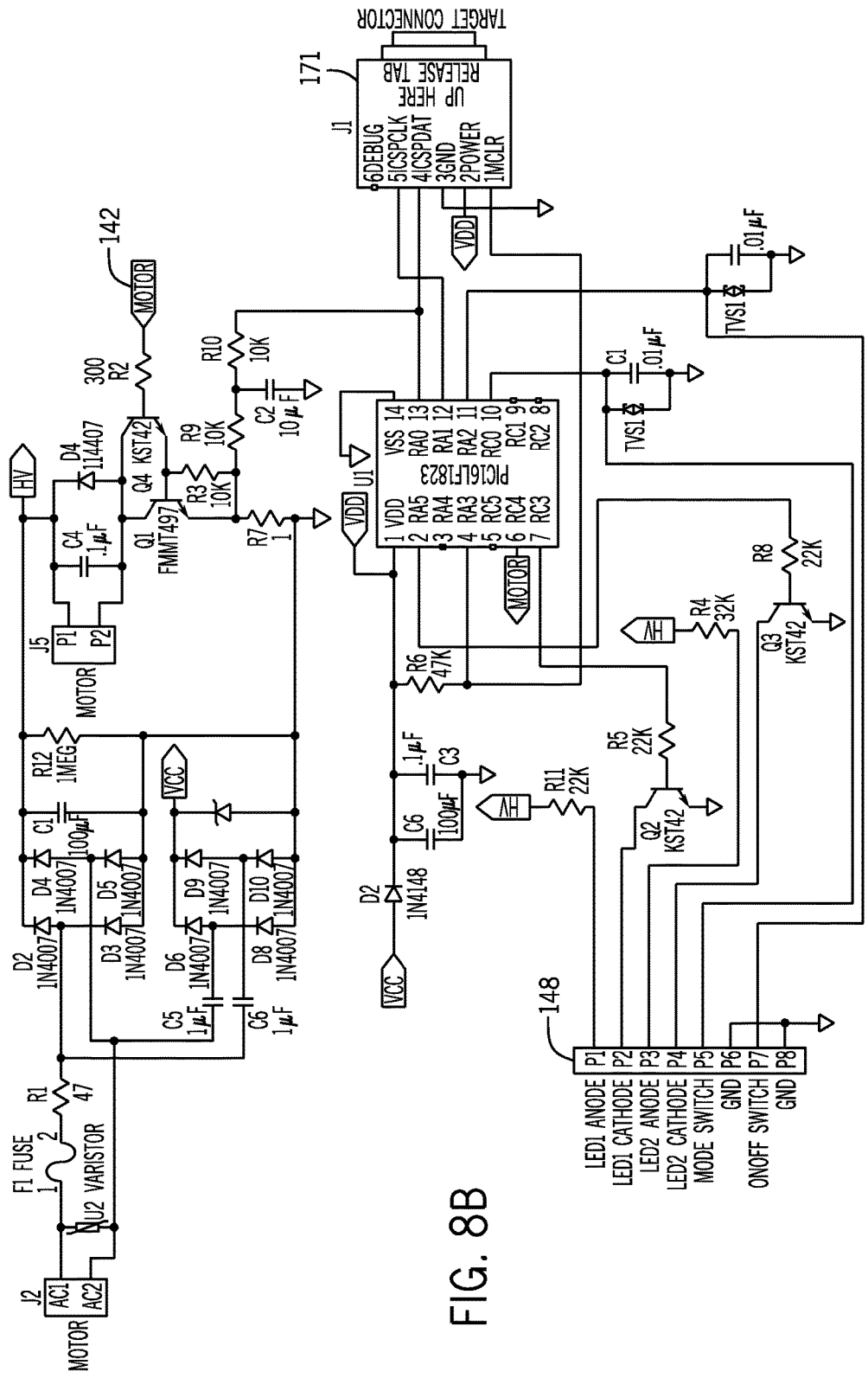
FIG. 8B is a second example of an illustrative circuit schematic for an implementation of the electrical components of the oral irrigator.

FIG. 8B illustrates a second example of a schematic for the oral irrigator. In the example shown in FIG. 8B, the power source for the pump assembly 119 may be 12V. The schematic may also include a second control element 171 that controls one or more of a clock signal, data, a reset function, and the like for the oral irrigator. The second control element 171 may be in electrical communication with the processing element 170.

Figure 8C:
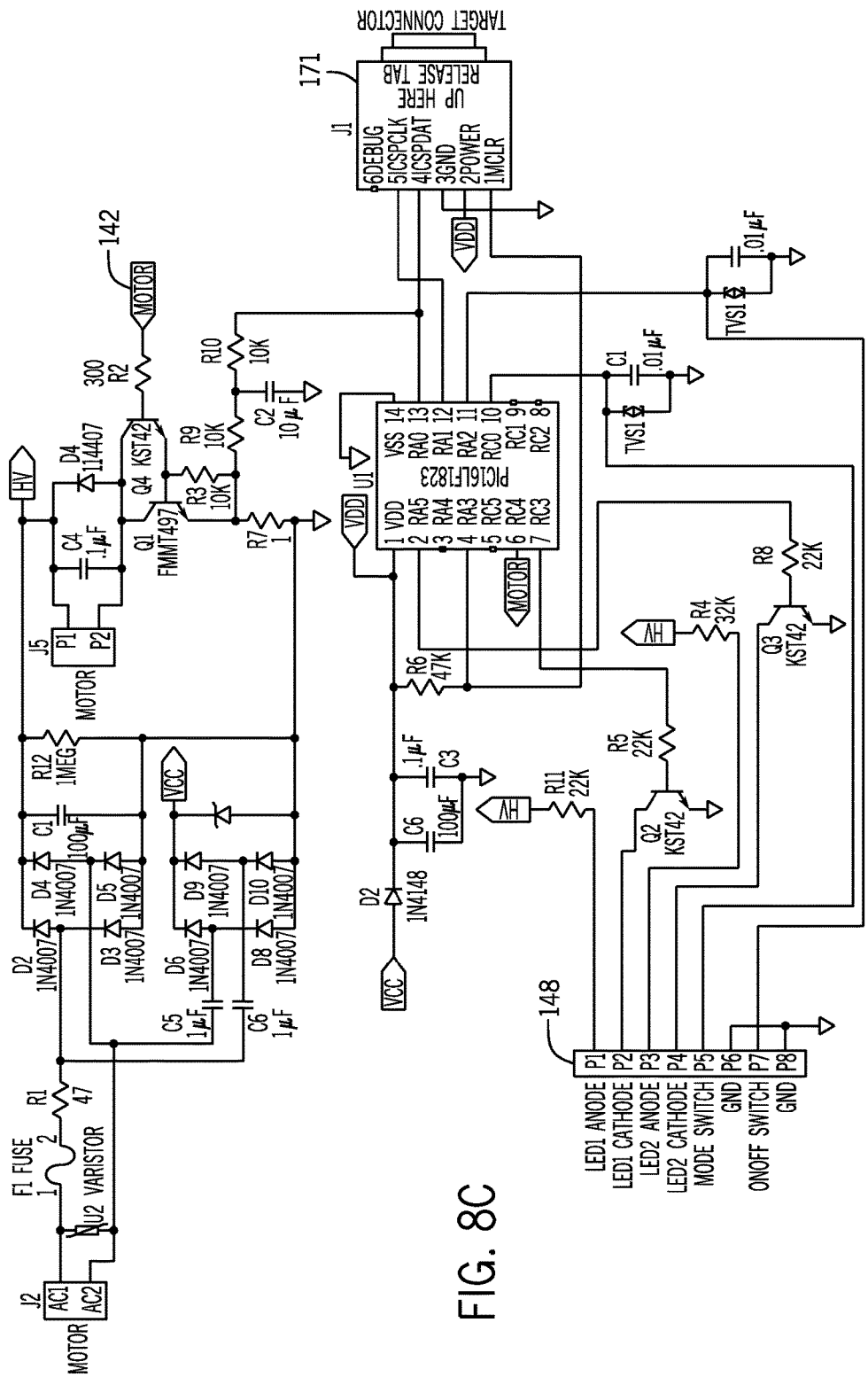
FIG. 8C is a third example of an illustrative circuit schematic for an implementation of the electrical components of the oral irrigator.

FIG. 8C illustrates a third example of a schematic for the oral irrigator. In the example shown in FIG. 8C, the voltage source may be higher than the example shown in FIG. 8B and may include a fuse 181 to help regulate spikes in current and/or voltage. As shown in FIG. 8B, the second control element 171 may also be used to provide clock signals and resets for the oral irrigator 100 and the switch 148 may provide communication between one or more of the control actuators 110, 112, 113, 124 with the processing element 170.

Figure 8D:
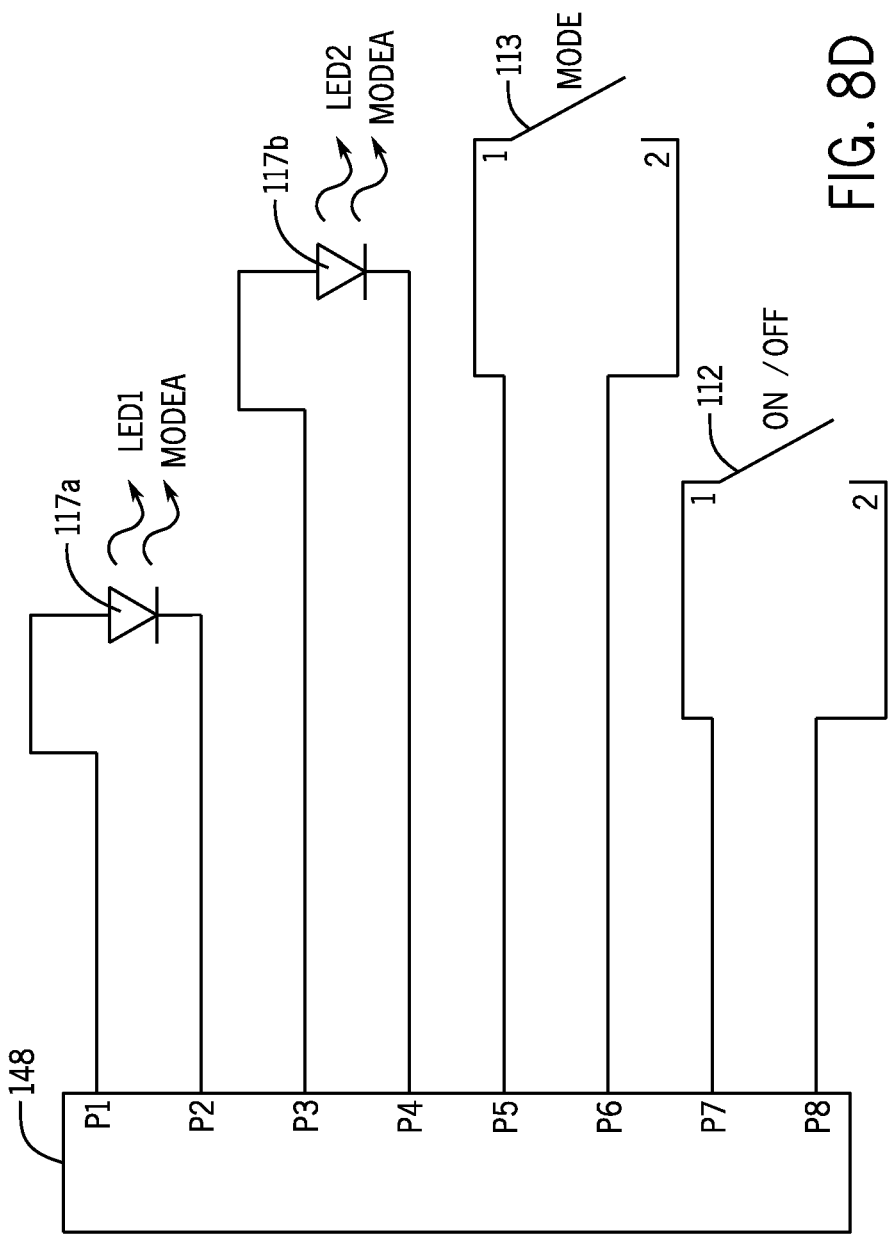
FIG. 8D is an example of a switch control board for the oral irrigator.

FIG. 8D illustrates a diagram of the switch 148 and light module. With reference to FIGS. 8B, 8C, and 8D, the switch 148 module may be in communication with the processing element 170, the lights 117a, 117b, the second control actuator 112, and the third control actuator 113. With reference to FIG. 8D, when the second control actuator 112 is activated by the user, the switch 148 provides a signal to the processing element 170, activates the oral irrigator 100. Additionally, the switch 148 may activate the first light 117a to indicate that the oral irrigator 100 has been turned on and is in the normal mode. For example, the normal or clean mode may be a default mode that may be activated when the oral irrigator 100 is initially activated.

With continued reference to FIGS. 8B-8D, when the second control actuator 113 is activated by the user, the switch 148 provides a signal to the processing element 170 indicating that the user has activate the massage mode or second mode. Additionally, the switch 148 may illuminate the second light 117b to indicate to the user that the massage mode has been activated. In the example shown in FIG. 8D, both lights 117a, 117b may be LEDs. However, in other embodiments, other light sources are envisioned.

Massage Mode Operation

With reference again to FIGS. 1A-7, in operation, the user may rotate, push, or otherwise provide an input to the second control actuator 112. The second control actuator 112 may activate the oral irrigator 100, causing the power supply 115 to provide power to the control circuitry 164 and the motor 142. During normal operation, control circuitry 164 provides a normal control signal to the motor 142. For example, the voltage or power source 115 is placed into communication with the motor 142 and provides a substantially constant control signal to the motor 142. As the motor 142 receives the constant control signal, the motor 142 turns the drive shaft 143, moving the piston 145. As the piston moves, fluid from the reservoir 104 is pulled through the valve 158 into the pump 146 and pushed through the outlet 154 of the valve fitting 152 into the hose 118. The fluid travels through the hose 118 to the handle 106 and exit out of the tip 114.

During normal operation, the control signal to the motor 142 may be substantially constant, causing the motor 142 to rotate the drive shaft 143 in a substantially constant manner (e.g., having a constant velocity). In examples where a piston pump or other reciprocating pump is used, the fluid may be slightly pulsed as it is expelled from the tip 114. This is due to the reciprocating nature of the pump, e.g., the alternating pulling and pushing to alternately pull fluid from the reservoir 104 and push fluid from the pump out to the tip 114. Depending on the type, size, or the like, the pulses during normal operation may have a somewhat short duration and fast frequency. In one example, the pulses due to the reciprocating nature of the pump 146 may be about 26 pulses per second. However, in other examples, e.g., during normal mode, the fluid outlet may not be pulsed, but may be substantially constant. For example, in examples where a non-reciprocating pump is used, the output during normal mode may be substantially constant.

During use, if the user hits the pause actuator 124, a valve within the handle 106 may reduce or substantially prevent fluid from exiting the tip 114. Alternatively or additionally, the fourth control actuator 124 may transmit a signal to the processing element 170 that may temporarily stop movement of the motor 142, to prevent or reduce fluid transmitted from the reservoir 104 to the tip 114. Also, if the first control actuator 110 is activated, the user may selectively adjust the pressure of fluid expelled from the tip 114.

When the massage mode is activated, such as by a user providing an input to the oral irrigator 100 through one of the control actuators 110, 112, 113, 124, the fluid output characteristics may be modified. For example, the third control actuator 113 may be used to activate a massage mode for the oral irrigator 100. During massage mode, the processing element 170 selectively activates the gate 176 to vary the signal provided to the motor 142. In one example, the signal generator 166 applies a varying signal to the motor 142, which causes the motor 142 to selectively vary one or more movement characteristics. For example, the signal generator 166 may apply a signal that has a variable voltage across a predetermined time duration. The signal may vary not only in magnitude, but also in frequency (e.g., time between a high voltage and a low voltage).

With reference to FIG. 7, the amplifier 174 increases the signal generated by the signal generator 166 and provides the increased control signal to the motor 174. The control signal may selectively interrupt or vary the power supplied to the motor 142, causing the motor to intermittently stop and/or slow down, reducing, stopping, or changing the movement of the drive shaft 143. As the drive shaft 143 varies, the movement of the piston 145 also varies, changing the length of pulses produced by the pump 146, as well as the pressure output by the pump 146. As an example, when the control signal is low or otherwise configured to prevent or reduce power from being transmitted to the motor 142, the motor 142 stops rotating the drive shaft 143, which in turn, stops movement of the piston 145, reducing or stopping fluid from flowing from the reservoir 104 to the tip 114.

In one example, a first control signal creates 0.5 second pulses. In other words, the pump 146 may produce 2 pulses per second, which may be a substantially slower pulse rate than the pulse rate due to the reciprocating nature of the pump 146 alone, and each pulse may have a substantially longer duration as compared to the normal mode. However, it should be noted that other pulse rates are envisioned and will be discussed in more detail below with respect to FIGS. 10A-10C.

In some implementations, the flow rate of the oral irrigator during massage mode may be reduced as compared to the flow rate during normal mode. As a specific example, the massage mode flow rate may be between 40 to 70 percent and often 50 to 60 percent of the flow rate during normal mode. In some implementations, the oral irrigator 100 may have a flow rate during clean mode ranging between 300-400 mL per minute and often may be about 370 mL per minute and during massage mode the flow rate may range between 150-200 mL per minute or lower and often may be 222 mL per minute.

Figure 9A:
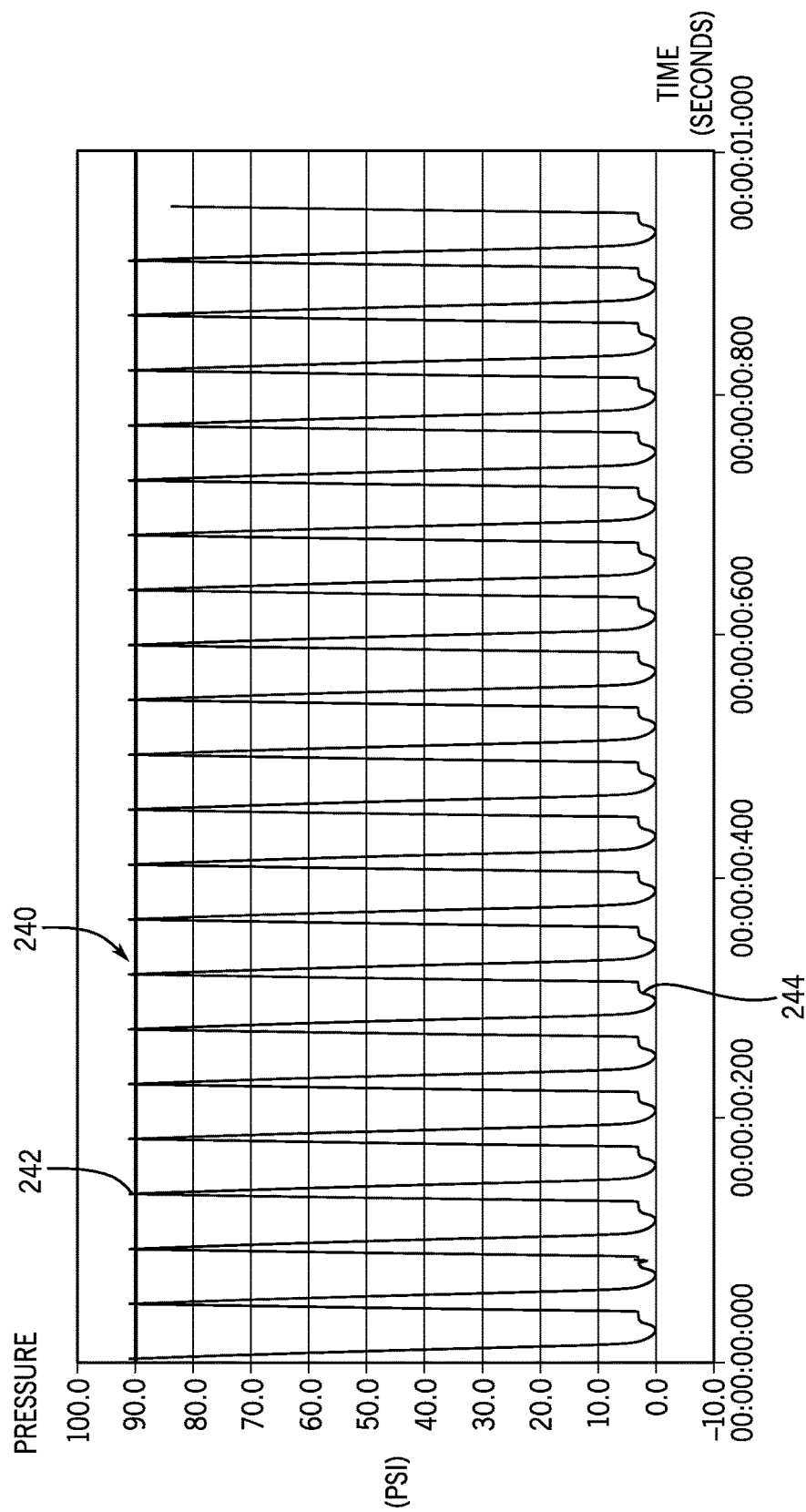
FIG. 9A is a chart illustrating an example of pressure ranges for the oral irrigator during clean mode.
Figure 9B:
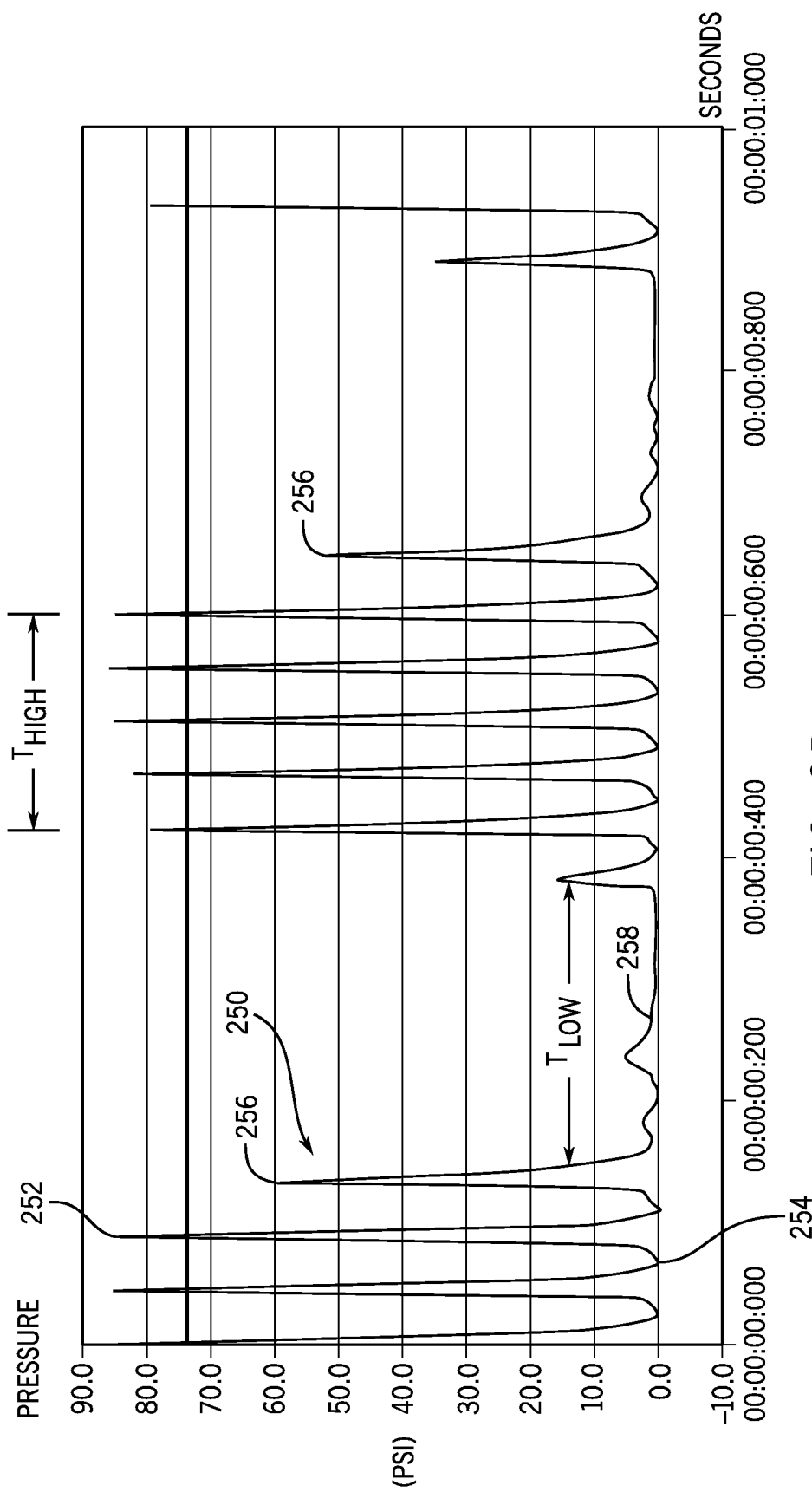
FIG. 9B is a chart illustrating an example of pressure ranges for the oral irrigator during massage mode.

In addition to changing the pulse rate, the control signal may also vary the magnitude of power provided to the motor 142, which may increase or decrease the outlet pressure of the pump 142. In a specific implementation, the outlet pressure of the oral irrigator during cleaning mode may range between 70 to 95 psi, and often average between 90-93 psi and during massage mode may range between 60 to 90 psi, and often average between 80-87 psi. FIG. 9A is a chart illustrating an example outlet pressure of the oral irrigator during clean mode. FIG. 9B is a chart illustrating an example outlet pressure of the oral irrigator during massage mode. With reference to FIGS. 9A and 9B, by applying an increased voltage to the motor 142, the current supplied to the motor 142 may also increase, increasing the torque of the motor 142. The increased torque may exert an increased force on the piston 145, to increase the output pressure of the oral irrigator 100. Accordingly, in some examples, the control signal may vary not only the durations for which a voltage is applied to the motor, but also the magnitude of the voltage in order to vary not only the fluid pulses but also the fluid pressure output by the oral irrigator 100.

As the fluid exits the tip 114, the user may direct the flow on his or her teeth, gums, tongue, cheeks, or the like. The varying control signals may vary the fluid output by the tip 114. In some examples, the variation in fluid may create a massage effect on a user's gums. For example, during each pulse fluid may not exit from the tip 114, allowing blood to return to the user's gums (i.e., capillary refill) before the next fluid stream hits the gums. This may provide a massaging effect, as well as may stimulate blood flow to the gums and enhance the cleaning experience with the oral irrigator.

The signal generator 166 may vary a frequency and magnitude of the control signal based on a desired output pulse rate and fluid pressure. FIGS. 10A-10C illustrate control signals that may be created by the signal generator to be applied to the motor 142. The control signals may include one or more voltage peaks and voltage minimums. As some illustrative examples, the voltage peaks may be 170V, 15V, 12V, 6V, or other values and the voltage minimums may be a subset of the voltage peaks and often may be substantially or about 0V. However, it should be noted that many other voltage values are envisioned and the voltage of the control signal may depend on the motor, the processing element, and other system parameters and as such may be modified as desired.

With reference to FIG. 10A, a control signal 200 may be a square wave having a voltage peak 202 or amplitude and a voltage minimum 204. In some examples, the voltage peak 202 (i.e., maximum voltage) may be applied for a duration T1 and the voltage minimum 204 may be applied for a duration T2. In this example, the durations T1 and T2 may be approximately equal. In a particular implementation, the peak voltage 202 may be approximately 12 V and the minimum voltage 204 may be 0 V, additionally both durations T1 and T2 may have a length of approximately 100 ms.

When the control signal 202 of FIG. 10A is applied to the motor 142, during the duration T2 of the minimum voltage 204, the motor 142 may not receive power. In other words, because the minimum voltage 204 is set to 0 V, the motor 142 is not activated. As the motor 142 does not receive power during the duration of the minimum voltage 204, the drive shaft 143 slows down and stops moving, stopping movement of the piston 145 within the pump 146. Thus, during the duration T2, the pump 146 does not pump fluid, creating a pause in fluid flow. Then, when the peak voltage 202 is applied, the motor 142 may begin rotating the drive shaft 143, causing the piston 145 to push fluid from the pump 146, activating the fluid flow. In this example, the minimum voltages 204 may define the "pulse" length, or the intermission between fluid output.

With continued reference to FIG. 10A, in another example, the maximum voltage 202 may be selected to be approximately 12V and the minimum voltage 204 may be selected to be approximately 6 V or half of the maximum voltage. However, in other embodiments, the minimum voltage may be 0V in this example as well. Additionally, the two time durations may be selected to be 160 ms. In this example, during second duration T2 when the minimum voltage 204 is applied to the motor 142, the motor 142 may receive some power, but the power may be reduced as compared to the maximum voltage 202. In this example, the motor 142 may still rotate the drive shaft 143, but may do so at a reduced torque and speed, which may also cause a reduced flow rate and pressure output by the pump 146. In this example, during each pulse, fluid may be output from the tip 114, but at a slower flow rate and pressure.

In yet another implementation, the time durations T1 and T2 may be selected to be 250 ms. In these examples, the frequency of the pulses may be reduced, such that there may be fewer pulses per second as compared to examples where the time durations may be shorter.

In FIG. 10A, because the time durations T1 and T2 may be substantially equal, the time of fluid output and fluid pause may be substantially the same. However, in other examples, the time durations for the maximum voltage and the minimum voltage may be varied. With reference to FIG. 10B, a control signal 212 may include a voltage maximum 212 having a duration T3 and a voltage minimum 214 having a duration T4. In this example, the peak time duration T3 may be shorter than the minimum time duration T4, which may result in longer "pauses" in fluid flow or pulses. The time duration T4 may be twice, three times, or more, the length of the peak time duration T3.

As one example, the minimum voltage time duration T4 may be three times as long as the maximum voltage time duration T3. Thus, the pause in fluid flow may last three times as long as the fluid flow segments or pulses. In a specific implementation, the maximum voltage 212 may be 12V and may have time duration T3 of 100 ms, the minimum voltage 214 may be 0V and may have a duration of 300 ms. However, the above values are illustrative only and many other implementations are envisioned. Furthermore, although the control signal 210 in FIG. 10B is illustrated as having a longer low voltage duration T4 than maximum voltage duration T3, in some examples, the maximum voltage time duration T3 may be longer than the minimum voltage time duration T4. In these examples, the pauses or breaks between fluid flow may be reduced as compared to the fluid stream time durations.

In the control signals 200, 210 illustrated in FIGS. 10A and 10B, there may be a rapid transition between the maximum or peak voltage 202, 212 and the minimum voltage 204, 214. For example, both control signals 200, 210 may be square waves that substantially instantaneously transition between minimum and maximum values. However, in other examples, the control signal may gradually transition between a maximum and minimum voltage.

With reference to FIG. 10C, a control signal 220 having a sinusoidal shape is illustrated. The control signal 220 may have a peak voltage 222 and a minimum voltage 224, with the peak voltage 220 having a time duration T5 and the minimum voltage having a time duration T6. However, because the control signal 220 may gradually change between the maximum and minimum levels, the durations T5 and T6 may represent the time between inflection points 226, 228. The inflection points 226, 228 generally may represent half of a cycle or period for the control signal 220. In other words, the sum of the durations T5 and T6 may represent the period for the control signal 220.

Using the control signal 220 of FIG. 10C, the motor 142 may more subtly transition between the high and low states of fluid flow. That is, the transition between the "pulses" may be tapered so that there may not be a sudden reduction in fluid flow, but a more gradual reduction. In some examples, the peak voltage 222 may be three times as large as the minimum voltage 224. As one example, the peak voltage 222 may be selected at 15V and the minimum voltage 224 may be selected at 3V. In this example, the period of the control signal 220 may be 1800 ms with the high duration T5 being 900 ms and the low duration T6 being 900 ms. Although the control signal 222 shown in FIG. 8C is a sine wave, other waveforms are envisioned, such as combination waveforms (e.g., having characteristics of multiple wave types), elliptical waveforms, and the like. Accordingly, the discussion of any particular waveform is meant as illustrative only.

As briefly described above, the massage mode module 172 may not only vary the pulse rate fluid flow of the oral irrigator, but may also vary an outlet fluid pressure for the oral irrigator. With reference again to FIG. 9A, the oral irrigator 100 may pulse rapidly (which may be due to the reciprocating nature of the pump) and the outlet pressure 240 may vary between peaks 242 and valleys 244. As can be seen from the graph in FIG. 9A, each pressure peak 242 may be generally close together with a pressure pulse rate of just over 21 peaks per second. Additionally, the average pressure for the peaks 242 may be 91.8 psi and generally the pressure at the peaks 242 ranges between 91 and 92 psi. The example outlet pressures discussed herein are meant as illustrative only and may be higher or lower based as desired.

With continued reference to FIG. 9A, the output pressure 240 may also drop to the valleys 244, which may hover around 0 psi before the pressure ramps back up extend towards a pressure peak 242. Each of the valleys 244 may occur while the piston 145 in the pump 146 is drawing fluid into the pump chamber before it expels the fluid and are therefore due to the reciprocating nature of the pump 146. Accordingly, in examples where a non-reciprocating pump may be used, the outlet pressure during normal mode may be substantially constant.

With reference again to FIG. 9B, during massage mode, the outlet pressure 250 of the oral irrigator 100 may be lower than during clean mode (shown in FIG. 9A) and may also have non-pulsating periods during which the outlet pressure may be close to or at 0 psi. For example, the outlet pressure 250 may include a high pressure period $T_{high}$ and a low pressure period $T_{low}$. During the high pressure period $T_{high}$, the outlet pressure 250 may include a plurality of pressure peaks 252, as well as ramp peaks 256 that are the pressure peak while the oral irrigator 100 is transitioning between the high pressure period and the low pressure period. Additionally, the outlet pressure 250 may include valleys 254, 258. The first valley 254 may be during the high pressure $T_{high}$ period and may be due to the reciprocating nature of the piston 145, as discussed above with respect to FIG. 9A. The second valley 258 represents the low pressure period between pulses of high pressure. During the low pressure period $T_{low}$, the oral irrigator 100 may output little to no pressure.

As shown in FIG. 9B, in some examples, the oral irrigator 100 may have an average outlet pressure of 85.9 psi during massage mode. As with the clean mode, many other outlet pressures are envisioned and the above examples are meant as illustrative only and not limiting.

Figure 11:
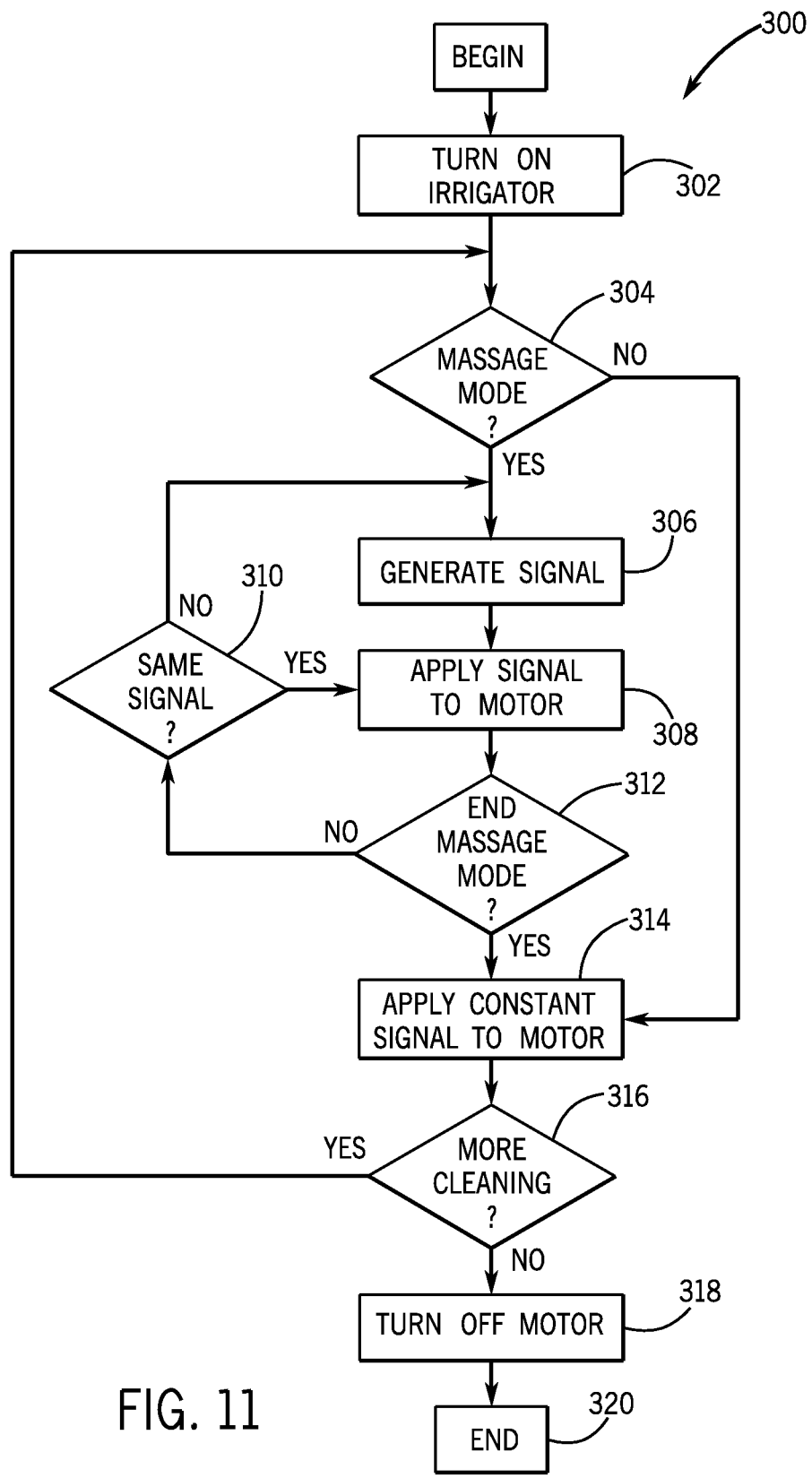
FIG. 11 is a flow chart illustrating a method for operating the oral irrigator including the massage mode module.

A method for operating the oral irrigator 100 including the massage mode module 172 will now be discussed in more detail. FIG. 11 is a method 300 for activating the massage mode. The method 300 may begin with operation 302 and the irrigator 100 may be activated. For example, the second control actuator 112 may be selected by a user to turn on the oral irrigator 100. Once the oral irrigator 100 is activated, the method 300 may proceed to operation 304. In operation 304, the processing element 170 may determine whether massage mode has been activated. For example, the processing element 170 may determine whether a user has provided an input to one of the control actuators 110, 112, 113, 124 to select the massage mode. In a specific implementation, the switch 148 may provide an input to the processing element 170 when the second control actuator 112 is activated. As another example, the massage mode may be activated automatically after a select time period of activation of the irrigator 100, e.g., after 30 seconds of operation, the massage mode may be automatically activated.

If the massage mode is not activated, the method may proceed to operation 314, which will be discussed in more detail below. However, if in operation 304 the massage mode is activated, the method 300 may proceed to operation 306. In operation 306, the signal generator 166 may generate a control signal 200, 210, 220. The control signal generated 200, 210, 220 may be selected from a predetermined signal, or as will be discussed in more detail below with respect to FIG. 10, may be generated based on one or more user inputs.

Once the signal generator 166 has generated the control signal 200, 210, 220, the method 300 may proceed to operation 308. In operation 308 the control signal may be applied to the motor. For example, the gate 176 may be activated to provide the control signal from the signal generator 166 to the motor 142. As the control signal is applied to the motor 142, the motor 142 may drive the drive shaft 143 based on the signal. For example, the motor 142 may selectively slow down or stop rotation of the drive shaft and/or may decrease or reduce the torque produced by the drive shaft. The variations in the drive shaft movement may create related changes in the piston 145, thus varying the output of the pump 146, changing the output characteristics of the fluid flow from the tip 114.

After operation 308, the method 300 may proceed to operation 312. In operation 312, the processing element 170 may determine whether to end massage mode. For example, the user may provide a second input to the oral irrigator 100, e.g., by selecting one of the control actuators 110, 112, 124, to indicate that he or she wishes to resume normal mode. As another example, the oral irrigator 100 may have a predetermined time period for massage mode (e.g., 1 minute, or the like), and the processing element 172 may determine to end massage mode once the allotted time has passed.

In operation 312, if massage mode is not terminated, the method 300 may proceed to operation 310. In operation 310, the processor may determine whether the same control signal 200, 210, 220 should be applied to the motor or whether a different signal should be applied. If the control signal is to remain the same, the method 300 may return to operation 308 and the signal may continue to be applied to the motor 142. However, in operation 310 if a new signal is desired, the method 300 may return to operation 306 and the signal generator 166 may generate a new control signal. For example, in some examples, a user may wish to vary pressure, pulse rate, or the transition between pulses during massage mode. In these instances, the processing element 170 may receive a user input to vary the control signal and may instruct the signal generator 166 to create a new control signal or vary the current control signal.

With continued reference to FIG. 11, if in operation 312 massage mode is terminated, the method 300 may proceed to operation 314. In operation 314 the processing element 170 may provide a constant signal to the motor 142. In other words, the normal mode signal may be applied to the motor 142, and in some instances, the normal mode signal may be substantially constant. As the motor 142 receives the normal mode signal, movement of the drive shaft 143 may be constant, and any pulses in the fluid output may be due to the reciprocating nature of the pump 146, rather than variable movement in the motor 142.

After operation 314, the method 300 may proceed to operation 316. In operation 316, the processing element 170 may determine whether more cleaning is desired. For example, the processing element 170 may determine whether the user has deactivated the power control actuator 112. As another example, the oral irrigator may be configured to have an activation time corresponding to a predetermined "cleaning" length and once the time length has expired, the oral irrigator 100 may automatically shut off.

If more cleaning is desired, the method 300 may return to operation 304. However, if no additional cleaning is desired, the method 300 may proceed to operation 318. In operation 318, the processing element 170 may deactivate the motor. As one example, the processing element 170 may switch off a connection between the power supply 115 and the motor 142. After operation 318, the method 300 may proceed to an end state 320.

Figure 12:
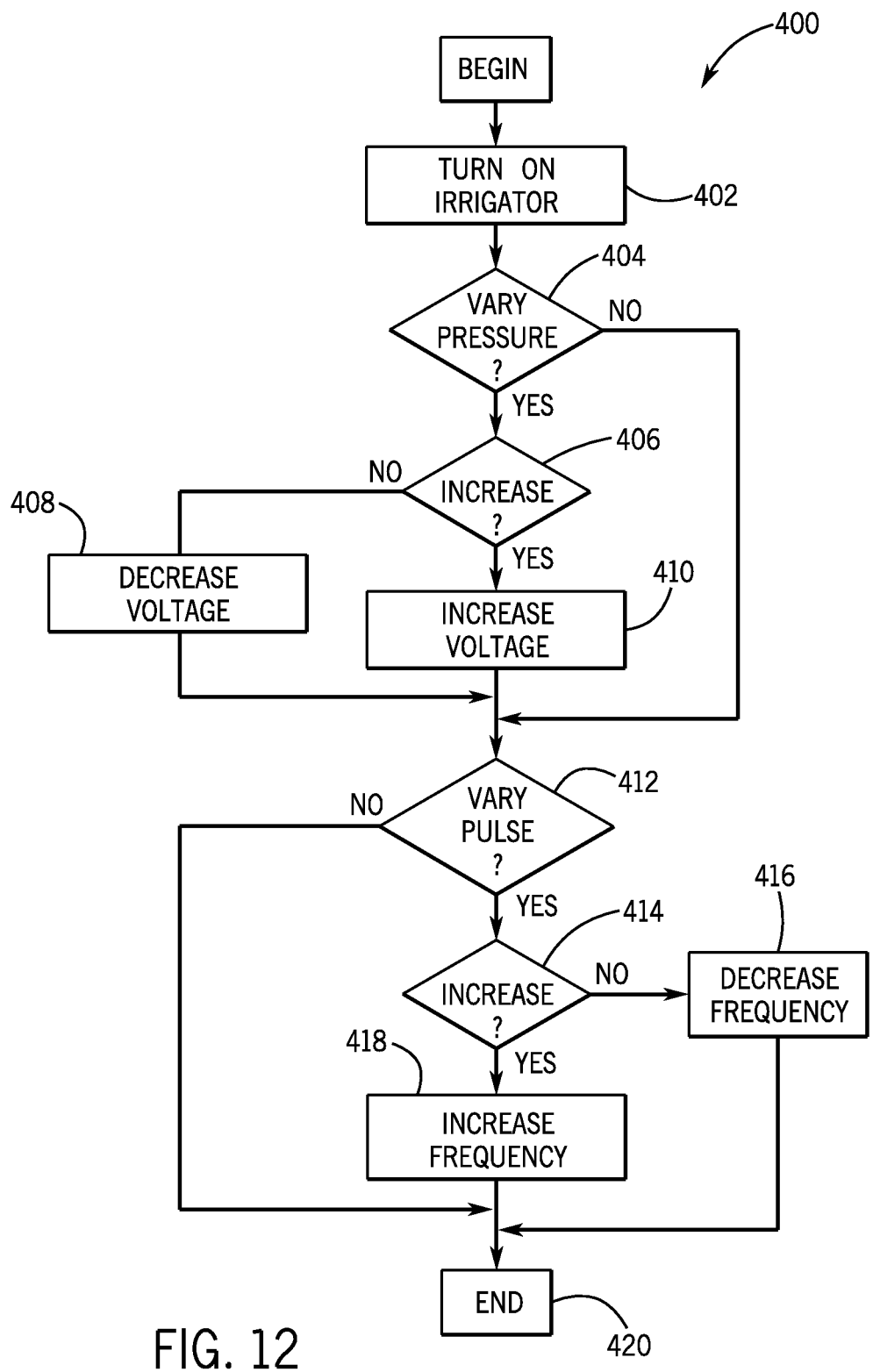
FIG. 12 is a flow chart illustrating a method for dynamically adjusting the pressure and pulse rate of the oral irrigator using the massage mode module.

In some examples, the pressure and pulse rate of the massage mode may be statically set. However, in other examples, the pressure and pulse rate of the pulses during massage mode may be dynamically modifiable or may be initially set by a user (e.g., calibrated to a particular user's preferences). FIG. 12 is a flow chart illustrating a method for dynamically modifying one or more characteristics of the fluid flow during massage mode. With reference to FIG. 12, the method 400 may begin with operation 402. In operation 402, massage mode for the oral irrigator 100 may be activated. For example, the user may select one of the control actuators 110, 112, 113, 124 to indicate his or her desire to enter massage mode. Once in massage mode, as described in operations 306 and 308 in FIG. 11, the signal generator 166 may generate a signal and apply the signal to the motor 142.

Once massage mode has been activated, the method 400 may proceed to operation 404. In operation 404, the processing element 170 may determine whether the outlet pressure should be varied. For example, one of the control actuators 110, 112, 113, 124 may be used to allow the user to provide an input indicating whether he or she wishes for the pressure to be increased or decreased. In a particular example, rotating one of the control actuators 110, 112, 113, 124 in a first direction may correspond to an increase in pressure and rotating in a second direction may correspond to a decrease in pressure.

If the pressure is to be varied from the current control signal output, the method 400 may proceed to operation 406. In operation 406 the processing element 170 may determine whether the pressure should be increased. In other words, the processing element 170 may determine whether the user input to vary the pressure corresponds to an increase in pressure or a decrease. It should be noted that in many implementations, operations 404 and 406 may be performed substantially simultaneously. For example, the processing element 170 may receive a single input that indicates both a change a pressure, as well as whether the pressure is to be increased or decreased.

In operation 406, if the pressure is going to be decreased, the method 400 may proceed to operation 408. In operation 408, the control signal 200, 210, 220 may be modified by the processing element 170 to reduce the maximum voltage 202, 212, 222, or reduce the amplitude of the control signal. As discussed above with respect to FIGS. 10A-10C, by decreasing the maximum voltage of the control signal, the output pressure by the pump 146 may be reduced due to a reduction in output torque by the motor. However, it should be noted that in other examples, the pressure may be decreased manually, such as by a user closing or opening a valve, such as by-pass valve or the like. In these examples, the control signal may not be modified, but the mechanical properties of the fluid path between the reservoir 104 and the tip 114 may be changed.

If in operation 406 the pressure is going to be increased, the method 400 may proceed to operation 410. In operation 410, the peak voltage 202, 212, 222 or amplitude of the control signal 200, 210, 220 may be increased. As a specific example, the peak voltage may increase from 10 V to 12 V. As discussed above, the outlet pressure may be related to the voltage applied to the motor 142 by the control signal, such that a change in the voltage may correspond to a change in pressure.

After either operation 408 or 410, the method 400 may proceed to operation 412. In operation 412, the processing element 170 may determine whether the pulse length and/or pulse rate should be varied. For example, the user may be provide input to the oral irrigator 100 through one or more of the control actuators 110, 112, 113, 124 indicating his or her desire to increase the pulse rate or length.

If the pulse rate is going to be varied, the method 400 may proceed to operation 414. In operation 414, the processing element 170 may determine whether the pulse rate is going to be increased. For example, the user input to vary the pulse rate may also include an indication of whether the pulse rate should be increased or decreased. Additionally, as discussed above with respect to pressure, in some examples, the user input indicating that the pulse rate should be varied may also include data indicating whether the pulse rate should be increased or decreased.

In operation 414, if the pulse rate is going to decrease, the method 400 may proceed to operation 416. In operation 416, the signal generator 166 may decrease the frequency of the control signal 200, 210, 220. As an example, the duration T1, T2, T3, T4, T5 may be increased, such that the cycles per unit of time of the control signal may be increased, reducing the number of pulses per second.

In operation 414 if the pulse rate is going to be increased, the method 400 may proceed to operation 418. In operation 418, the signal generator 166 may increase the frequency of the control signal. For example, the duration T1, T2, T3, T4, T5 for the control signal may shorten, increasing the number of cycles of the control signal per minute. By shortening the length of the maximum and minimum voltages applied to the motor 142, the length of each pulse may be shortened, increasing the number of pulses per time frame.

After operations 416 or 418 or if in operation 412 the pulse rate is not going to be changed, the method 400 may proceed to an end state 420 and may terminate. It should be noted that the method 400 is an illustrative method for varying one or more characteristics of the fluid flow through the tip 114 during massage mode. However, many other methods are envisioned. As one example, the transition between high and low or fluid flow and a pulse may be varied by changing the transition between the maximum and the minimum voltage levels in the control signal. As another example, the length of fluid flow as compared to pulses or breaks in fluid flow may be varied by changing the duration T1, T2, T3, T4, T5 that either the maximum voltage or the minimum voltage is applied to the motor 142.

As generally discussed above, the processing element 170 may vary a control signal to the motor 142 to change either or both the fluid pulse rate and/or the fluid outlet pressure. In other examples, the processing element 170 may activate a switch or valve to vary the pulse rate and/or pressure. As a first example, the processing element 170 may be in communication with an electrical valve such as a solenoid valve and when the massage mode is activated, the processing element 170 may vary the voltage of the valve to change the pressure and/or may selectively open and close the valve to change the flow rate of the oral irrigator 100. As a second example, the oral irrigator 100 may include a gear driven turbine or a water driven turbine that may be mechanically actuated or actuated by the processing element 170 to vary the flow rate of the oral irrigator 100.

Structural Elements of the Oral Irrigator

Figure 13A:
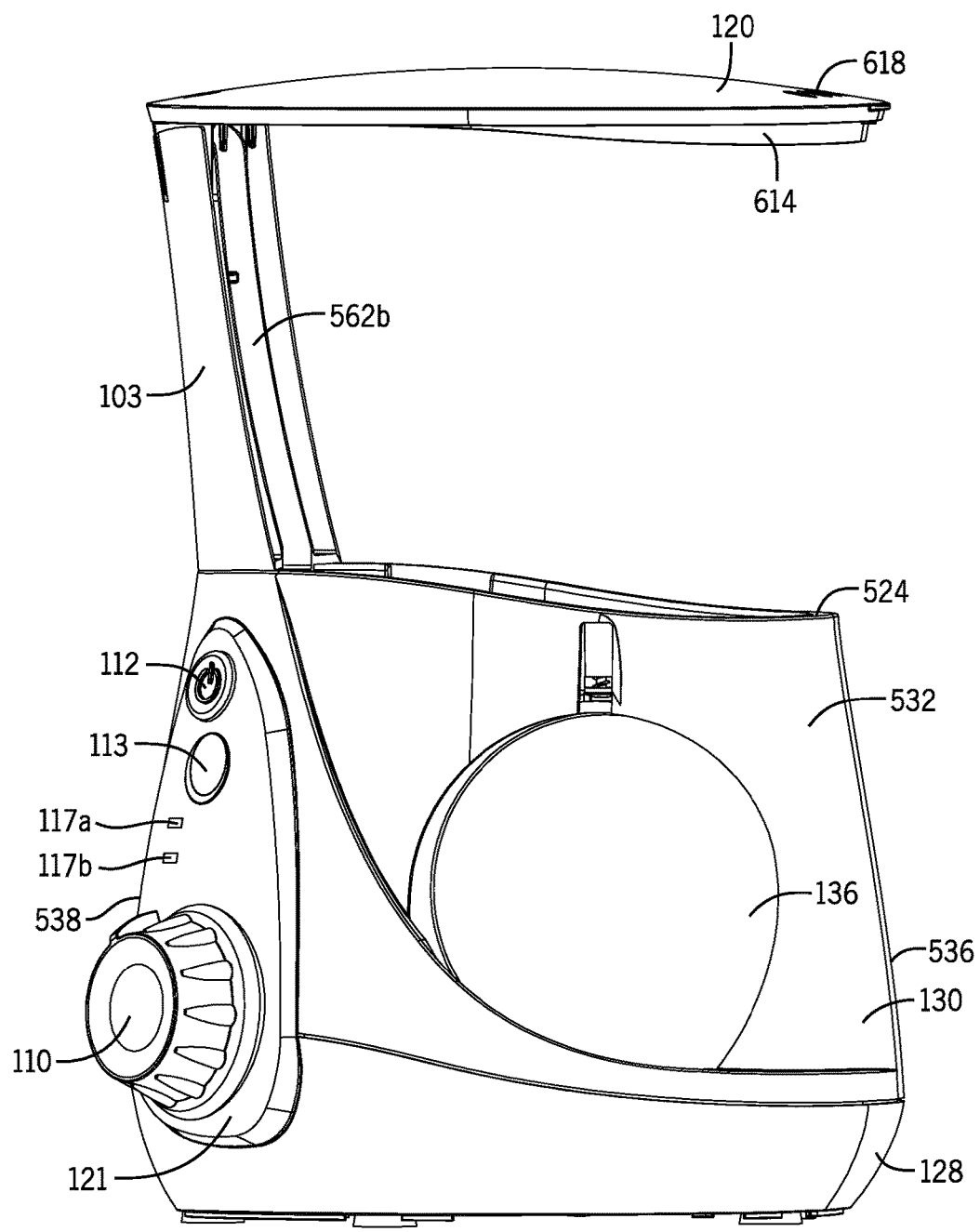
FIG. 13A is a front elevation view of the oral irrigator of FIG. 1A with the reservoir removed.
Figure 13B:
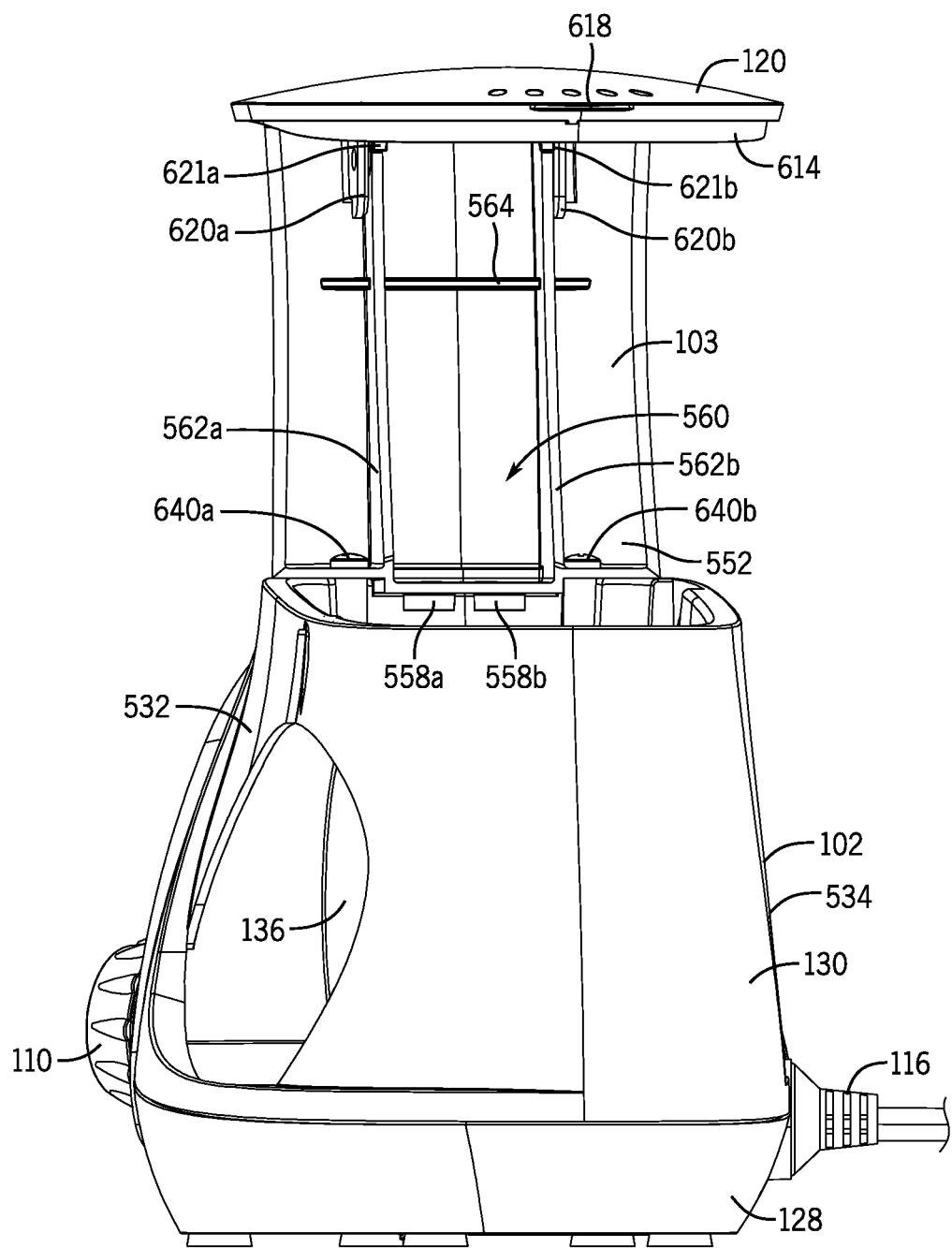
FIG. 13B is a right side elevation view of the oral irrigator of FIG. 13A.
Figure 14:
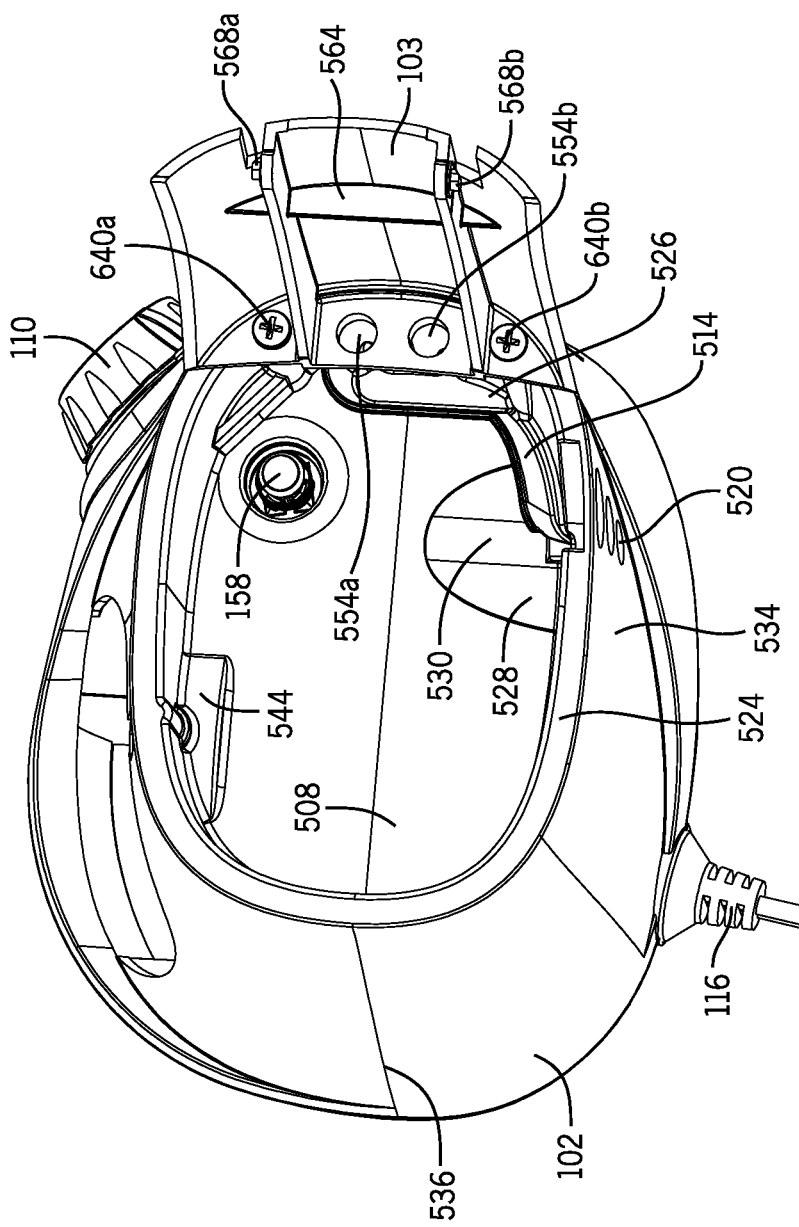
FIG. 14 is a top plan view of the oral irrigator of FIG. 1A with the reservoir and lid removed.
Figure 15:
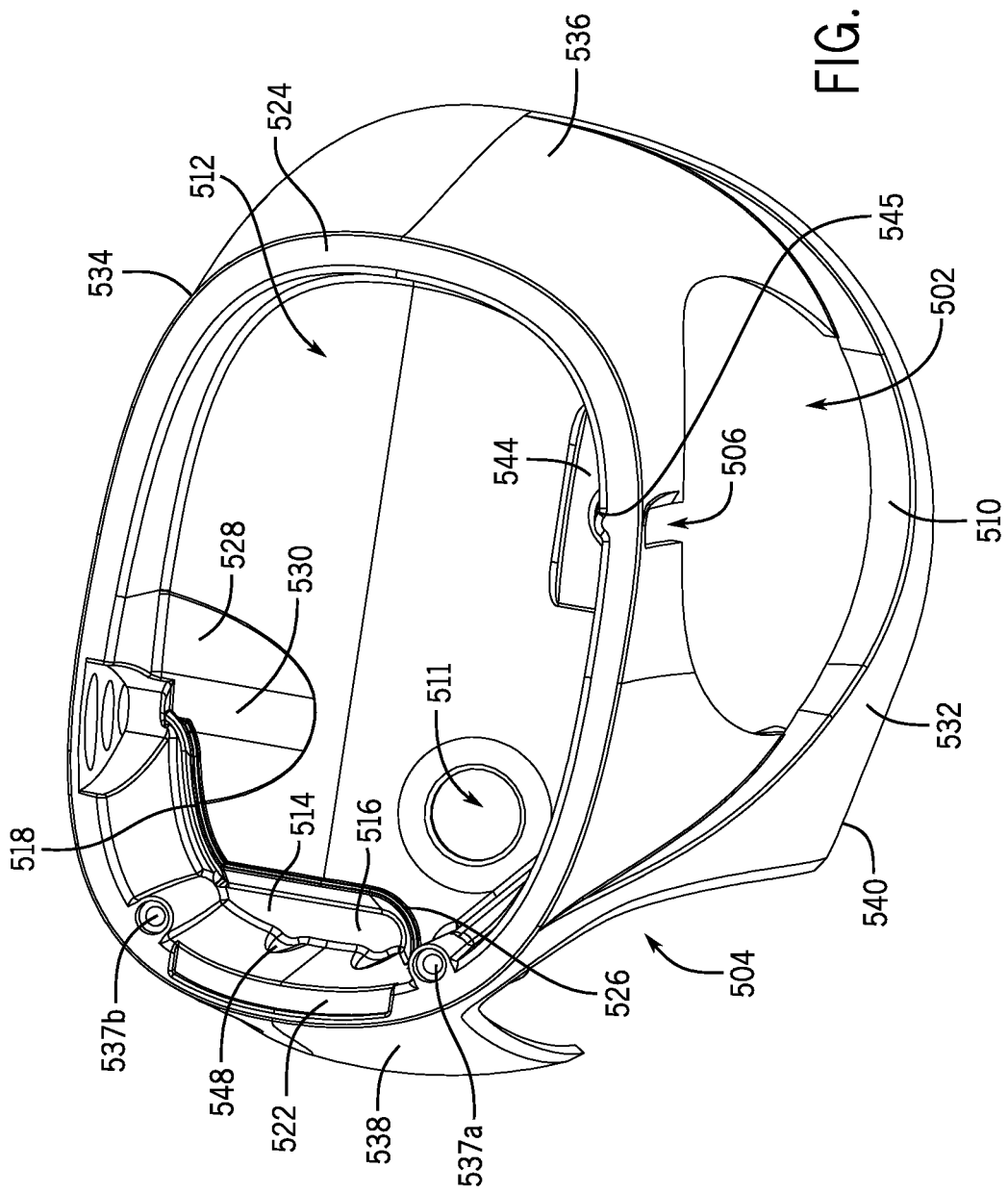
FIG. 15 is a top perspective view of a base for the oral irrigator of FIG. 1A.
Figure 16:
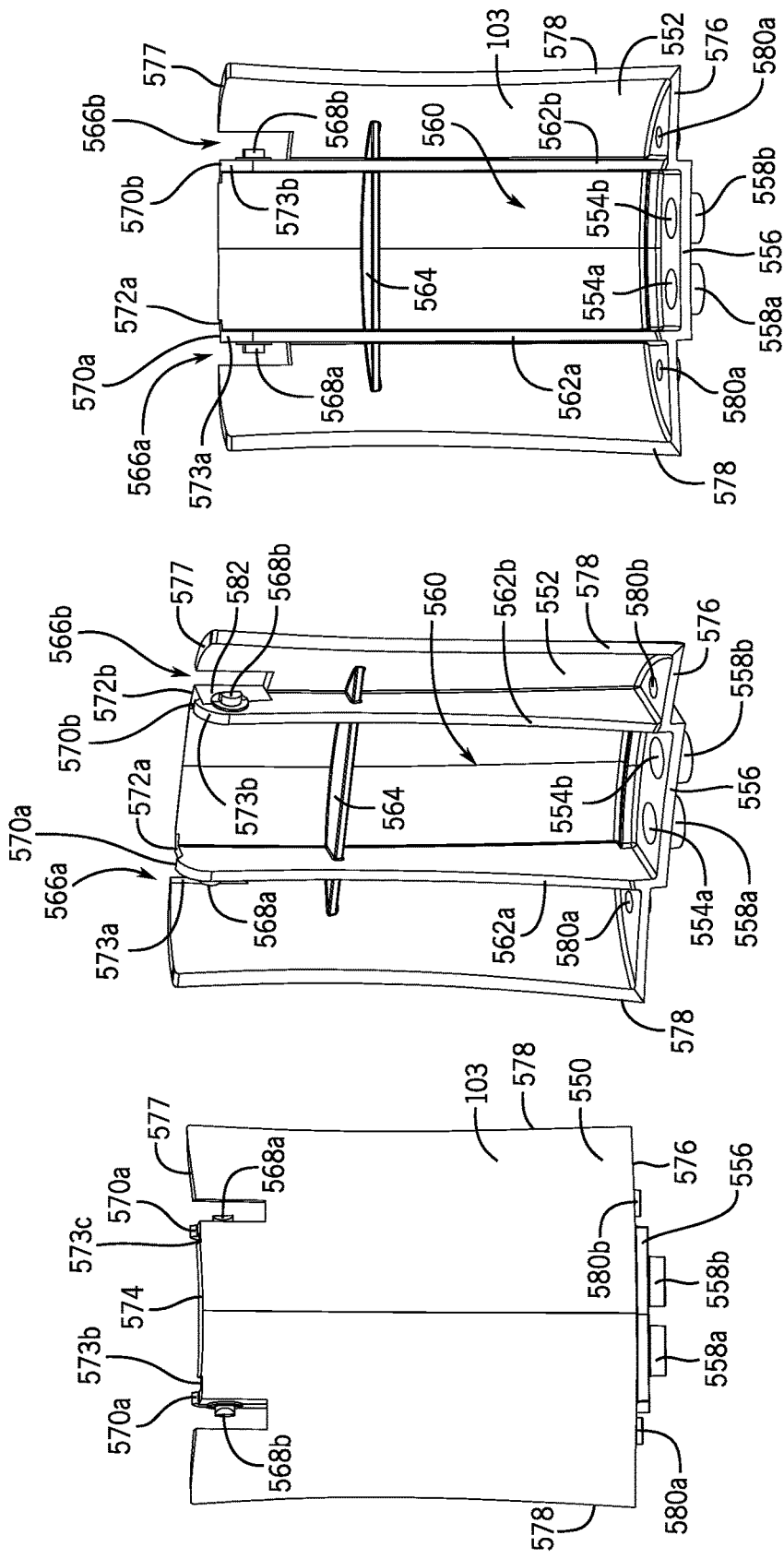
FIG. 16A is a front elevation view of a prow for the oral irrigator of FIG. 1A.
FIG. 16B is a rear perspective view of the prow of FIG. 16A.
FIG. 16C is a rear elevation view of the prow of FIG. 16A.

Structural features of the oral irrigator will now be discussed in more detail. As discussed above with respect to FIGS. 1A-1E, the base 102 supports the pump assembly 119, reservoir 104, and lid 120. FIG. 13A is a front perspective view of the oral irrigator with the reservoir removed and select components hidden for clarity. FIG. 13B is a side elevation view of the oral irrigator of FIG. 13A. FIG. 14 is a top perspective view of the oral irrigator with the reservoir and lid removed and select components hidden for clarity. FIG. 15 is a top perspective view of the upper base. With reference to FIGS. 13A-15, the base 102 includes a lower base 128 and an upper base 130. The upper base 130 is defined by a front wall 532, back wall 534, two sidewalls 536, 538, and a top surface 508. The bottom end of the upper base 130 is open beneath the top surface 508 (see FIG. 20) and bottom edges of the walls 532, 534, 536, 538 to connect to the lower base 128. In this configuration the upper base 130 forms a cover for the lower base 128.

With reference to FIG. 15, the front wall 532 of the upper base 130 includes a hose wall aperture 502. The hose wall aperture 502 is defined through the front wall 532 and, as shown in FIG. 15, has a generally circular shape, but may otherwise be configured as desired. The hose wall aperture 502 may further define a clamp slit 506 at a top end of the aperture 502. The clamp slit 506 defines a rectangular shaped opening that receives a connecting element of the clamp 134. Additionally, the front wall 532 further defines a faceplate cutout 504 extending between the front wall 532 and the second sidewall 538, i.e., wrapping around the corner between the front wall 532 and the sidewall 538. The faceplate cutout 504 may be configured to correspond to the control faceplate 121 and, as such, may have an inverted "U" or horseshoe shape with the open end of the U facing towards a bottom end of the upper base 130.

With reference to FIGS. 13A and 15, the upper base 130 further includes a ledge 510 extending outward from the front wall 532. The ledge at the top edge 524 of the upper base 130 and extends downward towards the bottom edge 540. The ledge 510 may have a concave shape and wrap around a bottom end of the hose wall aperture 502. The ledge 510 may vary in thickness between the top edge 524 and bottom edge 540 of the upper base 130. For example, the ledge 510 may increase in thickness as it extends downwards towards the bottom edge 540, such that ledge 510 increases in thickness the closer it gets to the bottom edge 540. The ledge 510 acts to separate the hose cavity 136 from the lower base 128 and creates an aesthetically appealing design feature for the oral irrigator.

With reference to FIGS. 1B and 15, the back wall 534 of the upper base 130 may also include a similarly shaped ledge 542. The ledge 542 on the back wall 534 may match the shape and extension direction of the ledge 510 on the front wall 532, i.e., the ledges may be similarly shaped and curved. However, although the ledge 542 may vary in thickness between the top and bottom of the upper base 130, the thickness of the ledge 542 on the back wall 534 may be reduced as compared to the ledge 510 on the front wall.

With reference to FIGS. 1B and 15, the back wall 534 further includes one or more drain outlets 520. The drain outlets 520 are apertures defined through the back wall 534. In one example, one drain outlet 520 may be positioned towards a top end 524 of the upper base 130 and is in fluid communication with the top surface 508 of the upper base 130, as will be discussed in more detail below.

With reference to FIGS. 14 and 15, the top surface 508 of the upper base 130 is recessed from the top edge 524 to define a receiving cavity 512 for the reservoir 104. The top surface 508 of the upper base 130 supports the reservoir 104 and also includes one or more flow paths to allow fluids and debris that accumulate on the upper base 130 to drain out. In particular, the top surface 508 includes a first drainage path 514 and a second drainage path 528. The drainage paths 514, 528 act as gutters for the upper base 130 to direct fluid and debris out of the base 130. The flow path of fluid through the drainage system will be discussed in more detail below.

The first drainage path 514 includes a drip catch 516 and a drain channel 518. The drip catch 516 has an oblong shape and is recessed into the top surface 508 defining a depression. The drip catch 516 is positioned adjacent the interior surface of the second sidewall 538 and narrows as it follows the interior surface of the sidewall 538 around to the interior surface of the back wall 534 to define the drain channel 518. The drain channel 518 is in fluid communication with the drain outlet 520. In some embodiments, the first drainage path 514 is configured to encourage fluid to flow from the drip catch 516 to the drain channel 518 and out of the base via the outlet 520. In these embodiments, the drain channel 518 may be angled or slanted downward towards the drain outlet 520. As the drain channel 518 and drip catch 516 are recessed from the top surface, a wall 526 is defined between the top surface 508 and the first drainage path 514. The wall 526 may also extend upwards past the top surface 508 as it follows the perimeter of the first drainage path 514. In this configuration, the wall 526 is raised above the top surface 508 and separates the first drainage path 514 from the top surface 508.

The second drainage path 528 is recessed on the top surface 508 and includes a central area recessed from the top surface further than the second drainage path 528 to define a drain channel 530. In this configuration, fluid and debris are encouraged to flow into the drain channel 530 running through the midsection of the second drainage path 528. The drain channel 530 is aligned with the drain outlet 520 and the angle of the second drainage path 528 and drain channel 520, along with the help of gravity, encourages fluid and debris to flow from the top surface 508 into the second drainage path 528 and into the drain channel 530.

In some embodiments, the first drainage path 514 running along the side of the top surface 508 is deeper than the second drainage path 528, but in other embodiments the two drainage paths may be recessed at similar depths or the second drainage path 528 may be further recessed than the first drainage path 514.

With continued reference to FIG. 15, one or more alignment depressions 548 may be formed in an interior surface of the second sidewall 538. The alignment depressions 548 may begin at the intersection of the first drainage path 514 and the sidewall 538 and extend upwards towards the top edge 524. The alignment depressions 548 may terminate at a height that generally corresponds to a height of the wall 526 or may terminate at a height higher than the wall 526. The alignment depressions 548 may be generally conically shaped and taper towards a top end.

With reference to FIGS. 4B, 14, and 15, the upper base 130 may define a valve aperture 511 in the top surface 508. The valve aperture 511 extends through the top surface 508 and is configured to receive one or more components of the valve assembly 156 for the oral irrigator 100. An annular rim 546 (see FIG. 4B) extends downward from the top surface 508 towards the bottom edge 540 of the upper base 130. The annular rim 546 surrounds the valve aperture 511.

With reference to FIG. 15, the upper base 130 may further include a raised seat 544 positioned on the top surface 508 towards the front wall 532. In some embodiments, the seat 544 may have an arcuate shape and is configured to receive a recess on a bottom surface of the reservoir 104. The seat 544 may also help to align the reservoir 104 within the receiving cavity 512 of the upper base 130. Although a single seat 544 is illustrated, additional engagement features may also be included either along the top surface and/or interior sidewalls of the upper base 130.

With reference again to FIG. 13A, the prow 103 forms a backbone structure for the oral irrigator and connects the lid 120 to the base 102. FIGS. 16A-16C illustrate various views of the prow 103 removed from the base 102. With reference to FIGS. 16A-16C, the prow 103 has an outer surface 550 and an interior surface 552. The prow 103 has a convexly curved shape such that the outer surface 550 extends outwards away from the reservoir 104 when the reservoir is connected to the oral irrigator 104. The prow 103 may also be somewhat triangularly shaped in horizontal cross-section. Further, the top ends 577 of two side edges 578 extending upwards from base 576 are in a different plane than the bottom ends of the side edges 578 (see FIG. 13A).

With reference to FIGS. 16A-16C, the base 576 of the prow 103 includes two fastening apertures 580a, 580b defined in the base 576 and a bottom shelf 556. The bottom shelf 556 is stepped down from the portion of the base 576 defining the fastening apertures 580a, 580b and is positioned between the two fastening apertures 580a, 580b. Two tip apertures 554a, 554b are defined in the shelf 556 and extend therethrough. Sleeves 558a, 558b extending downward from a bottom surface of the shelf 556 and surround each of the tip apertures 554a, 554b. The tip apertures 554a, 554b and sleeves 558a, 558b may generally correspond to the shape and size of the tip 114 but, depending on the type of accessories used with the oral irrigator 100, may be varied to accommodate other shapes and sizes. Also, although only two tip apertures are illustrated, the number and position of the tip apertures may be varied as desired.

Two ribs 562a, 562b extend upwards from base 576 to separate the fastening apertures 580a, 580b from the shelf 556. The ribs 562a, 562b also extend inwards from the interior surface 552 of the prow 103. The ribs 562a, 562b provide additional strength for the prow 103 and also may function as guiding tracks to direct the reservoir 104 into the upper base 128. With reference to FIG. 16C, a cradle 560 is defined between the two ribs 562a, 562b and the interior surface 552 of the prow 103.

With continued reference to FIG. 16C, the prow 103 may further include a horizontal support rib 564. The horizontal rib 564 provides structural support for the prow 103 and may also be used as a shield to prevent debris and fluid from reaching items that are stored in the cradle 560, as will be discussed in more detail below.

With reference to FIGS. 16A-16C, the prow 103 includes hinge slots 566a, 566b in the top edge 574. The hinge slots 566a, 566b extend downward towards the horizontal rib 564 terminating prior thereto. The hinge slots 566a, 566b are generally rectangular shaped and are aligned to be at least partially parallel to the ribs 562a, 562b. In one embodiment, the hinge slots 566a, 566b are positioned between the side edges 578 and the ribs 562a, 562b.

Two pivots 568a, 568b extend laterally outward from the sidewalls of the ribs 562a, 562b towards the edges 578 of the prow 103. The pivots 568a, 568b are aligned with at least a portion of the hinge slots 566a, 566b to allow the pivots to be accessible through the hinge slots. The pivots 568a, 568b may be generally cylindrically shaped but in some embodiments the pivots may also an angled surface edge 582 (see FIG. 16A) that may assist in connecting the lid 120 to the pivots 568a, 568b, as will be discussed below.

The prow 103 may further include seats 572a, 572b defined on the top edge 574 of the ribs 562a, 562b. The seats 572a, 572b define a relatively planar surface recessed below a shoulder 570a, 570b extending from the top surface of the ribs 562a, 562b. The shoulders 570a, 570b are raised above the seats 572a, 572b and a top surface of the shoulders 570a, 570b defines a cam surface 573a, 573b. For example, as the shoulders 570a, 570b transition outward and downward the cam surfaces 573a, 573b are defined and positioned on the top edges of the ribs 562a, 562b of the prow 103. The cam surfaces 573a, 573b define a rounded corner between the shoulders 570a, 570b and the ribs 562a, 562b.

Figure 17:
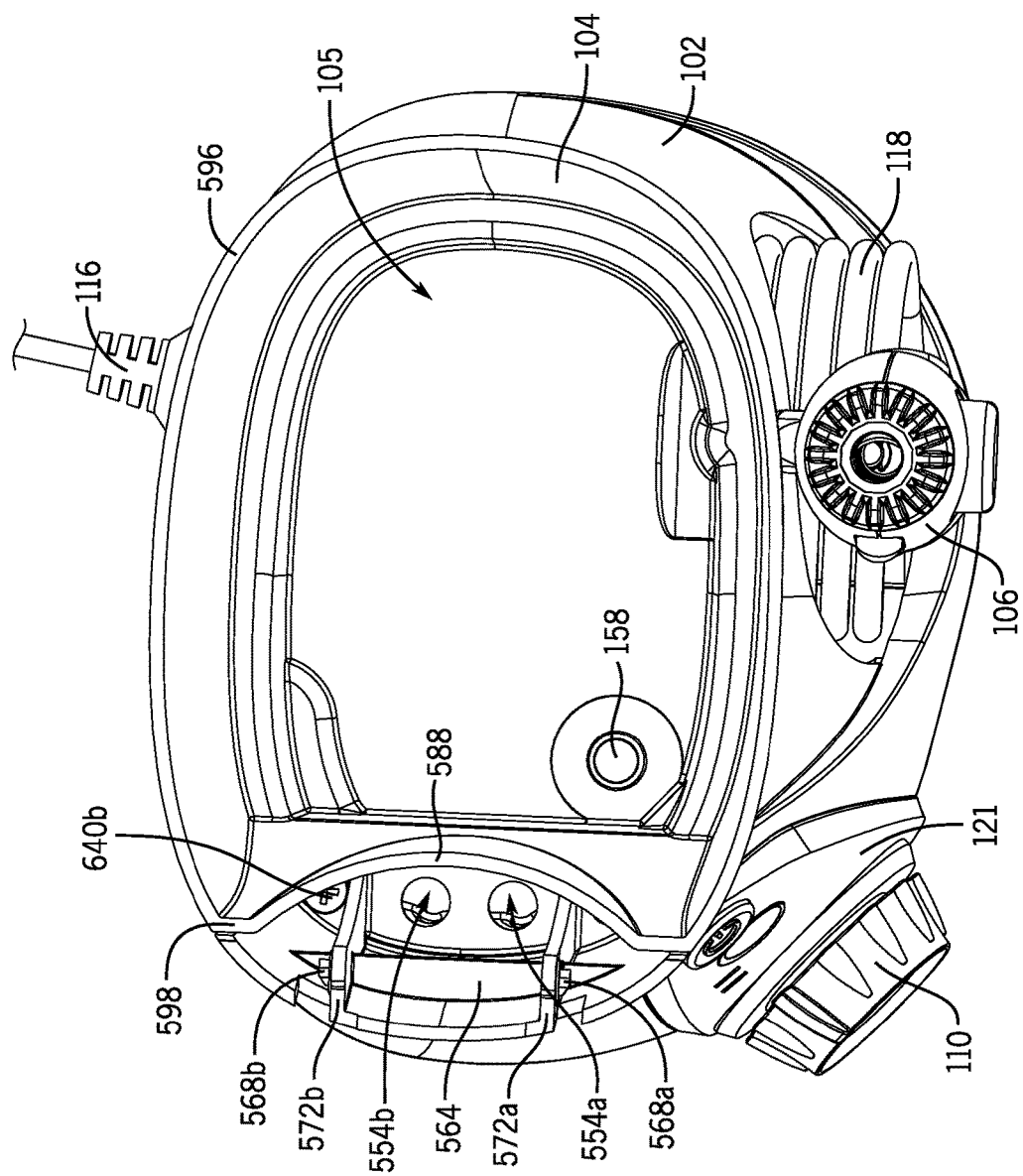
FIG. 17 is a top perspective view of the oral irrigator of FIG. 1A with the lid removed.
Figure 18:
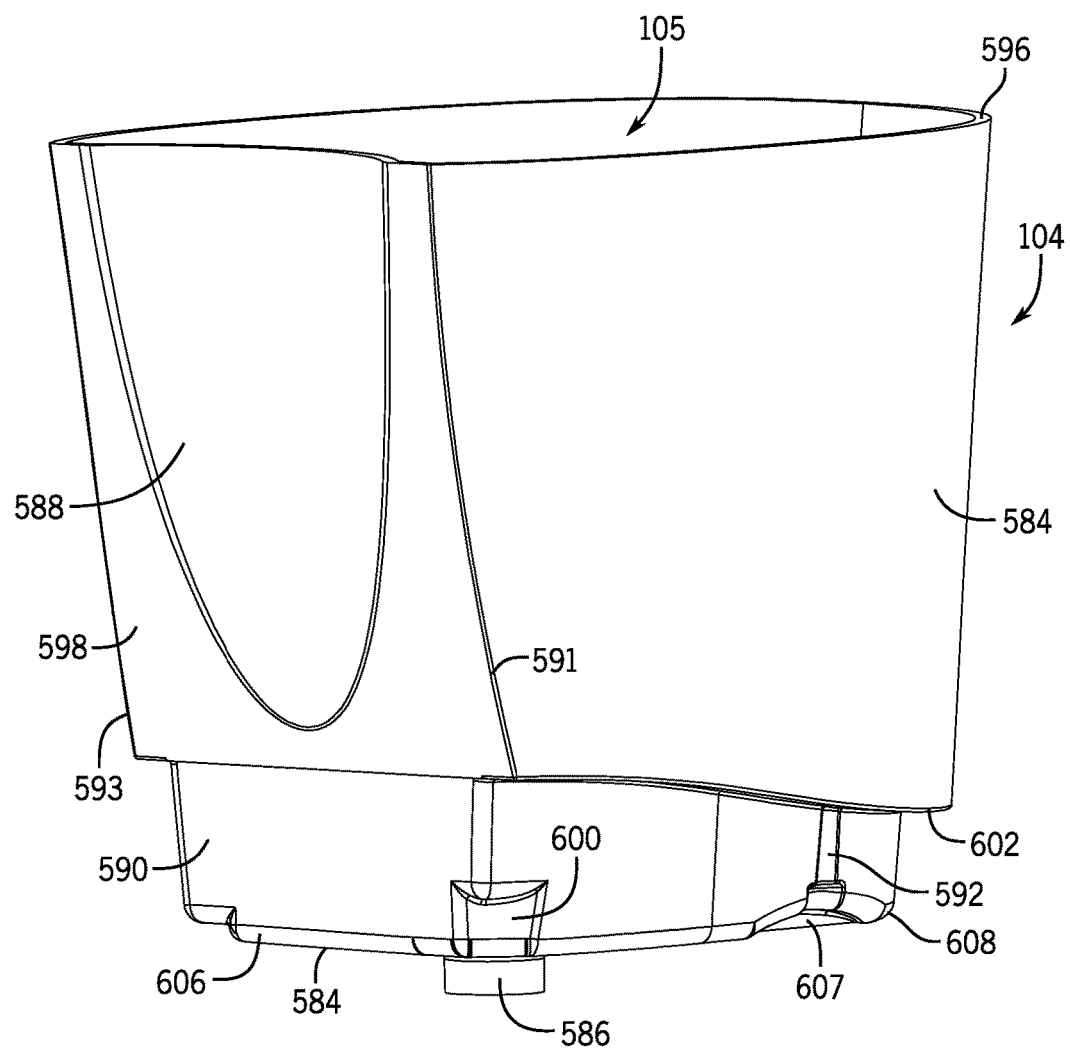
FIG. 18 is a left side perspective view of a reservoir of the oral irrigator of FIG. 1A.

With reference to FIGS. 1A, 4B, 17, and 18, the reservoir 104 defines the cavity 105 for holding fluid and is in fluid communication with the pump 146 and the handle 106. FIG. 18 is an isometric view of the reservoir removed from the base. With reference to FIGS. 17 and 18, the reservoir 104 includes a main body 584 defining the cavity 105. The main body 584 extends upwards and outwards from a foundation 590 defining an overhang 602. In this embodiment the main body 584 has a larger diameter than the foundation 590 to allow the outer surface of the main body 584 to be substantially flush with the upper base 130 when the reservoir is received onto the upper base 130 as the foundation 590 seats within the receiving cavity 512 of the upper base 130.

The main body 584 may be generally oval or oblong shaped, with the exception that one sidewall may be relatively planar. For example, the main body 584 may include an interfacing sidewall 598 that is configured to be oriented towards the prow 103 when connected to the upper base 130. In this embodiment, the interfacing sidewall 598 may be substantially planar but may include a parabolic shaped depression 588 defined therein. The depression 588 is curved inwards towards the center of the cavity 105 and diverges laterally to increase in chord length as it approaches the top edge 596 of the main body 584. The main body 584 terminates at a top edge 596 that defines the upper surface of the reservoir 102.

The reservoir 104 may also include one or more keying structures 592, 600 positioned on the sidewalls of the foundation 590 or the bottom surface 594 of the reservoir 104. In some embodiments, the foundation 590 varies in thickness from a first end 606 towards a second end 608. The variation in thickness allows the main body 584 to follow the curved profile of the top edge 524 when connected to the upper base 130.

With reference to FIGS. 4B and 18, the reservoir 104 includes an outlet 610 (see FIG. 4B) defined as am aperture through the bottom surface 594. A collar 586 extends from the bottom surface 594 to surround the outlet and further define a lumen for fluid flow between the reservoir 104 and pump 146. The outlet 610 may vary in diameter along its length. For example, the diameter of the outlet 610 through the collar 586 may be larger than the diameter of the outlet 610 as defined through the bottom surface 594. In this example, the bottom surface 594 of the reservoir 104 defines a shelf 612 within the flow pathway of the outlet 610.

Figure 1C:
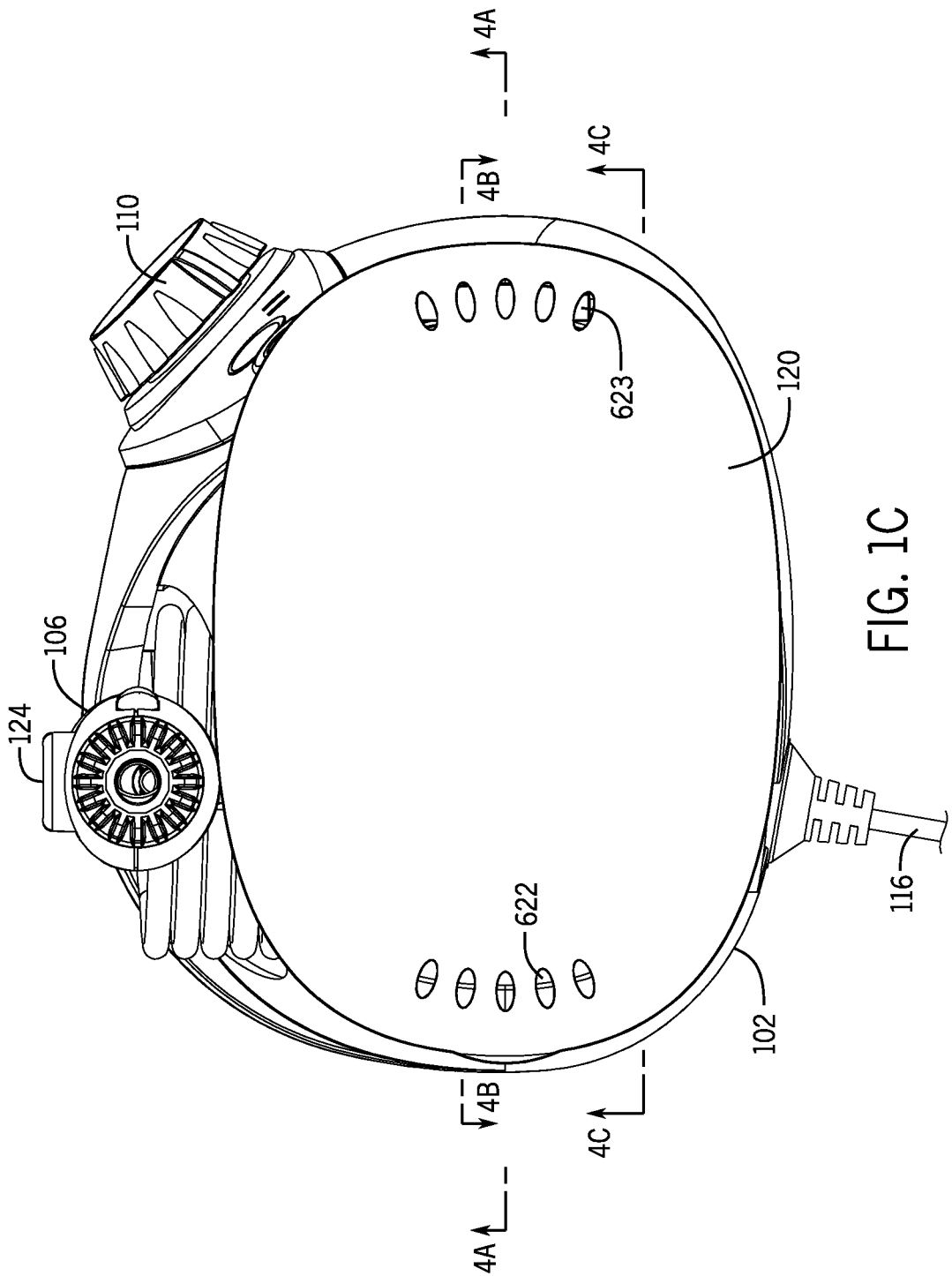
FIG. 1C is a top plan view of the oral irrigator of FIG. 1A.
Figure 1D:
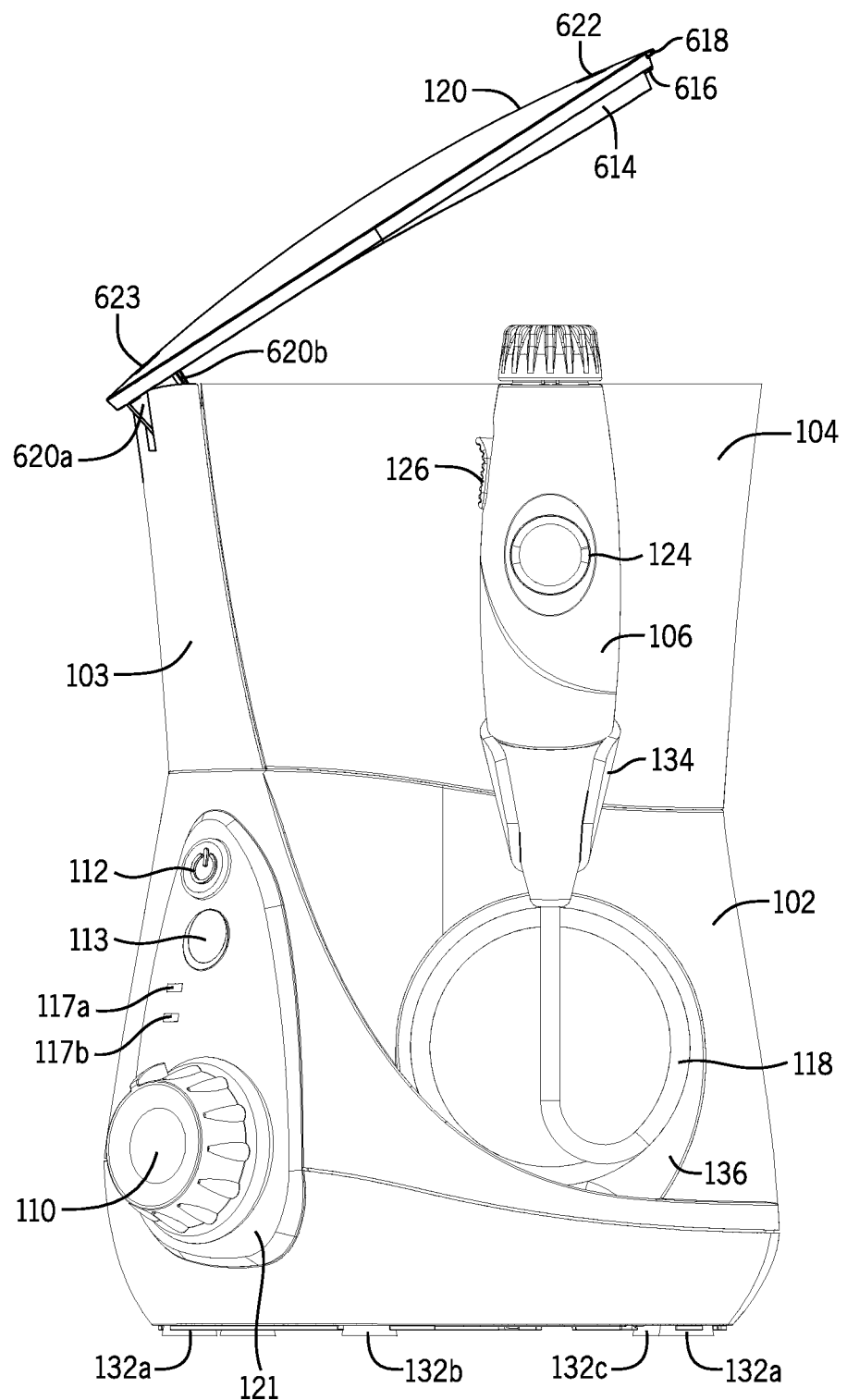
FIG. 1D is a front elevation view of the oral irrigator of FIG. 1A with a lid partially open.
Figure 1E:
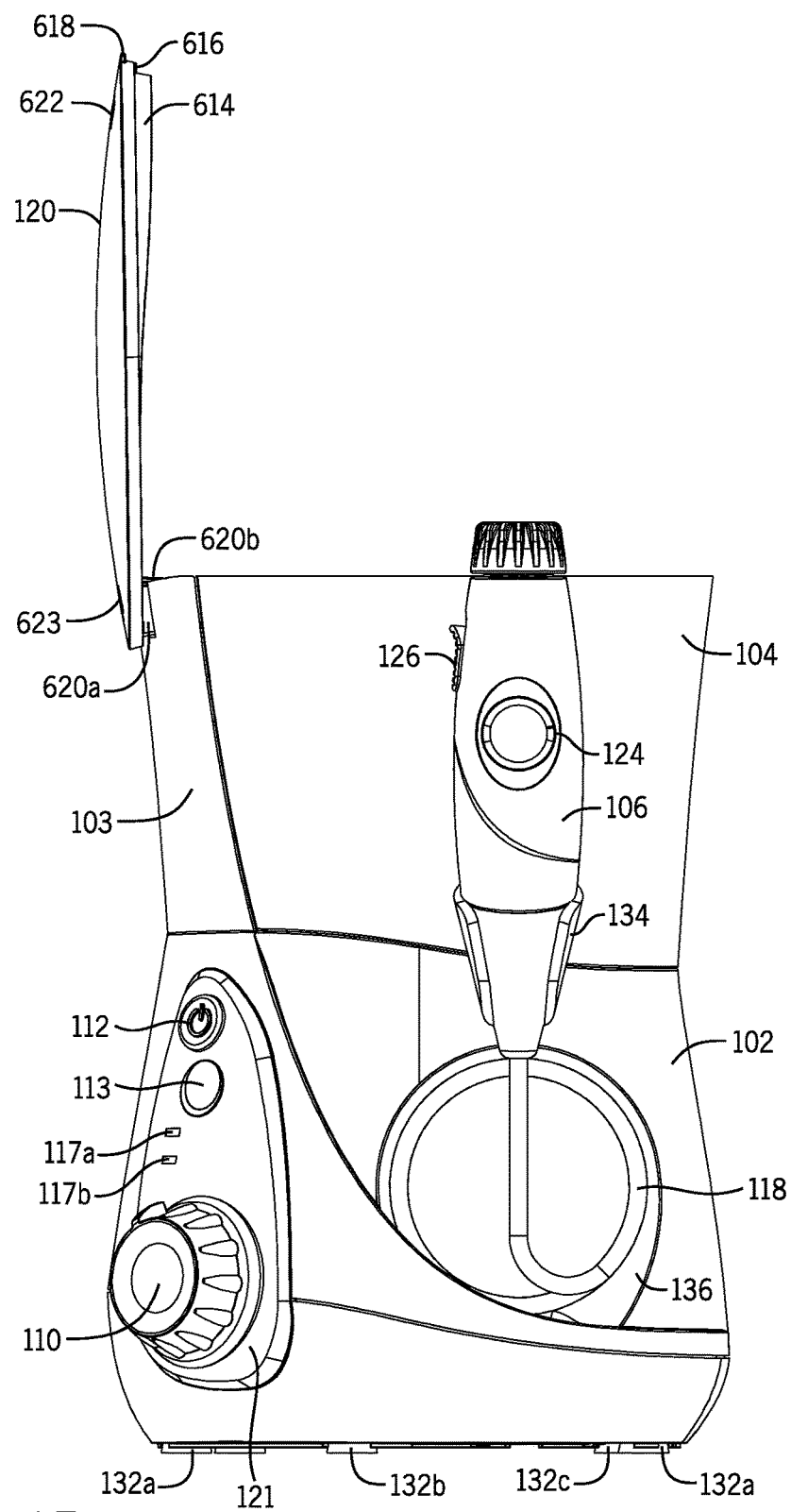
FIG. 1E is a front elevation view of the oral irrigator of FIG. 1A with the lid completely open.

The lid will now be discussed in more detail. The lid 120 forms a cover for the reservoir 104 and is rotatably connected to the prow 103. FIGS. 19A and 19B illustrate various views of the lid. With reference to FIGS. 1C, 19A and 19B, the lid 120 is generally configured to match the shape of the perimeter of the top edge 596 of the main body 584 of the reservoir 104 and span across the perimeter to cover the reservoir. A sidewall extends from an interior surface of the lid 120 downwards and surrounds the perimeter of the lid 120.

A sealing rim 614 extends downward from an interior surface of the lid 120 and is positioned within a sidewall 636 extending about a perimeter of the lid 120. In some embodiments, the sealing rim 614 may be positioned closer towards a center of the lid 120 than the sidewall 636. In these embodiments, the sealing rim 614 is configured to be received on an interior side of the reservoir 104 and the sidewall 636 may be configured to be received either on the top edge 596 or on the exterior side of the reservoir 104 when the lid 120 is closed.

A finger grip 618 extends outwards from the sidewall 636 of the lid 120. The finger grip 618 defines a gripping surface to allow a user to grip the lid 120 to open and close the lid 120. A catch 616 is defined on the rim 614 and is substantially aligned with the user engagement tab 618. This catch 616 seats on the top edge of the reservoir 104 to assist in propping the lid 120 upon the reservoir 104.

The lid 120 optionally includes a plurality of vents 622, 623 which may be apertures defined through an exterior surface of the lid 120 to an interior surface of the lid 120. A first set of vents 622 is oriented towards the first end 632 and are arranged in a pattern that generally follows the curvature of the sidewall 636 of the lid 120. The second set of vents 623 is positioned near the second end 634 and mirrors the orientation of the first vent set 622. In one example, the vents 622, 623 are oval shaped; however, many other shapes and sizes are envisioned.

With reference to FIGS. 19A and 19B, the lid 120 includes two tangs 621a, 621b that extend downward from the interior surface of the lid 120. The tangs 621a, 621b are spatially separated from and parallel to each other. The tangs 621a, 621b decrease in width as they extend downwards. The tangs 621a, 621b are flexible and resilient, which allows the tangs 621a, 621b to deform and resiliently spring back to an original shape and/or position. As will be discussed below, the tangs 621a, 621b assist in securing the lid 120 in select positions relative to the reservoir 104.

With continued reference to FIGS. 19A and 19B, the lid 120 further includes two hinges 620a, 620b that also extend downward from the interior surface of the lid 120. The hinges 620a, 620b are positioned towards the second end 634 of the lid 120. The hinges 620a, 620b are positioned further apart from one another than the tangs 621, 621. In one example, the second set of vents 623 are positioned between the hinges 620a, 620b. The hinges 620a, 620b each include a first side 626a, 626b that is substantially straight as it extends from the attachment end of the hinges 620a, 620b towards a free end 630a, 630b. Before reaching the free end 630a, 630b, the hinges 620a, 620b transition from the straight edge defining the first side 626a, 626b to define a step 638a, 638b. At the step 638a, 638b, the hinges 620a, 620b define a stop 628a, 628b. The stops 628a, 628b are shoulders extending beyond the surface of the step 638a, 638b. From the stops 628a, 628b, the hinges 620a, 620a curve around to extend back to the interior surface of the lid 120.

Assembly of the Oral Irrigator

The assembly and interconnection between the elements of the oral irrigator 100 will now be discussed in more detail. With reference to FIGS. 1A, 3, 4A, 4B, and 15, the pump assembly 119 and internal components for the oral irrigator 100 are positioned within the lower base 128 and secured thereto. In some embodiments, one or more isolators 168 may connect the chassis 140 of the pump assembly 119 to the lower base 128. The isolators 168 are configured to absorb vibrations from the motor 142 and the pump 146 and reduce the vibrations that may be transmitted to the base body 128 and/or feet 132a, 132b, 132c, 132d. For example, the isolators 168 may be an elastomeric material or other material configured to absorb vibrations.

After the pump assembly 119 is connected to the lower base 128, the control faceplate 121 is positioned within the faceplate cutout 504 and the control knob 110 is connected to a stem 648 extending from the pump 146 through an aperture in the faceplate 121, securing the faceplate 121 and control knob 110 to the pump 146.

The upper base 130 is then positioned over the pump assembly 119 and lower base 128 and columns 646a, 646b, 646c, 646d extending from the top portion of the upper base 130 are fitted into corresponding columns 644a, 644b, 644c, 644d extending upwards from the lower base 128. The back wall of the hose cavity 136 is positioned behind the hose wall aperture 502 and the lower base 128 is secured to the upper base 130. In particular, fasteners 642 are received into each of the feet 132a, 132b, 132c, 132d and into the columns 644a, 644b, 644c, 644d of the lower base 128 and the columns 646a, 646b, 646c, 646d of the upper base 130 to secure the lower base 128 to the upper base 130.

With reference to FIGS. 4B and 15, the valve body 155 engages with the collar 586 extending from the interior side of the top surface 508 of the upper base 130. A seal 162 is received between the interior side of the top surface 508 and the top end of the valve body 155 to seal connection between the reservoir 104 and base 102.

With the upper base 130 and the lower base 128 are secured together, the prow 103 is attached to the upper base 130, or alternatively the prow 103 can be attached to the upper base 130 before the upper base 130 is attached to the lower base 128. With reference to FIGS. 3, 4A, 13B, 14, 15, and 16B, the prow 103 is aligned with the prow recess 522 of the upper base 130 and an outer edge of the shelf 556 is positioned in the prow recess 522 (see FIG. 4A). In some embodiments, only the edge of the shelf 556 is positioned in the prow recess 522 so that the base 130 does not interfere with tips being received into the tip apertures 554a, 554b.

The remaining portions of the base 546 of the prow 103 are positioned on the top edge 524 of the upper base 130. The fastening apertures 580a, 580b of the prow 103 are aligned with corresponding fastening aperture 537a, 537b in the upper base 130. Once the fastening apertures of the prow 103 are aligned with the fastening apertures in the upper base 130, fasteners 640a, 640b are received into the fastening apertures 580a, 580b and extend into the fastening apertures 537a, 537b connecting the prow 103 to the upper base 130.

As shown in FIGS. 4A and 14, when connected to the upper base 130, the prow 103 is aligned such that the tip apertures 554a, 554b are positioned above the drip catch 516 and first drainage path 514. As will be discussed in more detail below with respect to FIG. 20, the alignment of the tip apertures 554a, 554b and the drip catch 516 allows fluid that may drip from the accessories (e.g., if they are wet after use) to fall or flow into the drip catch 516.

After the prow 103 is connected to the upper base 130, the lid 120 may be removably connected to the prow 103. With reference to FIGS. 13A, 13B, 16A-16C, 19A, and 19B, the pivots 568a, 568b are received through the pivot apertures 624a, 624b of the hinges 620a, 620b. The angled side 582 of the pivots 568a, 568b allows the hinges 620a, 620b to be more easily slide onto the pivots 568a, 568b, for example, as the hinges 620a, 620b extend from the outer surface 550 of the prow 103 through the hinge slits 566a, 566b to connect to the pivots 568a, 568b. When the lid 120 is connected to the prow 103 the hinges 620a, 620b are positioned within the hinge slits 566a, 566b and allowed to rotate within the slits. Operation of the lid 120 will be discussed in more detail below.

The valve 158, O-ring 160, and spring 650 are received into the collar 586 of the reservoir 104. The head of the valve 158 and O-ring 160 extend through the outlet 610 and are positioned above the bottom surface 652 of the reservoir 104. The spring 650 is wrapped around the remaining portions of the valve 158 and contained within the collar 586. As the valve 158 and O-ring 160 are both connected to the reservoir 104, the reservoir 104 can be removed and refilled without fluid leaking through the outlet 610. In particular, when the reservoir 104 is disconnected from the base 102, the spring 650 is decompressed, allowing the head of the valve 158 and O-ring 160 to seal against the bottom surface 652 of the reservoir 104, preventing fluid from entering into the outlet 610. As the reservoir 104 is positioned on the upper base 130, the collar 586 is received into the valve aperture 511 on the upper base 130. As the reservoir 104 is lowered into the receiving cavity 512, a prong 654 of the pump 146 (see FIG. 4B) engages the bottom of the valve 158. The prong 654 overcomes the biasing force of the spring 650 to force the valve body 158 upwards, disengaging the O-ring 160 and valve body 158 from the bottom surface 652 of the reservoir 104. Once the valve and O-ring are disengaged, fluid can flow around the valve body 158 and O-ring 160 into the pump 146.

Attachment of the reservoir 104 to the base 102 will now be discussed in further detail. With reference to FIGS. 1E, 4A, 4B, 15, and 18, the lid 120 is rotated to the fully open position illustrated in FIG. 1E exposing the top surface 508 of the upper base 130. The user then may navigate the reservoir 104 into the receiving cavity 512 and position the foundation 590 in the receiving cavity 512. The keying structure 592 is aligned with the corresponding keying structure 545 on the upper base 130 to align the reservoir 104 in the receiving cavity 512. The raised seat 544 extends into a corresponding depression 607 on the bottom surface of the main body 584. The interfacing sidewall 598 of the reservoir 104 is aligned to face the prow 103 and the collar 586 extending from the reservoir 104 is received into the valve aperture 511 in the upper base 130.

When positioned in the receiving cavity 512, the foundation 590 of the reservoir 104 is hidden from view by the upper base 130 and the overhand 602 sits on the top edge 524 of the upper base 130. In this example, the sidewalls of the main body 584 may be substantially flush with the sidewalls of the upper base 130.

With reference to FIGS. 1A-1E, when the reservoir 104 is positioned in the receiving cavity 512 of the upper base 130, the edges 591, 593 of the interfacing sidewall 598 are aligned with the ledges 510, 542 on the upper base 130. In this manner, the aesthetic element defined by the ledges 510, 542 extends through the reservoir 104 to create an aesthetically pleasing design for the oral irrigator.

Once the reservoir 104 is connected to the base 102 and a tip 114 is connected to the handle 106 the oral irrigator 100 the oral irrigator 100 can be used. To activate the oral irrigator 100, the use selects the activation button 112, which provides power to the motor 142 to activate the pump 146. As described above with respect to the massage mode, once the motor 142 is powered, the motor 142 drives the pump 146 which pulls fluid from the reservoir 104 through the outlet 610. Fluid flows around the valve 158 and O-ring 160 and into the pump 146 and is then forced through the hose 118 to the tip 114.

Accessory Storage and Drainage

Figure 20:
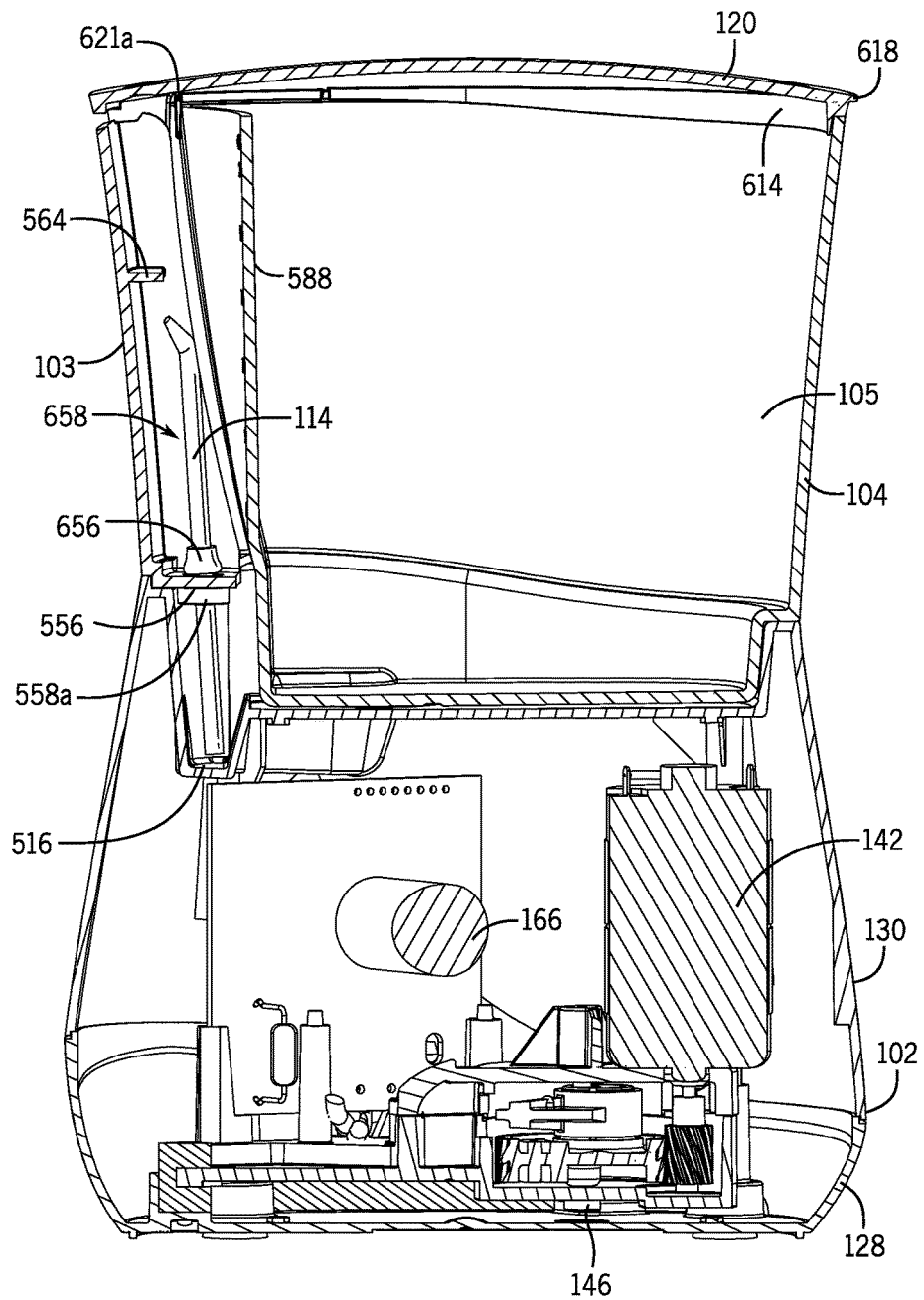
FIG. 20 is a cross-section view of the oral irrigator of FIG. 1A illustrating an accessory stored in a storage compartment.

With reference to FIGS. 16A and 20, a storage compartment 658 is defined between the interfacing sidewall 598 and the prow 103. In particular, the curvature of the depression 588 away from the prow 103 increases a volume between the prow 103 and the reservoir to define a cavity where one or more accessories for the oral irrigator 100 can be stored. As shown in FIG. 20, a tip 114 is positioned within the storage compartment 658. The tip 114 is positioned within one of the tip apertures 554a, 554b defined in the shelf 556. In some embodiments, the tip 114 may include a tip collar 656 or another area having a larger diameter than the tip aperture 554a, 554b that acts to retain the tip 114 at a selected position within the storage compartment 658.

With continued reference to FIG. 20, in the storage compartment 658 the tip 114 (or other accessories stored therein) may be covered by the lid 120 (when closed), and further may be partially protected by the horizontal rib 564. The rib 564 and lid 120 help to prevent fluids and debris from entering into the storage compartment and landing on the tip 114.

As shown in FIG. 20, in some embodiments a portion of the tip 114 may be configured to extend past the edge of the sleeve 558a, 558b, but it should be noted that in other embodiments, the tip 114 may not extend through the sleeve 558a, 558b. The tip apertures 554a, 554b are configured to position the tip 114 above the drip catch 516. This positioning allows fluid and debris that has accumulated on the tip 114, tip collar 656, or shelf 556 to fall into the drip catch 516. With reference to FIGS. 15 and 20, debris and fluid that falls into the drip catch 516 are encouraged through the pitch of the first drainage path 514 to flow towards the drain outlet 520 and exit the oral irrigator 100. Additionally, the reservoir 104 can be removed and fluid may be poured into the drip catch 516 which will drain out through the outlet 520 to clean the first drainage path 514. This helps to clean the oral irrigator 100 and prevent the accumulation of debris and fluid, which may help to reduce bacterial and fungus growth on the base 102 and/or accessories stored within the storage compartment.

With continued reference to FIG. 15, the second drainage path 528 and drain channel 530 help to encourage fluid and debris that may accumulate underneath the reservoir 104 to exit the oral irrigator 100. In particular, fluid that may leak from the reservoir 104, drip around the sidewalls of the reservoir 104, or otherwise leak between the reservoir 104 and the top surface 508 of the base 102, may flow to the recessed areas of the drain path 528 and drain channel 530. Once fluid enters into the drain channel 530, the pitch of the channel 530 is configured to encourage (through the help of gravity) fluid to flow out of the drain outlet 520. The second drainage path 528 and drain channel 530 are recessed below the top surface 508 of the base 130 and are positioned below the bottom surface of the reservoir 104 when connected to the base 130 to prevent the reservoir 104 from blocking the flow path between the drain channel 530 and the drain outlet 520.

Lid Operation

Figure 21:
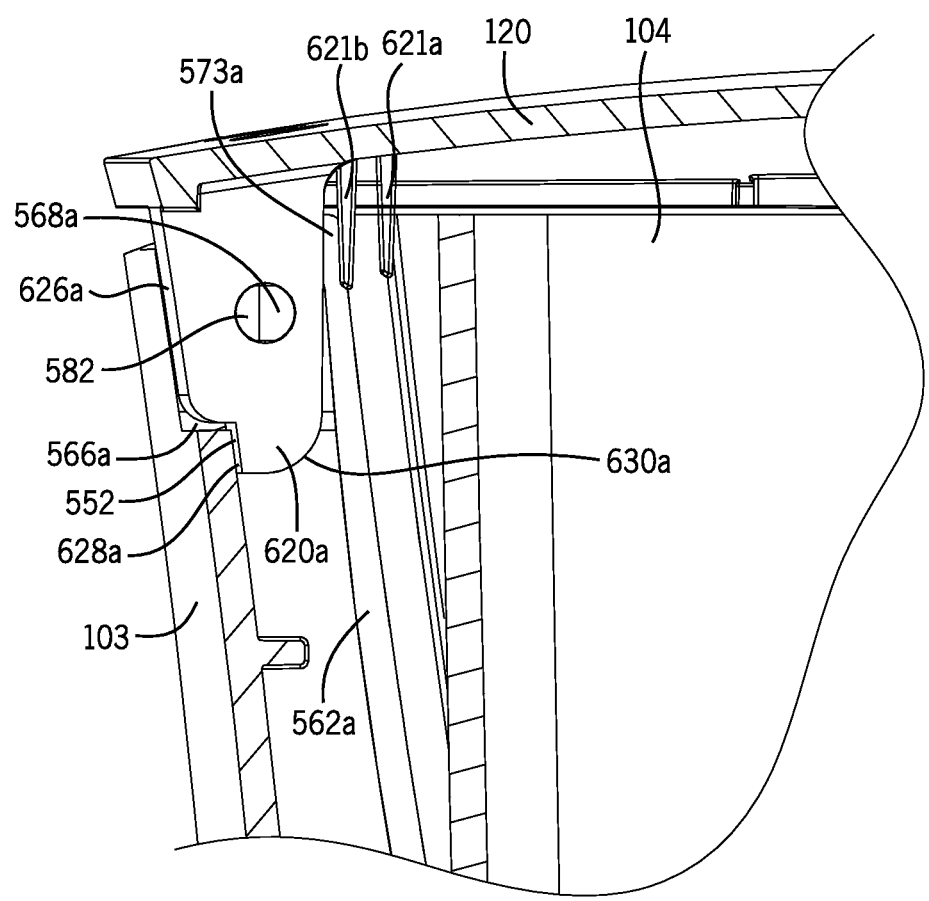
FIG. 21 is an enlarged cross-section view of the oral irrigator taken along line 21-21 in FIG. 1B illustrating the lid in a closed position.
Figure 22A:
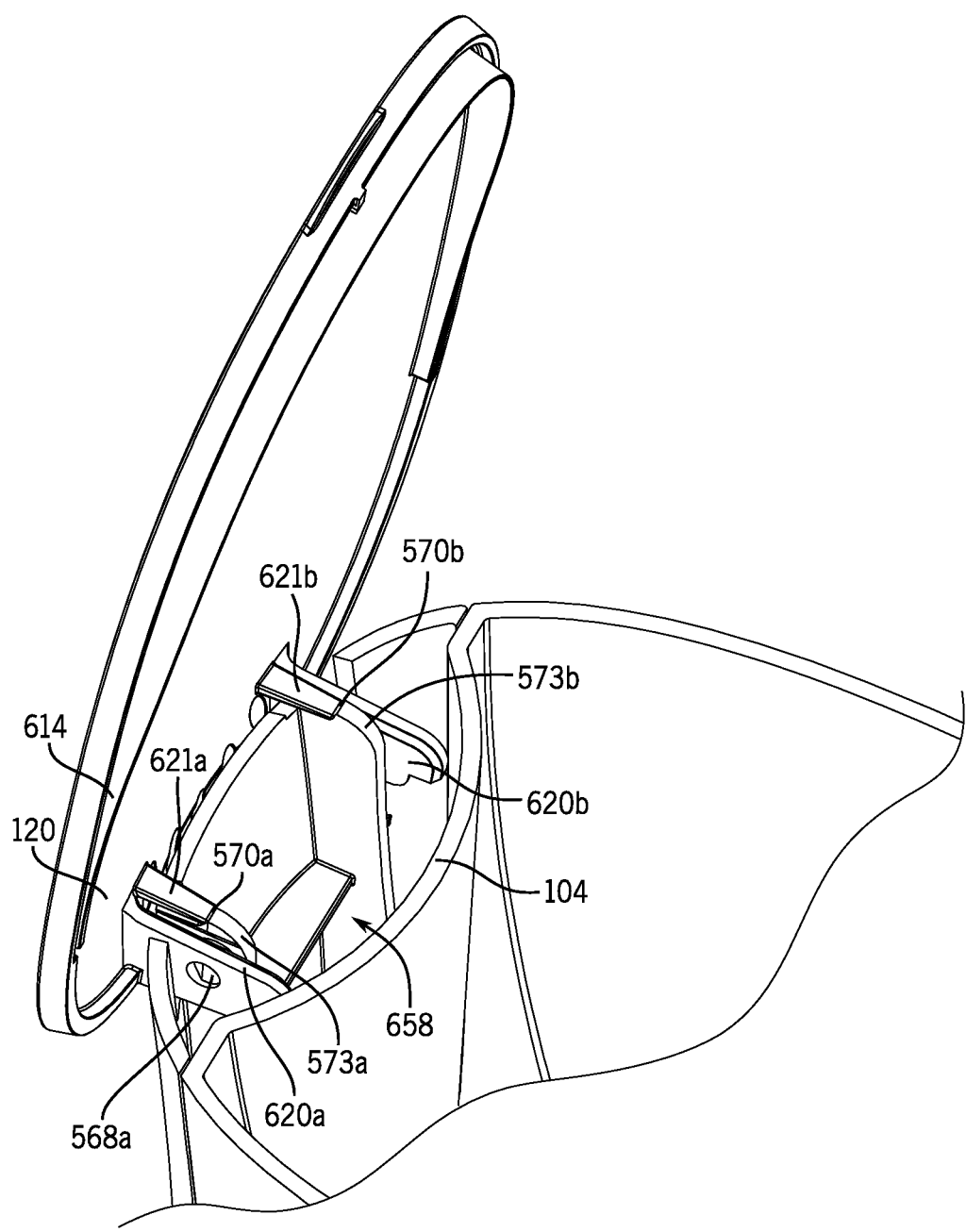
FIG. 22A is an enlarged top perspective view of the oral irrigator of FIG. 1E.
Figure 22B:
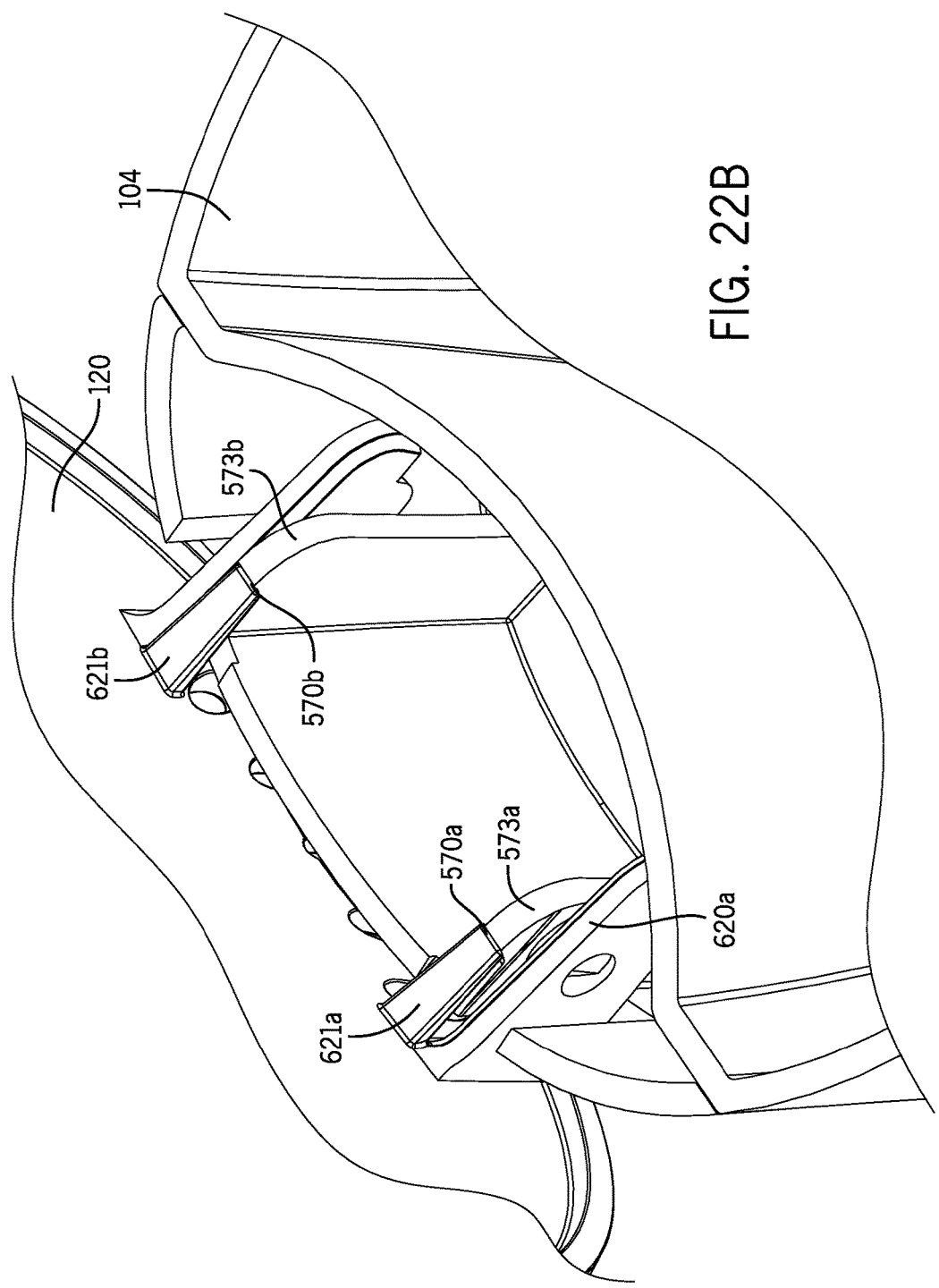
FIG. 22B is an enlarged top perspective view of the oral irrigator similar to FIG. 22A illustrating the lid transitioning between the open position and the closed position.

As described above, the lid 120 is rotatably connected to the prow 103. Rotation of the lid between fully open and fully closed will now be discussed. FIG. 21 is an enlarged view of the oral irrigator with the lid in a closed position. FIG. 22A is an enlarged view of the oral irrigator with the lid in an open position. FIG. 22B is an enlarged view of the oral irrigator with the lid as it transitions from the closed position to the open position. As shown in FIGS. 21-22B, the hinges 620a, 620b and tangs 621a, 621b assist in positioning the lid and retaining the lid in select orientations. Each will be discussed in turn below.

As shown in FIGS. 4A and 4B, when the lid 120 is closed, the sealing rim 614 is positioned on an interior side of the reservoir 104 and the lid sidewall 636 seats on the top edge of the reservoir 104. With the reservoir 104 positioned in the upper base 130, the reservoir 104 acts to limit the rotation of the lid 120. However, with reference to FIG. 21, in instances when the reservoir 104 is not connected, the hinges 620a, 620b are configured with stops 628a, 682b to limit the rotation of the lid 120 relative to the prow 103. For example, as the lid 120 rotates on the pivots 568a, 568b, the hinges 620a, 620b are moved from a position relatively perpendicular to the prow 103 (see FIG. 22A), to a position relatively parallel with the prow 103 (see FIG. 21). The steps 638a, 638b of the hinges 620a, 620b are able to clear the edge of the hinge slits 566a, 566b, but once the lid 120 has been rotated to the closed position, the stops 628a, 682b engage the interior wall 552 of the prow 103 and cannot pass through the hinge slits 566a, 566b. The engagement between the stops 628a, 628b and the prow 103 prevents the lid 120 from rotating further towards the upper base 130.

The stopping mechanisms of the lid 120 and prow 103 help to prevent the lid 120 from swinging into the prow 103 when the reservoir 104 is removed. This helps to prevent damage to the lid 120, pivots 568a, 568b, and/or prow 103. Additionally, because the lid 120 is held in the closed position that is relatively perpendicular to the prow 103 by the engagement of the stops 628a, 628b with the prow 103, the user may not have to lift the lid 120 to position the reservoir 104 in the base 130 after refilling it. This is because the user can slide the reservoir 104 underneath the lid 120 while it is held in the closed position and as the user slides the reservoir 104 beneath the lid 120, the reservoir 104 can prop the lid 120 up sufficiently to be attached to the upper base 130.

In the open position, the lid 120 may include detents that help hold the lid 120 open. With reference to FIG. 22A, in the open position the tangs 621a, 621b of the lid 120 are received within seats 572a, 572b of the prow 103. In this position, the shoulders 570a, 570b are raised above the tangs 621a, 621b, to prevent the tangs 621a, 621b from sliding forward towards the reservoir 104. As shown in FIG. 22A, in the upright position of the lid 120, the free end of the tangs 621a, 621b may not engage the front surface of the shoulders 570a, 570b defining a space between the shoulders 570a, 570b and the tangs 621a, 621b. The shoulders 570a, 570b help to prevent accidental closer of the lid 120, as a force is required to lift the tangs 621a, 621b up and over the shoulders 570a, 570b to free the lid 120 to rotate on the pivots 568a, 568b.

As a user provides a force to the lid 120 to close the lid 120, the tangs 621a, 621b are lifted from the seat 572a, 572b. With reference to FIG. 22B, as the lid 120 is rotated downward and the force applied to the lid 120 is sufficient to overcome the resistance force of the free end of the tangs 621a, 621b from engaging the shoulders 570a, 570b, the tangs 621a, 621b, due to their resilient nature, deflect upwardly to rise above the shoulders 570a, 570b. As the tangs 621a, 621b deflect, they rotate around the cam surfaces 573a, 573b of the ribs 562a, 562b of the prow 103. The tangs 621a, 621b rotate on the cam surfaces 573a, 573b as the lid 120 rotates around the pivots 568a, 568b until reaching the closed position of the lid 120 as shown in FIG.

21. In the closed position, the tangs 621*a*, 621*b* are oriented substantially parallel with the ribs 562*a*, 562*b*.

CONCLUSION

The foregoing description has broad application. For example, while examples disclosed herein may focus on a massage mode for oral irrigators, it should be appreciated that the concepts disclosed herein may equally apply to other motor driven devices where a variation in motion may be desired. Similarly, although the massage mode module is discussed with respect to reducing a pulse rate to create a massage feeling, the devices and techniques disclosed herein are equally applicable to modifying the pulse rate or pressure of an outlet fluid for other applications (e.g., creating a faster pulse rate for quicker or more effective cleaning). Accordingly, the discussion of any example is meant only to be exemplary and is not intended to suggest that the scope of the disclosure, including the claims, is limited to these examples.

Although the present invention has been described with reference to preferred examples, persons skilled in the art will recognize that changes may be made in form and detail without departing from the spirit and scope of the invention. The invention is limited only by the scope of the following claims.

What is claimed is:

1. An oral irrigator comprising
   a base;
   a prow connected to the base and extending upwards therefrom wherein the prow comprises at least one rib oriented vertically relative to the prow, the rib comprising a pivot extending from the side wall of the rib, a seat defined on a top surface of the rib, and a cam surface;
   a reservoir defining a fluid cavity, wherein the reservoir is removably connected to the base; and
   a lid rotatably connected to the prow; wherein
   the lid rotates relative to the prow between a first position exposing the fluid cavity to a second position covering at least a portion of the fluid cavity.

2. The oral irrigator of claim 1, wherein the lid remains connected to the prow when the reservoir is removed from the base.

3. The oral irrigator of claim 1, further comprising a storage compartment defined by an inner wall of the prow and a sidewall of the reservoir.

4. The oral irrigator of claim 3, wherein the prow further comprises a shelf extending from the inner wall, wherein the shelf comprises at least one tip aperture configured to receive an accessory of the oral irrigator.

5. The oral irrigator of claim 4, wherein the base further comprises
   a top surface;
   at least one drain path recessed below the top surface and in fluid communication with therewith; and
   an outlet defined in a sidewall of the base in fluid communication with the at least one drain path; wherein
   the reservoir seats on the top surface of the base.

6. The oral irrigator of claim 4, wherein the at least one drain path comprises a drip catch positioned below the shelf of the prow.

7. The oral irrigator of claim 1, wherein the lid comprises
   a hinge operably connected to the pivot;
   a tang extending from an interior surface of the lid; wherein
   in the first position of the lid the tang is received in the seat defined on the top surface of the rib; and
   to transition from the first position to the second position, the tang travels over the cam surface.

8. The oral irrigator of claim 7, wherein the lid further comprises a plurality of venting apertures.

9. An irrigating device comprising
   a handle operably connected to an irrigating tip;
   a reservoir in fluid communication with the handle;
   a base operably connected to the reservoir and the handle;
   a lid operably connected to the base; wherein
   removal of the reservoir from the base is independent of removal of the lid from the base; and a backbone operably connected to a first end of the base and the lid is rotatably connected to the backbone, wherein the backbone comprises at least one rib oriented vertically relative to the backbone, the backbone comprising a pivot extending from a sidewall of the rib, a seat defined on a top surface of the rib, and a cam surface.

10. The irrigating device of claim 9, wherein the backbone extends vertically upward from the base.

11. The irrigating device of claim 10, wherein a sidewall of the reservoir and an inner surface of the backbone define a storage compartment.

12. The irrigating device of claim 11, wherein the base further comprises a drip catch defined in a top surface of the base and positioned below the storage compartment.

13. The irrigating device of claim 12, wherein the drip catch is angled to encourage fluid flow to flow from the drip catch to a drain outlet defined in a sidewall of the base.

14. The irrigating device of claim 11, wherein the reservoir further comprises a depression in the sidewall, wherein the depression is concavely shaped to increase the volume of the storage compartment.

15. The irrigating device of claim 10, wherein the lid comprises a stop configured to limit rotation of the lid in a first direction.

16. A countertop oral irrigator comprising
    a pump assembly;
    a housing enclosing the pump assembly;
    a reservoir removably positioned on a top surface of the housing;
    a prow extending upward from the housing and being substantially parallel to a first side of the reservoir, wherein the prow comprises at least one rib oriented vertically relative to the prow, the rib comprising a pivot extending from the side wall of the rib, a seat defined on a top surface of the rib, and a cam surface; and
    a lid rotatably connected to the prow; wherein
    in an open position the lid uncovers the reservoir; and
    in a closed position the lid covers the reservoir.

17. The countertop oral irrigator of claim 16, wherein the prow has a top edge that is in the same plane as a top edge of the reservoir.

* * * * *